United States Patent [19]

Ikawa et al.

[11] Patent Number: 5,276,150

[45] Date of Patent: Jan. 4, 1994

[54] 1,4-DIHYDROPYRIDINE DERIVATIVES

[75] Inventors: Hiroshi Ikawa; Akiyoshi Kadoiri; Nobuo Kobayashi; Yasuko Konagai, all of Tokyo; Yasuo Sekine, Yokohama, all of Japan

[73] Assignee: Fujirebio Inc., Tokyo, Japan

[21] Appl. No.: 850,201

[22] Filed: Mar. 12, 1992

Related U.S. Application Data

[63] Continuation of Ser. No. 529,445, May 29, 1990, abandoned.

[30] Foreign Application Priority Data

May 31, 1989 [JP] Japan .................. 1-136208

[51] Int. Cl.$^5$ .................. C07D 409/04; C07D 419/04; C07D 217/18; C07D 417/04
[52] U.S. Cl. .................. 544/238; 544/333; 544/405; 544/269; 546/144; 546/167; 546/193; 546/256; 546/257; 546/283; 546/284
[58] Field of Search .............. 546/193, 283, 257, 256, 546/144, 283, 284, 167; 544/405, 238, 333, 269

[56] References Cited

U.S. PATENT DOCUMENTS

| | | | |
|---|---|---|---|
| 4,558,058 | 12/1985 | Schönafinger et al. | 546/277 |
| 4,618,607 | 10/1986 | Araki et al. | 544/122 |
| 4,686,217 | 8/1987 | Baxter et al. | 546/193 |
| 4,705,786 | 11/1987 | Yamamoto et al. | 514/252 |
| 4,791,122 | 12/1988 | Stoltefuss et al. | 546/312 |

FOREIGN PATENT DOCUMENTS

| | | |
|---|---|---|
| 0325130 | 7/1989 | European Pat. Off. |
| 3501855 | 7/1986 | Fed. Rep. of Germany |

OTHER PUBLICATIONS

Schoenafinger et al., CA 111:43289c Abstract of DE 3709352 published Sep. 29, 1988.
Schoenafinger et al. CA 110:39005v Abstract of DE 3707236 published Sep. 15, 1988.

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

1,4-Dihydropyridine derivatives of formula (I):

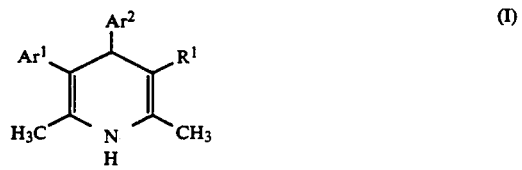

wherein $Ar^1$ and $Ar^2$ each represent an unsubstituted or substituted aromatic hydrocarbon or aromatic heterocyclic group; and $R^1$ represents $-CO_2R^2$, $-SO_2R^3$, $-COR^4$, $-CON(R^5)_2$, $-CN-$ or $-NO_2$ in which $R^2$ is hydrogen, a straight chain, branched chain or cyclic saturated hydrocarbon group, which may have a substituent or a straight chain, branched chain or cyclic unsaturated hydrocarbon group having 2 to 10 carbon atoms, which may have a substituent, $R^3$ is an alkyl group having 1 to 4 carbon atoms, $R^4$ is an alkyl group having 1 to 4 carbon atoms or a phenyl group; and $R^5$ is an alkyl group having 1 to 4 carbon atoms.

36 Claims, No Drawings

1,4-DIHYDROPYRIDINE DERIVATIVES

This application is a continuation of application Ser. No. 07/529,445, filed on May 29, 1990, now abandoned.

BACKGROUND OF THE INVENTION

The present invention relates to 1,4-dihydropyridine derivatives having superior vasodilative and platelet aggregation inhibiting activities.

Some of 1,4-dihydropyridine-3,5-dicarboxylate compounds have vasodilative effects based on the calcium entry blocking action and therefore are employed as coronary vasodilators, ameliorants of cerebral circulation, and hypotensive drugs.

Representative examples of such compounds are 1,4-dihydro-2,6-dimethyl-4-(2-nitrophenyl)pyridine-3,5-dicarboxylic acid dimethyl ester (generally referred to as "NIFEDIPINE"; U.S. Pat. No. 3,644,627) and 1,4-dihydro-2,6-dimethyl-4-(3-nitrophenyl)pyridine-3,5-dicarboxylic acid-3-[2-(N-benzyl-N-methylamino)ethyl]ester-5-methyl ester hydrochloride (generally referred to as "NICARDIPINE"; Japanese Patent Publication 55-45075).

In addition, 1,4-dihydropyridine compounds having both vasodilative based on the calcium entry blocking action and platelet aggregation inhibitory activities, are now being developed as disclosed, for example, in Japanese Laid-Open Patent Applications Nos. 56-140989, 60-215684, 61-10576, 61-5076, 61-197578, 60-226876, 61-47477, 61-212581, and 62-187468.

1,4-dihydropyridine compounds such as NIFEDIPINE and NICARDIPINE have high vasolidative activity based on the calcium entry blocking action, but are not satisfactory as remedy for atherosclerosis. Therefore, researches are being made for obtaining 1,4-dihydropyridine derivatives having not only vasodilating activity, but also platelet aggregation inhibitory activity, capable of inhibiting platelet aggregation and preventing and curing atherosclerosis, which can be used as remedies for circulatory system. However, satisfactory remedies having the above-mentioned activities have not been found yet.

SUMMARY OF THE INVENTION

It is therefore an object of the present invention to provide medicines capable of preventing and curing diseases of circulatory systems, which are particularly useful, for example, as hypotensive drugs, vasodilators, ameliorants of cerebral circulation, and anti-thrombotic drugs.

This object of the present invention is achieved by 1,4-dihydropyridine derivatives of formula (I):

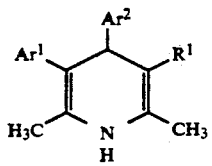

(I)

wherein $Ar^1$ and $Ar^2$ each represent an aromatic hydrocarbon group which may have a substituent, or an aromatic heterocyclic group which may have a substituent; $R^1$ represents a group selected from the group consisting of $-CO_2R^2$, $-SO\ R^3$, $-COR^4$, $-CON(R^5)_2$, $-CN$ or $-NO_2$; $R^2$ represents (i) hydrogen, (ii) a straight chain, branched chain or cyclic saturated hydrocarbon group having 2 to 10 carbon atoms, which may have a substituent selected from the group consisting of an alkyl group having 1 to 4 carbon atoms, an alkoxyl group having 1 to 4 carbon atoms, a phenoxy group which may have a substituent, a phenylthio group which may have a substituent, a substituted amino group, a cyclic amino group which may have a substituent, a phenyl group which may have a substituent, an aromatic heterocyclic group which may have a substituent, and a trihalomethyl group, or (iii) a straight chain, branched chain or cyclic unsaturated hydrocarbon group having 2 to 10 carbon atoms, which may have a substituent selected from the group consisting of an alkyl group having 1 to 4 carbon atoms, an alkoxyl group having 1 to 4 carbon atoms, a phenoxy group which may have a substituent, a phenylthio group which may have a substituent, a substituted amino group, a cyclic amino group which may have a substituent, a phenyl group which may have a substituent, an aromatic heterocyclic group which may have a substituent, and a trihalomethyl group; $R^3$ represents an alkyl group having 1 to 4 carbon atoms; $R^4$ represents an alkyl group having 1 to 4 carbon atoms or a phenyl group; and $R^5$ represents an alkyl group having 1 to 4 carbon atoms.

The present invention is based on the discovery that the above 1,4-dihydropyridine derivatives have superior vasodilative based on the calcium entry blocking action and platelet aggregation inhibiting activities.

DETAILED DESCRIPTION OF THE PREFERRED EMBODIMENTS

In the 1,4-dihydropyridine derivatives having the above general formula (I), $Ar^1$ and $Ar^2$ may be an aromatic hydrocarbon group, which may have a substituent. Examples of the aromatic hydrocarbon group represented by either $Ar^1$ or $Ar^2$ are phenyl group and napthyl group, which may have a substituent.

$Ar^1$ and $Ar^2$ may also be an aromatic heterocyclic group, which may have a substituent. Examples of the aromatic heterocyclic group represented by $Ar^1$ or $Ar^2$ include pyridyl group, quinolyl group, isoquinolyl group, furyl group, thienyl group, benzoxazolyl group, benzothiazolyl group, pyridazinyl group, pyrazinyl group, pyrimidinyl group, indolyl group, benzoxadiazolyl group, benzothiadiazolyl group, which may have a substituent.

Examples of the substituent of the aromatic hydrocarbon group and the aromatic heterocyclic carbon group represented by either $Ar^1$ or $Ar^2$ include a halogen, cyano group, nitro group, trifluoromethyl group, trichloromethyl group, azide group, amide group, an alkyl group having 1 to 4 carbon atoms, an alkoxyl group having 1 to 4 carbon atoms, a benzoyl group, an alkylthio group having 1 to 4 carbon atoms, phenylthio group, phenoxy group, a lower alkoxycarbonyl group, a lower acyl group, benzyloxy group, hydroxy group, and cinnamyloxy group.

Specific examples of the group represented by either $Ar^1$ or $Ar^2$ include phenyl group, 2-nitrophenyl group, 3-nitro-phenyl group, 4-nitrophenyl group, 2-cyanophenyl group, 2-bromophenyl group, 3-bromophenyl group, 4-bromophenyl group, 2-chlorophenyl group, 3-chlorophenyl group, 4-chloro-phenyl group, 2-iodophenyl group, 3-iodophenyl group, 4-iodophenyl group, 3-cyanophenyl group, 4-cyanophenyl group, 2,3-dichlorophenyl group, 2,6-dichlorophenyl group, 3,5-dichlorophenyl group, 2-furyl group, furyl group, thienyl group, 3-thienyl group, 1-naphthyl group, naphthyl group, 3-azidophenyl group, 2-trifluoromethylphenyl group, 3-trifluoromethylphenyl group, 4-trifluoromethylphenyl group, 2-methylphenyl group, 3-methylphenyl group, 4-methylphenyl group, 2-hydroxyphenyl group, 3-hydroxyphenyl group, 4-hydroxyphenyl group, 2-benzyloxyphenyl group, 3-benzyloxyphenyl group, 2-cinnamyloxyphenyl group, 3-cinnamyloxyphenyl group, 3-benzoylphenyl group, 2-methoxyphenyl group, 3-methoxyphenyl group, 4-methoxyphenyl group, 4-methylthiophenyl group, 3-trichloromethylphenyl group, 2-pyridyl group, pyridyl group, 4-pyridyl group, quinolyl group, 3-quinolyl group, 4-quinolyl group, 1-isoquinolyl group, quinoxalyl group, 2-chloropyridyl group, 6-chloropyridyl group, 2-methylpyridyl group, 6-methylpyridyl group, 2-methoxypyridyl group, 6-methoxypyridyl group, 5-bromopyridyl group, 2-amionpyridyl group, 2-mercaptopyridyl group, pyridazinyl group, 4-pyridazinyl group, pyrazinyl group, pyrimidinyl group, 5-pyrimidyl group, 7-benzoxazolyl group, 7-benzothiazolyl group, 3-benzoxadiazolyl group, 3-benzothiazolyl group, 2-indolyl group, 3-indolyl group, and 5-indolyl group.

Further in the formula (I), $R^1$ is $-CO_2R^2$, $-SO_2R^3$, $-COR^4$, $-CON(R^5)_2$, $-CN$ or $-NO_2$.

$R^2$ in $-CO_2R^2$ represents (i) hydrogen, (ii) a straight chain, branched chain or cyclic saturated hydrocarbon group having 2 to 10 carbon atoms, which may have a substituent selected from the group consisting of an alkyl group having 1 to 4 carbon atoms, an alkoxyl group having 1 to 4 carbon atoms, a phenoxy group which may have a substituent, a phenylthio group which may have a substituent, a substituted amino group, a cyclic amino group which may have a substituent, a phenyl group which may have a substituent, an aromatic heterocyclic group which may have a substituent, and a trihalomethyl group, or (iii) a straight chain, branched chain or cyclic unsaturated hydrocarbon group having 2 to 10 carbon atoms, which may have a substituent selected from the group consisting of an alkyl group having 1 to 4 carbon atoms, an alkoxyl group having 1 to 4 carbon atoms, a phenoxy group which may have a substituent, a phenylthio group which may have a substituent, a substituted amino group, a cyclic amino group which may have a substituent, a phenyl group which may have a substituent, an aromatic heterocyclic group which may have a substituent, and a trihalomethyl group.

Examples of the straight chain or branched saturated hydrocarbon group represented by $R^2$ include methyl group, ethyl group, n-propyl group, n-butyl group, n-pentyl group, n-hexyl group, n-heptyl group, n-octyl group, n-nonyl group, n-decyl group, isoproyl group, and isobutyl group, which may have a substituent.

Examples of the cyclic hydrocarbon group represented by $R^2$ include cyclopentyl group and cyclohexyl group, which may have a substituent.

Examples of the unsaturated hydrocarbon group represented by $R^2$ include propenyl group, 2-butenyl group, 3-butenyl group, 2-pentenyl group, 2,4-hexadienyl group, 2,4-hexadiynyl group, hexa-4-en-2-yne, which may have a substituent.

Examples of the substituent of $R^2$ include an alkoxyl group having 1 to 6 carbon atoms, such as methoxy group, ethoxy group and propoxy group; an unsubstituted or substituted phenoxy group; an unsubstituted or substituted phenylthio group; a substituted amino group, such as dimethyl amino group, diethyl amino group, and N-benzyl-N-methylamino group; cyclic amino group, such as an unsubstituted or substituted piperazinyl group and piperidinyl group; an unsubstituted or substituted phenyl group; an unsubstituted or substituted aromatic heterocyclic group, such as pyridyl group, quinolyl group, isoquinolyl group, furyl group, thienyl group, benzoxazolyl group, benzothiazolyl group, pyridazinyl group, pyrazinyl group, pyrimidinyl group, indolyl group, benzoxadiazolyl group, and benzothiadiazolyl group; and a trihalomethyl group.

Specific examples of $R^2$ include hydrogen, methyl group, ethyl group, n-propyl group, n-butyl group, n-pentyl group, n-hexyl group, n-heptyl group, n-octyl group, n-nonyl group, n-decyl group, isopropyl group, isobutyl group, cyclopentyl group, cyclohexyl group, propenyl group, 2-propyne-1-yl group, (E)-2-butene-1-yl group, (E)-3-butene-1-yl group, E)-2-pentene-1-yl group, (2E,4E)-2,4-hexadienyl group, 2,4-hexadiynyl group, (E)-hexa-4-en-2-yne group, (E)-3-phenyl-2-propene-1-yl group, (Z)-3-phenyl-2-propene-1-yl group, 3-phenyl-2-propyne-1-yl group, (2E,4E)-5-phenyl-2,4-pentadiene-1-yl group, 5-phenyl-penta-2,4-diyne-1-yl group, (E)-5-phenyl-penta-2-en-4-yne-1-yl group, (E)-3-(3-(1-imidazolylmethyl)phenyl]-2-propene-1-yl group, (E)-3-(2-(1-imidazolylmethyl)phenyl]-2-propene-1-yl group, (E)-3-(4-(1-imidazolylmethyl)phenyl]-2-propene-1-yl group, (Z)-3-(4-(1-imidazolylmethyl)phenyl]-2-propene-1-yl group, (E)-3-(6-(1-imidazolylmethyl)-pyridine-2-yl]-2-propene-1-yl group, (E)-3-(5-(1-imidazolylmethyl)furan-2-yl]-2-propene-1-yl group, (E)-3-(5-(1-imidazolylmethyl)thiophene-2-yl]-2-propene-1-yl group, (E)-3-phenyl-1-methyl-2-propene-1-yl group, (E)-1-fluoro-3-phenyl-2-propene-1-yl group, 2-methoxyethyl group, 3-methoxypropyl group, 3-ethoxypropyl group, 2-phenoxyethyl group, 2-phenylthioethyl group, 2-(N-methylamino)ethyl group, 2-(N,N-dimethylamino)ethyl group, 2-(N-methyl-N-phenylamino)ethyl group, 2-(N,N-diethylamino)ethyl group, 2-(N-benzyl-N-methylamino)ethyl group, 2-(1-piperazinyl)ethyl group, 4-(1-piperazinyl)butyl group, 6-(1-piperazinyl)hexyl group, 2-(4-piperidinyl)ethyl group, 2-(4-phenylpiperazine-1-yl)ethyl group, 3-(4-phenylpiperazine-1-yl)propyl group, 4-(4-phenyl-piperazine-1-yl)butyl group, 6-(4-phenylpiperazine-1-yl)hexyl group, 2-(4-phenylpiperidine-1-yl)ethyl group, 3-(4-phenylpiperidine-1-yl)propyl group, 4-(4-phenylpiperidine-1-yl)butyl group, 3-(4-phenylpiperidine-1-yl)butyl group, 6-(4-phenylpiperidine-1-yl)exyl group, 2-(4-(diphenylmethyl)-piperazine-1-yl]ethyl group, 3-(4-(diphenylmethyl)-piperazine-1-yl)propyl group, 4-(4-(diphenylmethyl)-piperazine-1-yl)]butyl group, 6-(4-(diphenylmethyl)-piperazine-1-yl)]hexyl group, 2-morpholinoethyl group, N-benzylpyrrolidine-3-yl group, N-benzylpiperidine-3-yl group, 2-(1,2,3,4-tetrahydroisoquinoline-2-yl)ethyl group, 2,2,2-trifluoroethyl group, 2-(3,7-dihydro-3,7-dimethyl-1H-purine-2,6-dione-1-yl)ethyl group, and 2-(1,2,3,6-tetrahydro-1,3-dimethyl-2,6-dioxo-7H-purine-7-yl)ethyl group.

$R^3$ in $-SO R^3$ is an alkyl group having 1 to 4 carbon atoms. Specific examples of the alkyl group represented by $R^3$ include methyl group, ethyl group, n-propyl group, and isopropyl group.

$R^4$ in $-COR^4$ is a phenyl group or an alkyl group having 1 to 4 carbon atoms. Specific examples of the alkyl group represented by $R^4$ include methyl group, ethyl group, n-propyl group, and isopropyl group.

$R^5$ in —CON($R^5$) is an alkyl group having 1 to 4 carbon atoms. Specific examples of the alkyl group represented by $R^5$ is selected from the group consisting of methyl group, ethyl group, n-propyl group, and isopropyl group.

Specific examples of the 1,4-diphydropyridine derivatives having formula (I) according to the present invention are as follows:

methyl 1,4-dihydro-2,6-dimethyl-4-(3-nitrophenyl)-5-(2-pyridyl)pyridine-3-carboxylate,
methyl 1,4-dihydro-2,6-dimethyl-4-(3-nitrophenyl)-5-pyridylpyridine-3-carboxylate,
methyl 1,4-dihydro-2,6-dimethyl-4-(3-nitrophenyl)-5-(4-pyridyl)pyridine-3-carboxylate,
methyl 1,4-dihydro-2,6-dimethyl-4-(3-nitrophenyl)-5-pyrazinylpyridine-3-carboxylate,
methyl 1,4-dihydro-2,6-dimethyl-4-(3-nitrophenyl)-5-pyridazinylpyridine-3-carboxylate,
methyl 1,4-dihydro-2,6-dimethyl-4-(3-nitrophenyl)-5-4-pyridazinyl)pyridine-3-carboxylate,
methyl 1,4-dihydro-2,6-dimethyl-4-(3-nitrophenyl)-5-pyrimidylpyridine-3-carboxylate,
methyl 1,4-dihydro-2,6-dimethyl-4-(3-nitrophenyl)-5(5-pyrimidinyl)pyridine-3-carboxylate,
methyl 1,4-dihydro-2,6-dimethyl-4-(3-nitrophenyl)-5-quinolylpyridine-3-carboxylate,
methyl 1,4-dihydro-2,6-dimethyl-4-(3-nitrophenyl)-5(3-quinolyl)pyridine-3-carboxylate,
methyl 1,4-dihydro-2,6-dimethyl-4-(3-nitrophenyl)-5(4-quinolyl)pyridine-3-carboxylate,
methyl 1,4-dihydro-2,6-dimethyl-5-(1-isoquinolyl)-4-(4-nitrophenyl)pyridine-3-carboxylate,
methyl 1,4-dihydro-2,6-dimethyl-4-(3-nitrophenyl)-5-quinoxalylpyridine-3-carboxylate,
methyl 1,4-dihydro-2,6-dimethyl-5-(2-methoxyphenyl)-4(3-nitrophenyl)pyridine-3-carboxylate,
methyl 1,4-dihydro-2,6-dimethyl-5-(2-fluorophenyl)-4(3-nitrophenyl)pyridine-3-carboxylate,
methyl 1,4-dihydro-2,6-dimethyl-4-(3-nitrophenyl)-5-thienylpyridine-3-carboxylate,
methyl 1,4-dihydro-2,6-dimethyl-5-(2-furyl)-4-(3-nitrophenyl)pyridine-3-carboxylate,
methyl 1,4-dihydro-2,6-dimethyl-5-(2-methylpyridyl)-4(3-nitrophenyl)pyridine-3-carboxylate,
methyl 1,4-dihydro-2,6-dimethyl-5-(6-methylpyridyl)-4(3-nitrophenyl)pyridine-3-carboxylate,
methyl 1,4-dihydro-2,6-dimethyl-5-(2-methoxypyridyl)-4-(3-nitrophenyl)pyridine-3-carboxylate,
methyl 1,4-dihydro-2,6-dimethyl-5-(6-methoxypyridyl)-4(3-nitrophenyl)pyridine-3-carboxylate,
methyl 1,4-dihydro-2,6-dimethyl-5-(2-mercaptopyridyl)-4(3-nitrophenyl)pyridine-3-carboxylate,
methyl 5-(5-bromopyridyl)-1,4-dihydro-2,6-dimethyl-4-(3-nitrophenyl)pyridine-3-carboxylate,
methyl 5-(2-aminopyridyl)-1,4-dihydro-2,6-dimethyl-4-(3-nitrophenyl)pyridine-3-carboxylate,
methyl 5-(2-chloropyridyl)-1,4-dihydro-2,6-dimethyl-4-(3-nitrophenyl)pyridine-3-carboxylate,
methyl 5-(6-chloropyridyl)-1,4-dihydro-2,6-dimethyl-4-(3-nitrophenyl)pyridine-3-carboxylate,
methyl 4-(7-benzoxazolyl)-1,4-dihydro-2,6-dimethyl-5-pyridylpyridine-3-carboxylate,
methyl 4-(3-benzoxazolyl)-1,4-dihydro-2,6-dimethyl-5-pyridylpyridine-3-carboxylate,
methyl 4-(3-benzothiazolyl)-1,4-dihydro-2,6-dimethyl-5-pyridylpyridine-3-carboxylate,
methyl 1,4-dihydro-2,6-dimethyl-4-(2-indolyl)-5-pyridylpyridine-3-carboxylate,
methyl 1,4-dihydro-2,6-dimethyl-4-(3-indolyl)-5-pyridylpyridine-3-carboxylate,
methyl 1,4-dihydro-2,6-dimethyl-4-(5-indolyl)-5-pyridylpyridine-3-carboxylate,
methyl 4-(2-cyanophenyl)-1,4-dihydro-2,6-dimethyl-5-pyridylpridine-3-carboxylate,
methyl 1,4-dihydro-2,6-dimethyl-5-pyridyl-4-(2-trifluorophenyl)pyridine-3-carboxylate,
methyl 1,4-dihydro-2,6-dimethyl-5-pyridyl-4-(3-trifluorophenyl)pyridine-3-carboxylate,
methyl 1,4-dihydro-2,6-dimethyl-5-pyridyl-4-(4-trifluorophenyl)pyridine-3-carboxylate,
methyl 4-(2-bromophenyl)-1,4-dihydro-2,6-dimethyl-5-pyridylpyridine-3-carboxylate,
methyl 4-(3-bromophenyl)-1,4-dihydro-2,6-dimethyl-5-pyridylpyridine-3-carboxylate,
methyl 4-4-bromophenyl)-1,4-dihydro-2,6-dimethyl-5-pyridylpyridine-3-carboxylate,
methyl 4-(2-chlorophenyl)-1,4-dihydro-2,6-dimethyl-5-pyridylpyridine-3-carboxylate,
methyl 4-(3-chlorophenyl)-1,4-dihydro-2,6-dimethyl-5-pyridylpyridine-3-carboxylate,
methyl 4-(4-chlorophenyl)-1,4-dihydro-2,6-dimethyl-5-pyridylpyridine-3-carboxylate,
methyl 4-(2,3-dichlorophenyl)-1,4-dihydro-2,6-dimethyl-5-pyridylpyridine-3-carboxylate,
methyl 4-(2,6-dichlorophenyl)-1,4-dihydro-2,6-dimethyl-5-pyridylpyridine-3-carboxylate,
methyl 4-(3,5-dichlorophenyl)-1,4-dihydro-2,6-dimethyl-5-pyridylpyridine-3-carboxylate,
methyl 1,4-dihydro-2,6-dimethyl-4-(2-furyl)-5-pyridylpyridine-3-carboxylate,
methyl 1,4-dihydro-2,6-dimethyl-4-furyl-5-pyridylpyridine-3-carboxylate,
methyl 1,4-dihydro-2,6-dimethyl-5-pyridyl-4-thienylpyridine-3-carboxylate,
methyl 1,4-dihydro-2,6-dimethyl-5-pyridyl-4-(3-thienyl)-pyridine-3-carboxylate,
methyl 1,4-dihydro-2,6-dimethylpyridine-4,5-dipyridyl-3carboxylate,
methyl 1,4-dihydro-2,6-dimethyl-5-pyridyl-4-(4-quinolyl)- 1-pyridine-3-carboxylate,
3-cyano-1,4-dihydro-2,6-dimethyl-4-(3-nitrophenyl)-5-pyridylpyridine,
3-benzoyl-1,4-dihydro-2,6-dimethyl-4-(3-nitrophenyl)-5-pyridylpyridine,
3-acetyl-1,4-dihydro-2,6-dimethyl-4-(3-nitrophenyl)-5-pyridylpyridin
methyl 4-(3-azidophenyl)-1,4-dihydro-2,6-dimethyl-5-pyridylpyridine-3-carboxylate,
methyl 1,4-dihydro-2,6-dimethyl-4-(1-naphthyl)-5-pyridylpyridine-3-carboxylate,
methyl 1,4-dihydro-2,6-dimethyl-4-naphthyl-5-pyridylpyridine-3-carboxylate,
methyl 1,4-dihydro-2,6-dimethyl-4-(2-iodophenyl)-5-pyridylpyridine-3-carboxylate,
methyl 1,4-dihydro-2,6-dimethyl-4-(3-iodophenyl)-5-pyridylpyridine-3-carboxylate,
methyl 1,4-dihydro-2,6-dimethyl-4-(4-iodophenyl)-5-pyridylpyridine-3-carboxylate,
1,4-dihydro-2,6-dimethyl-4-(3-methylphenyl)-5-pyridylpyridine-3-carboxylate,
methyl 1,4-dihydro-2,6-dimethyl-4-(4-methylphenyl)-5-pyridylpyridine-3-carboxylate,
methyl 1,4-dihydro-2,6-dimethyl-4-(2-methoxylphenyl)-5-pyridylpyridine-3-carboxylate,
methyl 1,4-dihydro-2,6-dimethyl-4-3-methoxylphenyl)-5-pyridylpyridine-3-carboxylate, methyl 1,4-dihydro-2,6-dimethyl-4-(4-methoxyphenyl)-5-pyridylpyridine-3-carboxylate,
methyl 1,4-dihydro-2,6-dimethyl-4-(4-methylthiophenyl)-5-pyridylpyridine-3-carboxylate,
ethyl 1,4-dihydro-2,6-dimethyl-4-(3-nitrophenyl)-5-pyridylpyridine-3-carboxylate,
isopropyl 1,4-dihydro-2,6-dimethyl-4-(3-nitrophenyl)-5-pyridylpyridine-3-carboxylate,
n-hexyl 1,4-dihydro-2,6-dimethyl-4-(3-nitrophenyl)-5-pyridylpyridine-3-carboxylate,
cyclohexyl 1,4-dihydro-2,6-dimethyl-4-(3-nitrophenyl)-5-pyridylpyridine-3-carboxylate,
2-methoxyethyl 1,4-dihydro-2,6-dimethyl-4-(3-nitrophenyl)-5-pyridylpyridine-3-carboxylate,
2-phenoxyethyl 1,4-dihydro-2,6-dimethyl-4-(3-nitrophenyl)-5-pyridylpyridine-3-carboxylate,
2-phenoxyethyl 1,4-dihydro-2,6-dimethyl-4-(3-nitrophenyl)-5-(4-pyridyl)pyridine-3-carboxylate,
2-(phenylthio)ethyl 1,4-dihydro-2,6-dimethyl-4-(3-nitrophenyl)-5-pyridylpyridine-3-carboxylate,
2-pentene-1-ol 1,4-dihydro-2,6-dimethyl-4-(3-nitrophenyl)-5(4-pyridyl)pyridine-3-carboxylate,
2-propyne-1-yl 1,4-dihydro-2,6-dimethyl-4-(3-nitrophenyl)-5-pyridylpyridine-3-carboxylate,
(2E,4E)-2,4-hexadiene-1-yl 1,4-dihydro-2,6-dimethyl-4-(3-nitrophenyl)-5-pyridylpyridine-3-carboxylate,
2,4-hexadiyne-1-yl 1,4-dihydro-2,6-dimethyl-4-(3-nitrophenyl)-5-pyridylpyridine-3-carboxylate,
(E)-3-phenyl-2-propene-1-yl 1,4-dihydro-2,6-dimethyl-4-(3-nitrophenyl)-5-pyridylpyridine-3-carboxylate,
(E)-3-phenyl-2-propene-1-yl 1,4-dihydro-2,6-dimethyl-4-(3-nitrophenyl)-5-(4-pyridyl)pyridylpyridine-3carboxylate,
(Z)-3-phenyl-2-propene-1-yl 1,4-dihydro-2,6-dimethyl-4-(3-nitrophenyl)-5-pyridylpyridine-3-carboxylate,
(2E,4E)-5-phenyl-2,4-pentadiene-1-yl 1,4-dihydro-2,6-dimethyl-4-(3-nitrophenyl)-5-pyridylpyridine-3carboxylate,
5-phenyl-penta-2,4-diyne-1-yl 1,4-dihydro-2,6-dimethyl-4-(3-nitrophenyl)-5-pyridylpyridine-3-carboxylate,
(E)-5-phenyl-penta-2-ene-4-yne-1-yl 1,4-dihydro-2,6-dimethyl-4-(3-nitrophenyl)-5-pyridylpyridine-3-carboxylate,
(E)-3-(4-(1-imidazolylmethyl)phenyl-2-propene-1-yl 1,4-dihydro-2,6-dimethyl-4-(3-nitrophenyl)-5-pyridylpyridine-3-carboxylate,
(E)-3-(4-(1-imidazolylmethyl)phenyl-2-propene-1-yl 1,4-dihydro-2,6-dimethyl-5-(2-furyl)-4-(3-nitrophenyl)-pyridine-3-carboxylate,
(Z)-3-(4-(1-imidazolylmethyl)phenyl]-2-propene-1-yl 1,4-dihydro-2,6-dimethyl-4-(3-nitrophenyl)-5-pyridylpyridine-3-carboxylate,
(E)-3-(6-(1-imidazolylmethyl)pyridine-2-yl]-2-propene-1-yl 1,4-dihydro-2,6-dimethyl-4-(3-nitrophenyl)-5-pyridylpyridine-3-carboxylate,
(E)-3-(5-(1-imidazolylmethyl)furan-2-yl]-2-propene-1-yl 1,4-dihydro-2,6-dimethyl-4-(3-nitrophenyl)-5-pyridylpyridine-3-carboxylate,
(E)-3-(5-(1-imidazolylmethyl)thiophene-2-yl]-2-propene-1-yl 1,4-dihydro-2,6-dimethyl-4-(3-nitrophenyl)-5-pyridylpyridine-3-carboxylate,
2-(N-benzyl-N-methylamino)ethyl 1,4-dihydro-2,6-dimethyl-4-(3-nitrophenyl)-5-pyridylpyridine-3-carboxylate,
2-(N-benzyl-N-methylamino)ethyl 1,4-dihydro-2,6-dimethyl-4-(3-nitrophenyl)-5-(4-pyridyl)pyridine-3-carboxylate,
2-(4-phenylpiperazine-1-yl)ethyl 1,4-dihydro-2,6-dimethyl-4-(3-nitrophenyl)-5-pyridylpyridine-3-carboxylate,
2-(4-phenylpiperazine-1-yl)ethyl 1,4-dihydro-2,6-dimethyl-4-(3-nitrophenyl)-5-(4-pyridyl)pyridine-3-carboxylate,
2-(4-phenylpiperidine-1-yl)ethyl 1,4-dihydro-2,6-dimethyl-4-(3-nitrophenyl)-5-pyridylpyridine-3-carboxylate,
2-[4-(diphenylmethyl)piperazine-1-yl]ethyl 1,4-dihydro-2,6-dimethyl-4-(3-nitrophenyl)-5-pyridylpyridine-3-carboxylate
2-(1,2,3,4-tetrahydroisoquinoline-2-yl)ethyl 1,4-dihydro-2,6-dimethyl-4-(3-nitrophenyl)-5-pyridylpyridine-3carboxylate,
2,2,2-trifluoroethyl 1,4-dihydro-2,6-dimethyl-4-(3-nitrophenyl)-5-pyridylpyridine-3-carboxylate,
2-(3,7-dihydro-3,7-dimethyl-1H-purine-2,6-dione-1-yl)ethyl 1,4-dihydro-2,6-dimethyl-4-(3-nitrophenyl)-5-pyridylpyridine-3-carboxylate,
2-(1,2,3,6-tetrahydro-1,3-dimethyl-2,6-dioxo-7H-purine-7-yl)ethyl
3-cyano-1,4-dihydro-2,6-dimethyl-4-(3-nitrophenyl)-5-pyridylpyridine-3-carboxylate, (2-pyridyl)pyridine,
N,N-diethyl-1,4-dihydro-2,6-dimethyl-4-(3-nitrophenyl)-5-(2-pyridyl)pyridine-3-carboxamide,
3-benzoyl-1,4-dihydro-2,6-dimethyl-4-(3-nitrophenyl)-5-(2-pyridyl)pyridine,
3-acetyl-1,4-dihydro-2,6-dimethyl-4-(3-nitrophenyl)-5-(2-pyridyl)pyridine,
1,4-dihydro-2,6-dimethyl-3-nitro-4-(3-nitrophenyl)-5-(2-pyridyl)pyridine,
methyl 1,4-dihydro-2,6-dimethyl-4-(3-nitrophenyl)-5-(2-pyridyl)pyridine-3-sulfinate, and
2,2,3-trifluoroethyl 1,4-dihydro-2,6-dimethyl-4-(3-nitrophenyl)-5-(2-pyridyl)pyridine-3-carboxylate.

1,4-dihydropryridine derivatives having formula (I) according to the present invention can be prepared by either Process 1 or Process 2 as shown below:

Process 1

Compounds having formula I-1):

$$CH(Ar^2)=C(Ar^1)-C(CH_3)=O \qquad (I\text{-}1)$$

are allowed to react with compounds having formula (I-2):

$$CH_3-C(NH_2)=CHR^1 \qquad (I\text{-}2)$$

wherein $R^1$, $Ar^1$ and $Ar^2$ are the same as those defined previously in formula (I).

Examples of the compounds having formula (I-1) are as follows:
4-(2-nitrophenyl)-3-pyridyl-3-butene-2-one,
4-(3-nitrophenyl)-3-pyridyl-3-butene-2-one,
4-(4-nitrophenyl)-3-pyridyl-3-butene-2-one,
4-(2-nitrophenyl)-3-(2-pyridyl)-3-butene-2-one,
4-(3-nitrophenyl)-3-(2-pyridyl)-3-butene-2-one,
4-(4-nitrophenyl)-3-(2-pyridyl)-3-butene-2-one,
4-(2-nitrophenyl)-3-(4-pyridyl)-3-butene-2-one,
4-(3-nitrophenyl)-3-(4-pyridyl)-3-butene-2-one,
4-(4-nitrophenyl)-3-(4-pyridyl)-3-butene-2-one,
4-(2-cyanophenyl)-3-pyridyl-3-butene-2-one,
4-(3-cyanophenyl)-3-pyridyl-3-butene-2-one,
4-(4-cyanophenyl)-3-pyridyl-3-butene-2-one,
4-(2,3-dichlorophenyl)-3-pyridyl-3-butene-2-one,
4-(3,5-dichlorophenyl)-3-pyridyl-3-butene-2-one, 4-(2,6-dichlorophenyl)-3-pyridyl-3-butene-2-one,
3-pyridyl-4-(2-trifluoromethylphenyl)-3-butene-2-one,
3-pyridyl-4-(3-trifluoromethylphenyl)-3-butene-2-one,
3-pyridyl-4-(4-trifluoromethylphenyl)-3-butene-2-one,
4-(2-furyl)-3-pyridyl-3-butene-2-one,
4-furyl-3-pyridyl-3-butene-2-one,
3-pyridyl-4-thienyl-3-butene-2-one,
3-pyridyl-4-(3-thienyl)-3-butene-2-one,
3-pyridyl-4-quinolyl-3-butene-2-one,
3-pyridyl-4-(3-quinolyl)-3-butene-2-one,
3-pyridyl-4-(4-quinolyl))-3-butene-2-one,
4-(2-methoxyphenyl)-3-(2-pyridyl)-3-butene-2-one,
4-(3-methoxyphenyl)-3-(2-pyridyl)-3-butene-2-one,
4-(4-methoxyphenyl)-3-(2-pyridyl)-3-butene-2-one,
4-(3-nitrophenyl)-3-pyrazinyl-3-butene-2-one,
4-(3-nitrophenyl)-3-pyrimidinyl-3-butene-2-one,
4-(3-nitrophenyl)-3-(5-pyrimidinyl)-3-butene-2-one,
4-(3-nitrophenyl)-3-(3-quinolyl)-3-butene-2-one,
4-(3-nitrophenyl)-3-(4-quinolyl)-3-butene-2-one,
3-(1-isoquinolyl)-4-(3-nitrophenyl)-3-butene-2-one,
4-(2-pyridyl)-3-pyridyl-3-butene-2-one,
3,4-dipyridyl-3-butene-2-one,
4-(4-pyridyl)-3-pyridyl-3-butene-2-one,
4-(3-nitrophenyl)-3-quinoxalyl-3-butene-one,
3-(2-methylpyridyl)-4-(3-nitrophenyl))-3-butene-2-one,
3-(6-methylpyridyl)-4-(3-nitrophenyl))-3-butene-2-one,
3-(2-methoxypyridyl)-4-(3-nitrophenyl)-3-butene-2-one,
3-(6-methoxypyridyl)-4-(3-nitrophenyl)-3-butene-2-one,
3-(5-bromopyridyl)-4-(3-nitrophenyl)-3-butene-2-one,
3-(2-aminopyridyl)-4-(3-nitrophenyl)-3-butene-2-one,
3-(2-mercaptopyridyl)-4-(3-nitrophenyl)-3-butene-2-one,
3-(7-benzoxazolyl)-4-(3-nitrophenyl)-3-butene-2-one,
3-(7-benzothiazolyl)-4-(3-nitrophenyl)-3-butene-2-one,
3-(7-benzoxyathiazolyl)-4-(3-nitrophenyl)-3-butene-2-one,
3-(3-benzothiadiazolyl)-4-(3-nitrophenyl)-3-butene-2-one,
3-(2-indolyl)-4-(3-nitrophenyl)-3-butene-2-one,
3-(3-indolyl)-4-(3-nitrophenyl)-3-butene-2-one,
3-(5-indolyl)-4-(3-nitrophenyl)-3-butene-2-one,
4-(3-nitrophenyl)-3-pyridazinyl-3-butene-2-one,
4-(3-nitrophenyl)-3-quinolyl-3-butene-2-one,
3-(2-furyl)-4-(3-nitrophenyl)-3-butene-2-one,
3-(2-methoxyphenyl)-4-(3-nitrophenyl)-3-butene-2-one,
3-(2-fluorophenyl)-4-(3-nitrophenyl)-3-butene-2-one,
3-(2-chloropyridyl)-4-(3-nitrophenyl)-3-butene-2-one,
3-(6-chloropyridyl)-4-(3-nitrophenyl)-3-butene-2-one,
3-(5-isoquinolyl)-4-(3-nitrophenyl)-3-butene-2-one,
4-(3-nitrophenyl)-3-thienyl-3-butene-2-one,
4-(1-naphthyl)-3-pyridyl-3-butene-2-one,
4-naphthyl-3-pyridyl-3-butene-2-one,
4-(3-azidophenyl)-3-pyridyl-3-butene-2-one,
4-(2-methylphenyl)-3-pyridyl-3-butene-2-one,
4-(3-methylphenyl)-3-pyridyl-3-butene-2-one,
4-(4-methylphenyl)-3-pyridyl-3-butene-2-one,
4-(2-chlorophenyl)-3-pyridyl-3-butene-2-one,
4-(2-bromophenyl)-3-pyridyl-3-butene-2-one,
4-(3-bromophenyl)-3-pyridyl-3-butene-2-one,
4-(4-bromophenyl)-3-pyridyl-3-butene-2-one,
4-(2-iodophenyl)-3-pyridyl-3-butene-2-one,
4-(3-iodophenyl)-3-pyridyl-3-butene-2-one,
4-(4-iodophenyl)-3-pyridyl-3-butene-2-one,
4-(1-isoquinolyl)-3-pyridyl-3-butene-2-one,
4-(5-isoquinolyl)-3-pyridyl-3-butene-2-one,
4-(2-hydroxyphenyl)-3-pyridyl-3-butene-2-one,
4-(3-hydroxyphenyl)-3-pyridyl-3-butene-2-one,
4-(4-hydroxyphenyl)-3-pyridyl-3-butene-2-one,
4-(2-benzyloxyphenyl)-3-pyridyl-3-butene-2-one,
4-(3-benzyloxyphenyl)-3-pyridyl-3-butene-2-one,
4-(4-benzyloxyphenyl)-3-pyridyl-3-butene-2-one,
4-(2-cinnamyloxyphenyl)-3-pyridyl-3-butene-2-one,
4-(3-cinnamyloxyphenyl)-3-pyridyl-3-butene-2-one,
4-4-cinnamyloxyphenyl)-3-pyridyl-3-butene-2-one, and
4-(3-benzoylphenyl)-3-pyridyl-3-butene-2-one.

Examples of the compounds having formula (I-2) are as follows:
methyl 3-aminocrotonate,
ethyl 3-aminocrotonate,
n-propyl 3-aminocrotonate,
n-butyl 3-aminocrotonate,
n-pentyl 3-aminocrotonate,
n-hexyl 3-aminocrotonate,
n-heptyl 3-aminocrotonate,
n-octyl 3-aminocrotonate,
n-nonyl 3-aminocrotonate,
n-decyl 3-aminocrotonate,
isopropyl 3-aminocrotonate,
isobutyl 3-aminocrotonate,
cyclopentyl 3-aminocrotonate,
cyclohexyl 3-aminocrotonate,
propene-1-yl 3-aminocrotonate,
2-propyne-1-yl 3-aminocrotonate,
(E)-2-butene-1-yl 3-aminocrotonate,
(E)-3-butene-1-yl 3-aminocrotonate,
(E)-2-pentene-1-yl 3-aminocrotonate,
(2E,4E)-2,4-hexadienyl 3-aminocrotonate,
2,4-hexadienyl 3-aminocrotonate,
(E)-hexa-4-en-2-yne 3-aminocrotonate,
(E)-3-phenyl-2-propene-1-yl 3-aminocrotonate,
(Z)-3-phenyl-2-propene-1-yl 3-aminocrotonate,
3-phenyl-2-propyne-1-yl 3-aminocrotonate,
(2E,4E)-5-phenyl-2,4-pentadiene-1-yl 3-aminocrotonate,
5-phenyl-penta-2,4-diyne-1-yl 3-aminocrotonate,
(E)-5-phenyl-penta-2-ene-4-yn-1-yl 3-aminocrotonate,
(E)-3-(4-(1-imidazolylmethyl)phenyl]-2-propene-1-yl 3-aminocrotonate,
(E)-3-(3-(1-lmidazolylmethyl)phenyl]-2-propene-1-yl 3-aminocrotonate,
(E)-3-(2-(1-imidazolylmethyl)phenyl]-2-propene-1-yl 3-aminocrotonate,
(Z)-3-(4-(1-imidazolylmethyl)phenyl]-2-propene-1-yl 3-aminocrotonate,
(E)-3-(6-(1-imidazolylmethyl)pyridine-2-yl]-2-propene-1-yl 3-aminocrotonate,
(E)-3-(5-(1-imidazolylmethyl)furan-2-yl]-2-propene-1-yl 3-aminocrotonate,
(E)-3-(5-(1-imidazolylmethyl)thiophene-2-yl]-2-propene-1-yl 3-aminocrotonate,
(E)-3-phenyl-1-methyl-2-propene-1-yl 3-aminocrotonate,
(E)-1-fluoro-3-phenyl-2-propene-1-yl 3-aminocrotonate,
2-methoxyethyl 3-aminocrotonate,
3-methoxypropyl 3-aminocrotonate,
3-ethoxypropyl 3-aminocrotonate,
2-phenoxyethyl 3-aminocrotonate,
2-phenylthioethyl 3-aminocrotonate,
2-(N-methylamino)ethyl 3-aminocrotonate,
2-(N,N-dimethylamino)ethyl 3-aminocrotonate,
2-(N-methyl-N-phenylamino)ethyl 3-aminocrotonate,
2-(N,N-diethylamino)ethyl 3-aminocrotonate,
2-(N-benzyl-N-methylamino)ethyl 3-aminocrotonate,
2-(1-piperazinyl)ethyl 3-aminocrotonate,
4-(1-piperazinyl)butyl 3-aminocrotonate, 6-(1-piperazinyl)hexyl 3-aminocrotonate,
2-(4-phenylpiperazine-1-yl)ethyl 3-aminocrotonate,
3-(4-phenylpiperazine-1-yl)propyl 3-aminocrotonate,
4-(4-phenylpiperazine-1-yl)butyl 3-aminocrotonate,
6-(4-phenylpiperazine-1-yl)hexyl 3-aminocrotonate,
2-(4-phenylpiperidine-1-yl)ethy 3-aminocrotonate,
3-(4-phenylpiperidine-1-yl)propyl 3-aminocrotonate,
4-(4-phenylpiperidine-1-yl)butyl 3-aminocrotonate,
6-(4-phenylpiperidine-1-yl)hexyl 3-aminocrotonate,
2-[4-(diphenylmethyl)piperazine-1-yl]ethyl 3-aminocrotonate,
3-[4-(diphenylmethyl)piperazine-1-yl]propyl 3-aminocrotonate,
4-(4-(diphenylmethyl)piperazine-1-yl]butyl 3-aminocrotonate,
2-morpholinoethyl 3-aminocrotonate,
N-benzylpyrrolidine-3-yl 3-aminocrotonate,
N-benzylpiperiridine-3-yl 3-aminocrotonate,
2-(1,2,3,4-tetrahyisoquinoline-2-yl)ethyl 3-aminocrotonate,
2,2,2-trifluoroethyl 3-aminocrotonate,
2-(3,7-dihydro-3,7-dimethyl-1H-purine-2,6-dione-1-yl)ethyl 3-aminocrotonate,
2-(1,2,3,6-tetrahydro-1,3-dimethyl-2,6-dioxo-7H-purine-7-yl) ethyl 3-aminocrotonate,
3-aminocrotonitrile,
N,N-diethyl 3-amino-2-butene amide,
3-amino-1-phenyl-2-butene-1-one,
4-amino-3-pentene-2-one,
2-amino-1-nitro-1-propene, and
methyl 3-amino-3-propene sulfinate.

The reaction can be carried out without any solvents, or in an inactive solvent such as tetrahydrofuran, 1,4-dioxane, benzene, toluene, methanol, ethanol, n-propanol, isopropanol, dimethyl sulfoxide, and dimethylformamide at temperatures of 50° C. to 150° C.

Process 2

Carboxylic acid derivatives having formula (I-3)

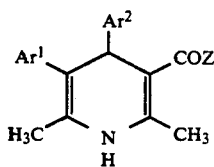

are allowed to react with alcohol derivatives having formula (I-4)

   (I-4)

wherein $R^2$, $Ar^1$ and $Ar^2$ are the same as those defined previously in formula (I), and Z is a hydroxyl group, a halogen, or an active ester moiety such as a methanesulfonyloxy group, a benzotriazol-1-oxy group, or a succinimide group.

The above carboxylic acid derivatives of formula (I-3) can be prepared without difficulty as will be described later.

Examples of the carboxylic acid derivatives of formula (I-3) are as follows:
1,4-dihydro-2,6-dimethyl-4-(3-nitrophenyl)-5-pyridylpyridine-3-carboxylic acid chloride,
1,4-dihydro-2,6-dimethyl-4-(3-nitrophenyl)-5-(2-pyridyl)pyridine-3-carboxylic acid,
1,4-dihydro-2,6-dimethyl-4-(3-nitrophenyl)-5-pyridylpyridine-3-carboxylic acid,
1,4-dihydro-2,6-dimethyl-4-(3-nitrophenyl)-5-(4-pyridyl)pyridine-3-carboxylic acid,
1,4-dihydro-2,6-dimethyl-4-(3-nitrophenyl)-5-pyrazinylpyridine-3-carboxylic acid,
1,4-dihydro-2,6-dimethyl-4-(3-nitrophenyl)-5-pyridazinylpyridine-3-carboxylic acid,
1,4-dihydro-2,6-dimethyl-4-(3-nitrophenyl)-5-(4-pyridazinyl)pyridine-3-carboxylic acid,
1,4-dihydro-2,6-dimethyl-4-(3-nitrophenyl)-5-pyrimidylpyridine-3-carboxylic acid,
1,4-dihydro-2,6-dimethyl-4-(3-nitrophenyl)-5-(5-pyrimidyl)pyridine-3-carboxylic acid,
1,4-dihydro-2,6-dimethyl-4-(3-nitrophenyl)-5-quinolylpyridine-3-carboxylic acid,
1,4-dihydro-2,6-dimethyl-4-(3-nitrophenyl)-5-(3-quinolyl)pyridine-3-carboxylic acid,
1,4-dihydro-2,6-dimethyl-4-(3-nitrophenyl)-5-(2-pyridyl)pyridine-3-carboxylic acid,
1,4-dihydro-2,6-dimethyl-4-(3-nitrophenyl)-5-(4-quinolyl)pyridine-3-carboxylic acid,
1,4-dihydro-2,6-dimethyl-5-(1-isoquinolyl)-4-(3-nitrophenyl)pyridine-3-carboxylic acid,
1,4-dihydro-2,6-dimethyl-4-(3-nitrophenyl)-5-quinoxalylpyridine-3-carboxylic acid,
1,4-dihydro-2,6-dimethyl-5-(2-methylpyridyl)-4-(3-nitrophenyl)-pyridine-3-carboxylic acid,
1,4-dihydro-2,6-dimethyl-5-(6-methylpyridyl)-4-(3-nitrophenyl)pyridine-3-carboxylic acid,
1,4-dihydro-2,6-dimethyl-5-(2-methoxypyridyl)-4-(3-nitrophenyl)pyridine-3-carboxylic acid,
1,4-dihydro-2,6-dimethyl-5-(6-methoxypyridyl)-4-(3-nitrophenyl)pyridine-3-carboxylic acid,
1,4-dihydro-2,6-dimethyl-5-(2-mercaptopyridyl)-4-(3-nitrophenyl)pyridine-3-carboxylic acid,
5-(5-bromopyridyl)-1,4-dihydro-2,6-dimethyl-4-(3-nitrophenyl)pyridine-3-carboxylic acid,
5-(2-aminopyridyl)-1,4-dihydro-2,6-dimethyl-4-(3-nitrophenyl)pyridine-3-carboxylic acid,
5-(2-chloropyridyl)-1,4-dihydro-2,6-dimethyl-4-(3-nitrophenyl)pyridine-3-carboxylic acid,
5-(6-chloropyridyl)-1,4-dihydro-2,6-dimethyl-4-(3-nitrophenyl)pyridine-3-carboxylic acid,
4-(7-benzoxazolyl)-1,4-dihydro-2,6-dimethyl-5-pyridylpyridine-3-carboxylic acid,
4-(7-benzothiazolyl)-1,4-dihydro-2,6-dimethyl-5-pyridylpyridine-3-carboxylic acid,
4-(3-benzoxazolyl)-1,4-dihydro-2,6-dimethyl-5-pyridylpyridine-3-carboxylic acid,
4-(3-benzothiazolyl)-1,4-dihydro-2,6-dimethyl-5-pyridylpyridine-3-carboxylic acid,
1,4-dihydro-2,6-dimethyl-4-(2-indolyl)-5-pyridylpyridine-3-carboxylic acid,
1,4-dihydro-2,6-dimethyl-4-(3-indolyl)-5-pyridylpyridine-3-carboxylic acid,
1,4-dihydro-2,6-dimethyl-4-(5-indolyl)-5-pyridylpyridine-3-carboxylic acid,
4-(2-cyanophenyl)-1,4-dihydro-2,6-dimethyl-5-pyridylpyridine-3-carboxylic acid,
1,4-dihydro-2,6-dimethyl-5-pyridyl-4-(2-trifluoromethylphenyl)pyridine-3-carboxylic acid,
1,4-dihydro-2,6-dimethyl-5-pyridyl-4-(3-trifluoromethylphenyl)pyridine-3-carboxylic acid,
1,4-dihydro-2,6-dimethyl-5-pyridyl-4-(4-trifluoromethylphenyl)pyridine-3-carboxylic acid,
4-(2-bromophenyl)-1,4-dihydro-2,6-dimethyl-5-pyridylpyridine-3-carboxylic acid,
4-(3-bromophenyl)-1,4-dihydro-2,6-dimethyl-5-pyridylpyridine-3-carboxylic acid, 4-(4-bromophenyl)-1,4-dihydro-2,6-dimethyl-5-pyridyl-pyridine-3-carboxylic acid,
4-(2-chlorophenyl)-1,4-dihydro-2,6-dimethyl-5-pyridyl-pyridine-3-carboxylic acid,
4-(3-chlorophenyl)-1,4-dihydro-2,6-dimethyl-5-pyridyl-pyridine-3-carboxylic acid,
4-(4-chlorophenyl)-1,4-dihydro-2,6-dimethyl-5-pyridyl-pyridine-3-carboxylic acid,
4-(2,3-dichlorophenyl)-1,4-dihydro-2,6-dimethyl-5-pyridylpyridine-3-carboxylic acid,
4-(2,6-dichlorophenyl)-1,4-dihydro-2,6-dimethyl-5-pyridylpyridine-3-carboxylic acid,
4-(3,5-dichlorophenyl)-1,4-dihydro-2,6-dimethyl-5-pyridylpyridine-3-carboxylic acid,
1,4-dihydro-2,6-dimethyl-4-2-furyl)-5-pyridylpyridine-3carboxylic acid,
1,4-dihydro-2,6-dimethyl-4-furyl)-5-pyridylpyridine-3-carboxylic acid,
1,4-dihydro-2,6-dimethyl-5-pyridyl-4-thienylpyridine-3-carboxylic acid,
1,4-dihydro-2,6-dimethyl-5-pyridyl-4-(3-thienyl)pyridine-3-carboxylic acid,
4-(3-azidophenyl)-1,4-dihydro-2,6-dimethyl-5-pyridylpyridine-3-carboxylic acid,
1,4-dihydro-2,6-dimethyl-4-(1-naphthyl)-5-pyridylpyridine-3-carboxylic acid,
1,4-dihydro-2,6-dimethyl-4-naphthyl-5-pyridylpyridine-3-carboxylic acid,
1,4-dihydro-2,6-dimethyl-4-(2-iodophenyl)-5-pyridylpyridine-3-carboxylic acid,
1,4-dihydro-2,6-dimethyl-4-(3-iodophenyl)-5-pyridylpyridine-3-carboxylic acid,
1,4-dihydro-2,6-dimethyl-4-(4-iodophenyl)-5-pyridylpyridine-3-carboxylic acid,
1,4-dihydro-2,6-dimethyl-4-(2-methylphenyl)-5-pyridylpyridine-3-carboxylic acid,
1,4-dihydro-2,6-dimethyl-4-(3-methylphenyl)-5-pyridylpyridine-3-carboxylic acid,
1,4-dihydro-2,6-dimethyl-4-(4-methylphenyl)-5-pyridylpyridine-3-carboxylic acid,
1,4-dihydro-2,6-dimethyl-4-(2-methoxyphenyl)-5-pyridylpyridine-3-carboxylic acid,
1,4-dihydro-2,6-dimethyl-4-(3-methoxyphenyl)-5-pyridylpyridine-3-carboxylic acid,
1,4-dihydro-2,6-dimethyl-4-(4-methoxyphenyl)-5-pyridylpyridine-3-carboxylic acid,
1,4-dihydro-2,6-dimethyl-4-(4-methylthiophenyl)-5-pyridylpyridine-3-carboxylic acid,
1,4-dihydro-2,6-dimethyl-4-(2-hydroxyphenyl)-5-pyridylpyridine-3-carboxylic acid,
1,4-dihydro-2,6-dimethyl-4-(3-hydroxyphenyl)-5-pyridylpyridine-3-carboxylic acid,
1,4-dihydro-2,6-dimethyl-4-4-hydroxyphenyl)-5-pyridylpyridine-3-carboxylic acid,
4-(2-benzyloxyphenyl)-1,4-dihydro-2,6-dimethyl-5-pyridylpyridine-3-carboxylic acid,
4-(4-benzyloxyphenyl)-1,4-dihydro-2,6-dimethyl-5-pyridylpyridine-3-carboxylic acid,
4-(2-cinnamyloxyphenyl)-1,4-dihydro-2,6-dimethyl-5-pyridylpyridine-3-carboxylic acid,
4-(3-cinnamyloxyphenyl)-1,4-dihydro-2,6-dimethyl-5-pyridylpyridine-3-carboxylic acid,
4-(4-cinnamyloxyphenyl)-1,4-dihydro-2,6-dimethyl-5-pyridylpyridine-3-carboxylic acid, and
4-(3-benzoylphenyl)-1,4-dihydro-2,6-dimethyl-5-pyridylpyridine-3-carboxylic acid.

The alcohol derivatives having formula (I-4) can be prepared without difficulty by using compounds which are easily available industriously, Examples of the alcohol derivatives are as follows: methyl alcohol, ethyl alcohol, n-propyl alcohol, n-butyl alcohol, n-pentyl alcohol, n-hexyl alcohol, n-heptyl alcohol, n-octyl alcohol, n-nonyl alcohol, n-decyl alcohol, isopropyl alcohol, isobutyl alcohol, cyclopentyl alcohol, cyclohexyl alcohol, 2-propyne-1-ol, (E)-2-butene-1-ol, (E)-3-butene-1-ol, (E)-2-pentene-1-ol, (2E,4E)-2,4-hexadiene-1-ol, 2,4-hexadiene-1-ol, (E)-hexa-4-ene-2-yne-1-ol, (E)-3-phenyl-2-propene-1-ol, (Z)-3-phenyl-2-propene-1-ol, 3-phenyl-2-propyne-1-ol, (2E,4E)-5-phenyl-2,4-pentadiene-1-ol, 5-phenyl-2,4-pentadiene-1-ol, (E)-5-phenyl-penta-2-ene-4-yne-1-ol, (E)-3-(4-(1-imidazolylmethyl)phenyl]-2-propene-1-ol, E)-3-(3-(1-imidazolylmethyl)phenyl]-2-propene-1-ol, (E)-3-(2-(1-imidazolylmethyl)phenyl]-2-propene-1-ol, (Z)-3-(4-(1-imidazolylmethyl)phenyl]-2-propene-1-ol, (E)-3-(6-(1-imidazolylmethyl)pyridine-2-yl]-2-propene-1-ol, (E)-3-(5-(1-imidazolylmethyl)furan-2-yl]-2-propene-1-ol, (E)-3-(5-(1-imidazolylmethyl)thiophene-2-yl]-2-propene-1-ol, (E)-3-phenyl-1-methyl-2-propene-1-ol, (E)-2-fluoro-3-phenyl-2-propene-1-ol, 2-methoxyethanol, 3-methoxypropanol, 2-phenoxyethanol, 2-phenylthioethanol, 2-(N-methylamino)ethanol, 2-(N,N-dimethylamino)ethanol, 2-(N-methyl-N-phenylamino)ethanol, 2-(N,N-dimethylamino)ethanol, 2-(N-benzyl-N-methylamino)ethanol, 2-(1-piperazinyl)ethanol, 4-(1-piperazinyl)butanol, 6-(1-piperazinyl)hexanol, 2-(1-piperidinyl)ethanol, 2-(4-phenylpiperazine-1-yl)ethanol, 3-(4-phenylpiperazine-1-yl)propanol, 4-(4-phenylpiperazine-1-yl)butanol, 6-(4-phenylpiperazine-1-yl)hexanol, 2-(4-phenylpiperidine-1-yl)ethanol, 3-(4-phenylpiperidine-1-yl)propanol, 4-(4-phenylpiperidine-1-yl)butanol, 6-(4-phenylpiperidine-1-yl)hexanol, 2-[4-(diphenylmethyl)piperazine-1-yl]ethanol, 3-[4-(diphenylmethyl)piperazine-1-yl]propanol, 4-[4-(diphenylmethyl)piperazine-1-yl]butanol, 6-[4-(diphenylmethyl)piperazine-1-yl]hexanol, 2-morpholinoethanol, N-benzylpyrrolidine-3-yl-1-ol, N-benzylpiperidine-3-ol, 2-(1,2,3,4-tetrahydroisoquinoline-2-yl)ethanol, 2,2,2-trifluoroethanol, 2-(3,7-dihydro-3,7-dimethyl-1H-purine-2,6-dione-1-yl)ethanol, and 2-(1,2,3,6-tetrahydro-1,3-dimethyl-2,6-dioxo-7H-purine-7-yl)ethanol.

It is preferable that the reaction be carried out in an inactive solvent, such as benzene, toluene, dichloromethane, chloroform, 1,2-dichloroethane, acetonitrile, and acetone, at temperatures of 0° C. to 120° C.

The compounds prepared by Process 1 and Process 2 can be easily isolated by conventional procedures.

Starding materials for preparing 1,4-dihydropyridine derivatives of the present invention can be synthesized as follows:

1. Synthesis of 4-(3-nitrophenyl)-3-pyridyl-3-butene-2-one

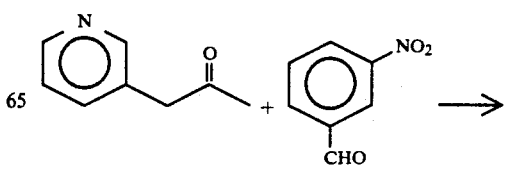

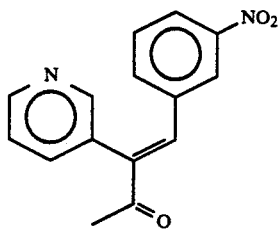

2.76 g (20 mmol) of 1-pyridyl-2-propanone and 3.066 g (20 mmol) of 3-nitrobenzaldehyde were dissolved in benzene. To this solution, 0.29 g (2.0 mmol) of piperidinium acetate was added, and the mixture was refluxed with application of heat for 6 hours for dehydration. The reaction mixture was washed with water, and dried over anhydrous sodium sulfate. The benzene contained in the reaction mixture was distilled off under reduced pressure and the remaining reaction product was chromatographed on a silica gel column, whereby the captioned compound was obtained. The yield was 4.5 g (87.9%).

N M R ($\delta$, CDCl$_3$): 2.47 (3H,s), 7.30 (1H, d, J=8.4 Hz), 7.38 (1H, dd, J=8.4Hz, 8.4 Hz), 7.39 (1H, dd, J=7.8 Hz, 5 Hz), 7.56 (1H, ddd, J=7.8 Hz, 2 Hz, 2 Hz), 7.78 (1H, s), 7.92 (1H, s), 8.10 (1H, d, J=8.4 Hz), 8.35 (1H, d, J=2 Hz), 8.66 (1H, dd, J=5 Hz, 2 Hz).

2. Synthesis of 4-(3-nitrophenyl)-3-(4-pyridyl)-3-butene-2-one

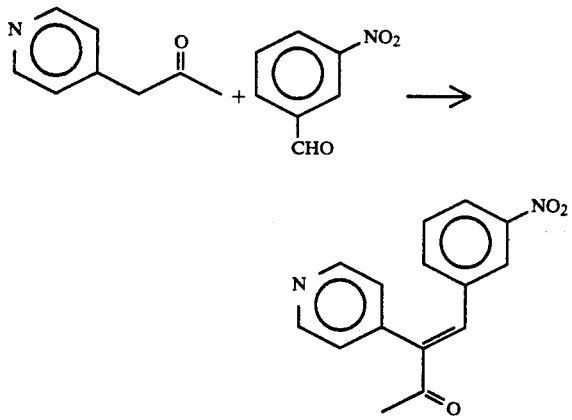

4.62 g (34 mmole) of 1-(4-pyridyl)-2-propanone and 5.14 g (34 mmol) of 3-nitrobenzaldehyde were dissolved in benzene. To this solution, 0.49 g (3.4 mmol) of piperidinium acetate was added, and the mixture was refluxed with application of heat for 6 hours for dehydration. The reaction mixture was washed with water, and dried over anhydrous sodium sulfate. The benzene contained in the reaction mixture was distilled off under reduced pressure and the remaining reaction product was chromatographed on a silica gel column, whereby the captioned compound was obtained. The yield was 7.695 g (87.3%).

N M R (67, CDCl$_3$): 2.45 (3H, s), 7.15 (2H, d, J=5.4 Hz), 7.26 (1H, d, J=8.4 Hz), 7.37 (1H, dd, J=8.4 Hz, 8.4 Hz), 7.75 (1H, s), 8.01 (1H, s), 8.12 (1H, d, J=8.4 Hz), 8.69 (1H, d, J=5.4 Hz).

3. Synthesis of 2-cyanoethyl 1,4-dihydro-2,6-dimethyl-4-(3-nitrophenyl)-5-pyridyl-pyridine-3-carboxylate

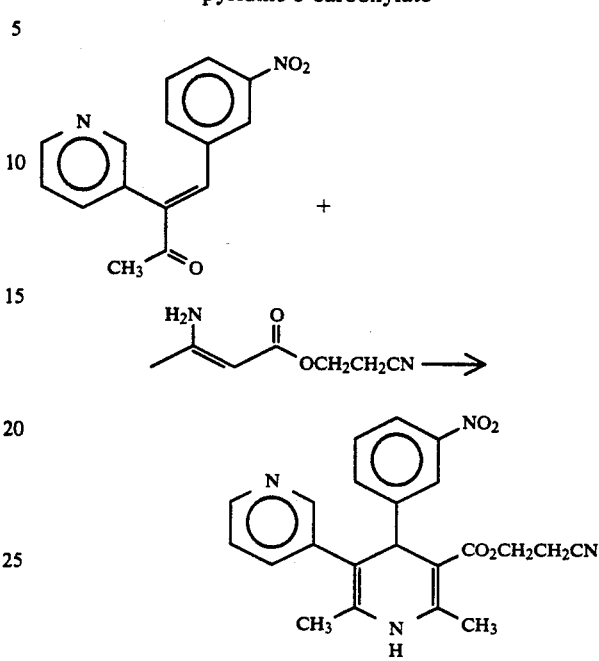

A mixture of 5.365 g (20 mmol) of 4-(3-n1trophenyl)-3-pyridyl-3-butene-2-one, 15.417 g (100 mmol) of 2-cyanoethyl 3-aminocrotonate, 5.451 g (40 mmol) of zinc chloride, and 10 g of Molecular Shieves 4A was added to 1,4-dioxane. This reaction mixture was refluxed with application of heat in an inert atmosphere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 7.94 g (87%).

IR (cm$^{-1}$, KRr): $\nu$ CO1696, $\nu$ NOZ1530, 1352, $\nu$CN2256,

N M R ($\delta$, CDCl$_3$): 1.86 (3H, s), 2.42 (3H, s), 2.58–2.66 (2H, m), 4.18–4.30 (2H, m), 4.78 (1H, s), 5.92 (1H, s), 7.19 (1H, dd, J=7.5 Hz, 4.8 Hz), 7.26–7.33 (1H, m), 7.37 (1H, dd, J=7.8 Hz, 7.8 Hz), 7.49 (1H, d, J=7.8 Hz), 8.02 (1H, d, J=7.8 Hz), 8.07 (1H, s), 8.19 (1H, d, J=2Hz), 8.43 (1H, dd, J=4.8 HZ, 2 HZ).

4. Synthesis of 1,4-dihydro-2,6-dimethyl-4-(3-nitrophenyl)-5-(4-pyridyl)pyridine-3-carboxylate

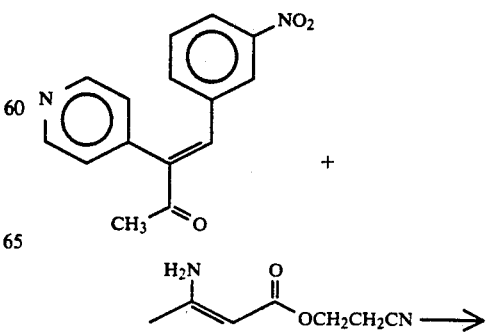

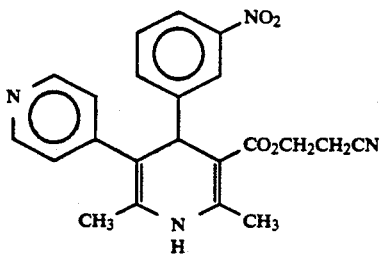

A mixuture of 5.365 g (20 mmol) of 4-(3-nitrophenyl)-3-(4-pyridyl)-3-butene-3-one, 9.250 g (60 mmol) of 2-cyanoethyl 3-aminocrotonate, 5.451 g (40 mmol) of zinc chloride, and 10 g of Molecular Shieves 4A was added to 1,4 -dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 4.980 g (62%).

I R (cm$^{-1}$, KRr): $\nu$CO1704, $\nu$NOZ1528, 1352, $\nu$CN2256,

N M R ($\delta$, CDCl$_3$): 1.97 (3H, s), 2.43 (3H, s), 2.60–2.70 (2H, m), 4.20–4.33 (2H, m), 4.88 (1H, s), 5.78 (1H, s), 6.98 (2H, d, J=6Hz), 7.37 (1H, dd, J=8.4 Hz, 8.4 Hz)., 7.48 (1H, d, J=8.4 Hz), 8.03 (1H, d, J=8.4 Hz), 8.08 (1H, s), 8.47 (2H, d, J=6 Hz).

5. Synthesis of 1,4-dihydro-2,6-dimethyl-4-(3-nitrophenyl)-5-pyridyl-pyridine-3-carboxylic acid

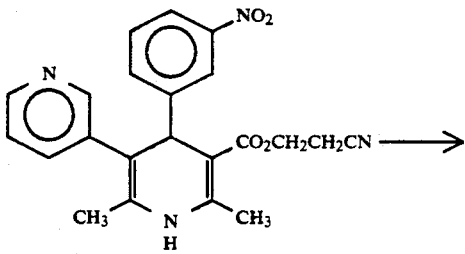

5.40 g (100 mmol) of sodium methoxide was dissolved in 40 ml of anhydrous methanol. To this solution was added, with ice-cooled, 4.04 g (10 mmol) of 1,4-dihydro-2,6-dimethyl-4-(3-nitrophenyl)-3-pyridylpyridine-3-carboxylate. The reaction mixture was stirred for 5 hours and neutralized with acetic acid. To this reaction mixture was added 400 ml of water. Crystals separated were collected, washed with water and dried under reduced pressure, whereby the captioned compound was obtained. The yield was 2.45 g (70%).

FAB Mass: 352 (M+1).

NMR ($\delta$, (CD$_3$)$_2$CO): 1.92 (3H, s), 2.38 (3H, s), 4.90 (1H, s), 7.24 (1H, dd, J=8Hz, 5 Hz), 7.46 (1H, d, J=8 Hz), 7.50 (1H, dd, J=8 Hz, 8 Hz), 7.66 (1H, d, J=8 Hz), 7.76 (1H, s), 8.01 (1H, d, J=8 Hz), 8.09 (1H, s), 8.25 (1H, s), 8.36 (1H, d, J=5 Hz).

6. Synthesis of 1,4-dihyro-2,6-dimethyl-4-(3-nitrophenyl)-5-(4-pyridyl)pyridine-3-carboxylic acid

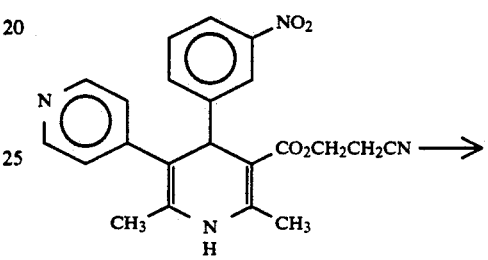

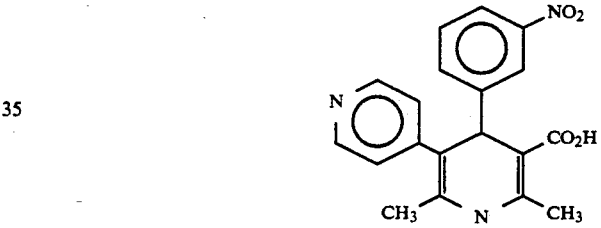

1.35 g (25 mmol) of sodium methoxide was dissolved in 20 ml of anhydrous methanol. To this solution was added, with ice-cooled, 2.02 g (5 mmols) of 1,4-dihydro-2,6-dimethyl-4-(3-nitrophenyl)-5-(4-pyridyl)pyridine-3-carboxylate. The reaction mixture was stirred at room temperature for 5 hours and neutralized with acetic acid. To this reaction mixture was added 400 ml of water. Crystals were separated from the reaction mixture, which were collected, washed with water and dried under reduced pressure, whereby the captioned compound was obtained. The yield was 1.71 g (98%).

FAB Mass: 352 (M+1).

NMR ($\delta$, (CD$_3$)$_2$CO): 2.03 (3H, s), 2.37 (3H, s), 4.99 (1H, s), 7.09 (2H, d, J=6 Hz), 7.50 (1H, dd, J=7 Hz, 7 Hz), 7.67 (1H, d, J=7 Hz), 7.83 (1H, s), 8.02 (1H, d, J=7 Hz), 8.11 (1H, s), 8.42 (2H, d, J=6 Hz).

The synthesis of 1,4 -dihydropyridine derivatives of the present invention will now be explained with reference to the examples shown below:

Example 1

Synthesis of methyl 1,4-dihydro-2,6-dimethyl-4-(3-nitrophenyl)-5-pyridyl-pyridine-3-carboxylate

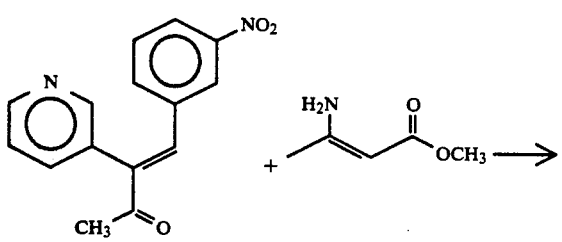

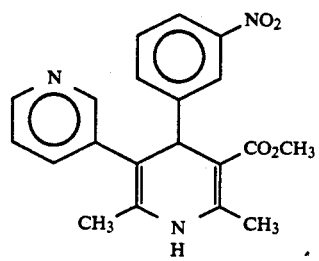

A mixuture of 268 mg (1 mmol) of 4-(3-nitrophenyl)-3-pyridyl-3-butene-2-one, 576 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 259 mg (71%).

Melting point: 148.5° to 150.6° C.

IR (cm$^{-1}$, KBr); $\nu$ CO 1700, $\nu$ NO$_2$ 1530, 1345.

Mass Analysis for C$_{20}$H$_{19}$H$_3$O$_4$: Calculated: 3.65.13750, Found: 365.1375.

NMR ($\delta$, CDCl$_3$); 1.87 (3H, s), 2.40 (3H, s), 3.62 (3H, s), 4.79 (1H, s), 5.60 (1H, s), 7.16 (1H, dd, J=8 Hz, 5Hz), 7.26 (1H, dt, J=8 Hz, 2 Hz, 2 Hz), 7.34 (1H, dd, J=8 Hz, 8 Hz), 7.46 (1H, d, J=8 Hz), 8.01, (1H, ddd, J=8 Hz, 2 Hz, 1 Hz), 8.06 (1H, t, J=2 Hz), 8.22 (1H, d, J=2 Hz), 8.42 (1H, dd, J=5 Hz, 2 Hz).

Example 2

Synthesis of ethyl 1,4-dihydro-2,6-dimethyl-4-(3-nitrophenyl)-5-pyridyl-pyridine-3-carboxylate

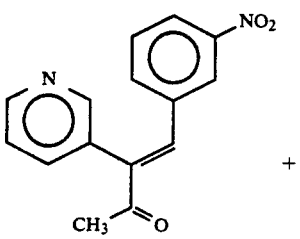

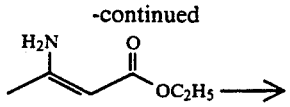

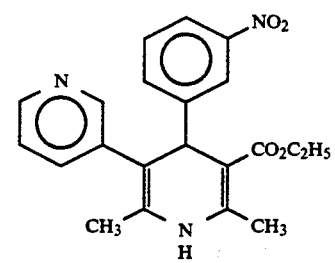

A mixuture of 268 mg (1 mmol) of 4-(3-nitrophenyl)-3-pyridyl-3-butene-2-one, 646 mg (5 mmol) of ethyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 250 mg (67%).

Melting point: oil

IR (cm$^{-1}$, KBr); $\nu$ CO 1695, $\nu$ NO$_2$ 1530, 1350.

Mass Analysis for C$_{21}$H$_{21}$N$_3$O$_4$: Calculated: 379.15316, Found: 379.15322.

NMR ($\delta$, CDCl$_3$); 1.19 (3, t, J=6 Hz), 1.88 (3H, s), 2.40 (3H, s), 4.0~4.15 (2H, m), 4.78 (1H, s), 5.60 (1H, s), 7.20 (1H, dd, J=7,5 Hz), 7.29 (1H, d, J=7 Hz), 7.35 (1H, dd, J=8 Hz, 8 Hz), 7.50 (1H, d, J=8 Hz), 8.01 (1H, d, J=8 Hz), 8.08 (1H, s), 8.24 (1H, s), 8.43 (1H, d, J=5 Hz).

Example 3

Synthesis of isopropyl 1,4-dihydro-2,6-dimethyl-4-(3-nitrophenyl)-5-pyridyl-pyridine-3-carboxylate

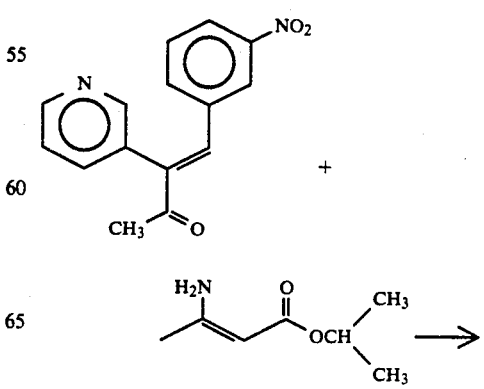

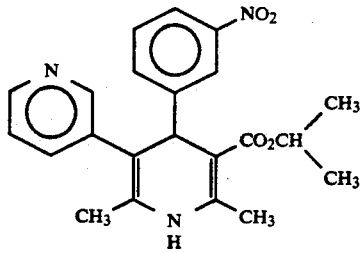

A mixuture of 268 mg (1 mmol) of 4-(3-nitrophenyl)-3-pyridyl-3-butene-2-one, 7.15 mg (5 mmol) of isopropyl 3-aminocrotonate, 273 mg (2 mmol) of zinc chloride, and 500 mg of Molecular Shieves 4A was added to 1,4-dioxiane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 290 mg (74%).

Melting point: 140.1° to 141.3° C.

IR (cm$^{-1}$, KBr); $\nu$ CO 1705, $\nu$ NO$_2$ 1530, 1350.

Mass Analysis for C$_{22}$H$_{23}$N$_3$O$_4$: Calculated: 393.16882, Found: 393.16837.

NMR ($\delta$, CDCl$_3$); 1.06 (3H, d, J=6 Hz), 1.23 (3H, d, J=6 Hz), 1.88 (3 H, s), 2.40 (3H, s), 4.77 (1H, s), 4.95 (1H, m), 5.57 (1H, s), 7.20~7.41 (3H, m), 7.50 (1H, d, J=8 Hz), 8.02 (1H, d, J=8 Hz), 8.07 (1H, s), 8.27 (1H, s), 8.44 (1H, d, J=5 Hz).

Example 4

Synthesis of n-hexyl 1,4-dihydro-2,6-dimethyl-4-(3-nitrophenyl)-5-pyridyl-pyridine-3-carboxylate

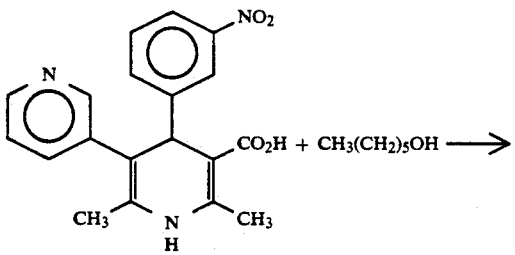

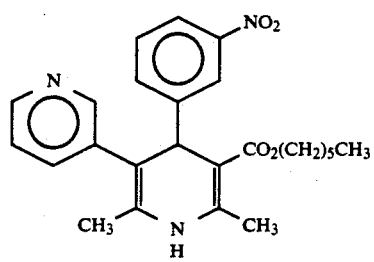

350 mg (1 mmol) of 1,4-dihydro-2,6-dimethyl-4-(3-nitrophenyl)-5-pyridylpyridine-3-carboxylic acid, 102 mg (1 mmol) of hexyl alcohol, 309 mg (1.4 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled of and the residue was chromatographed on a silica gel column, whereby the captioned compound was obtained. The yield was 389 mg (89.5%).

Melting point: 120.5° to 121.6° C.

IR (cm$^{-1}$, KRr); $\nu$ CO 1705, $\nu$ NO$_2$ 1525, 1350.

Mass Analysis for C$_{25}$H$_{29}$N$_3$O$_4$: Calculated: 435.21575, Found: 435.21680.

NMR ($\delta$, CDCl$_3$); 0.848 (3H, t, J=6 Hz), 1.12~1.30 (6H, m), 1.50~1.60 (2H, m), 1.85 (3H, s), 2.41 (3H, s), 3.96 (1H, dt, J=11, 7 Hz), 4.04 (1H, dt, J=11, 7 Hz), 4.77 (1H, s), 5.57 (1H, s), 7.18 (1H, dd, J=8, 5 Hz), 7.28 (1H, d, J=8 Hz), 7.34 (1H, dd, J=8 Hz, 8 Hz), 7.46 (1H, d, J=8 Hz), 8.00 (1H, d, J=8 Hz), 8.05 (1H, s), 8.23 (1H, s), 8.43 (1H, d, J=5 Hz).

Example 5

Synthesis of cyclohexyl 1,4-dihydro-2,6-dimethyl-4-(3-nitrophenyl)-5-pyridyl-pyridine-3-carboxylate

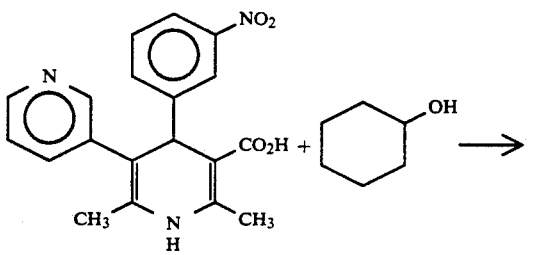

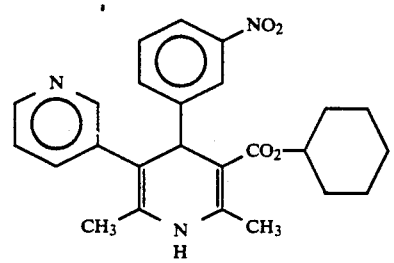

350 mg (1 mmol) of 1,4-dihydro-2,6-dimethyl-4-(3-nitrophenyl)-5-pyridylpyridine-3-carboxylic acid, 76 mg (1 mmol) of 2-methoxyethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 362 mg (83%).

Melting point: oil,

IR (cm$^{-1}$, KBr); $\nu$ CO 1694, $\mu$ NO$_2$ 1532, 1350.

Mass Analysis for C$_{25}$H$_{27}$N$_3$O$_5$; Calculated: 433.20011, Found: 433.19727.

NMR (δ, CDCl₃); 1.10~2.24 (10H, m), 1.87 (3H, s), 2.41 (3H, s), 4.64~4.76 (1H, m), 4.78 (1H, s), 5.58 (1H, s), 7.23 (1H, dd, J=7.7 Hz, 4.9 Hz), 7.34 (1H, d, J=7.7 Hz), 7.35 (1H, dd, J=8.7 Hz, 8.7 Hz), 7.49 (1H, d, J=8.7 Hz), 8.01 (1H, d, J=8.7 Hz), 8.06 (1H, s), 8.25 (1H, d, J=1.5 Hz), 8.44 (1H, dd, J=4.9 Hz, 1.5 Hz).

Example 6

Synthesis of 2-methoxyethyl 1,4-dihydro-2,6-dimethyl-4-(3-nitrophenyl)-5-pyridyl-pyridine-3-carboxylate

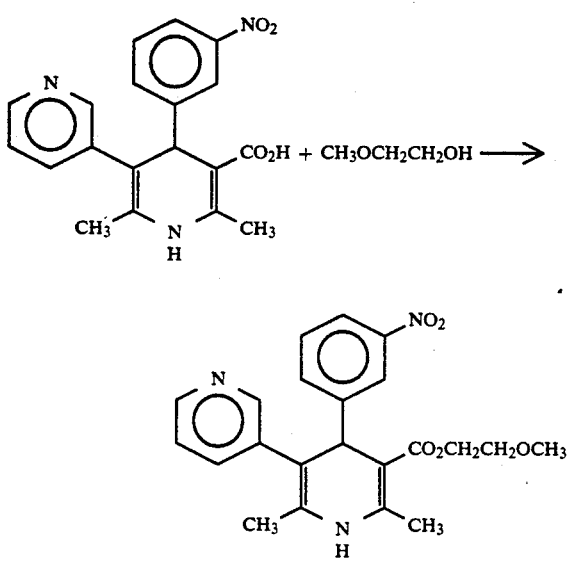

350 mg (1 mmol) of 1,4-dihydro-2,6-dimethyl-4-(3-nitrophenyl)-5-pyridylpyridine-3-carboxylic acid, 138 mg (1 mmol) of 2-phenoxyethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 384 mg (85%).

Melting point: 163.0° to 164.2° C.,

IR (cm⁻¹, KBr); ν CO 1690, ν NO₂ 1534, 1352.

Mass Analysis for C₂₂H₂₃N₃O₅; Calculated: 409.16373, Found: 409.16560.

NMR (δ, CDCl₃); 1.89 (3H,s), 2.40 (3H, s), 3.32 (3H,s), 3.45~3.58 (2H, m), 4.08~4.25 (2H, m), 4.81 (1H, s), 5.65 (1H, s), 7.28 (1H, dd, J=7.8 Hz, 5 Hz), 7.36 (1H, dd, J=7.8 Hz, 7.8 Hz), 7.41 (1H, d, J=7.8 Hz), 7.54 (1H, d, J=7.8 Hz), 8.02 (1H, d, J=7.8 Hz), 8.08 (1h, s), 8.25 (1H, s), 8.44 (1H, d, J=3.5 Hz).

Example 7

Synthesis of 2-phenoxyethyl 1,4-dihydro-2,6-dimethyl-4-(3-nitrophenyl)-5-pyridyl-pyridine-3-carboxylate

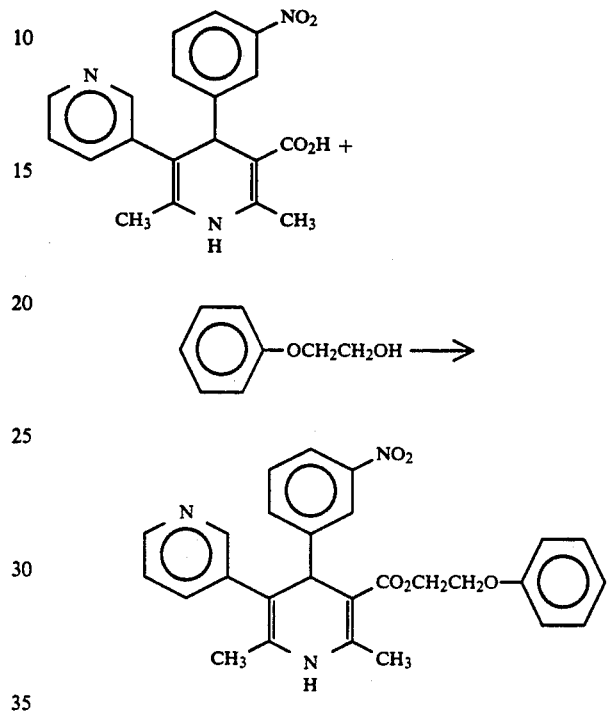

350 mg (1 mmol) of 1,4-dihydro-2,6-dimethyl-4-(3-nitrophenyl)-5-pyridylpyridine-3-carboxylic acid, 154 mg 1 mmol) of 2-(phenylthio)ethanol, 309 mg (1 mmol) of N,N'-dicyclohexylcarbodiimide, 134 mg [1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 445 mg (94%).

Melting point: 69.5° to 70.8° C.,

IR (cm⁻¹, KBr); ν CO 1696, ν NO₂ 1528, 1350.

Mass Analysis for C₂₇H₂₅N₃O₅; Calculated: 471.17938, Found: 471.17893.

NMR (δ, CDCl₃); 1.91 (3H, s), 2.41 (3H, s), 4.02–4.17 (2H, m), 4.29~4.50 (2H, m), 4.80 (1H, s), 5.702 (1H, s), 6.84 (2H, d, J=7.8 Hz), 6.96 (1H, t, J=7.8 Hz), 7.20 (1H, t, J=8.2 Hz), 7.27 (2H, J=7.8 Hz), 7.36 (1H, dd, J=7.5 Hz, 5Hz), 7.43~7.51 (2H, m), 7.96 (1H, d, J=8.2 Hz), 8.07 (1H, s), 8.27 (1H, d, J=2.4 Hz), 8.45 (1H, dd, J=5 Hz, 2.4 Hz).

Example 8

Synthesis of 2-(phenylthio)ethyl 1,4-dihydro-2,6-dimethyl-4-(3-nitrophenyl)-5-pyridyl-pyridine-3-carboxylate

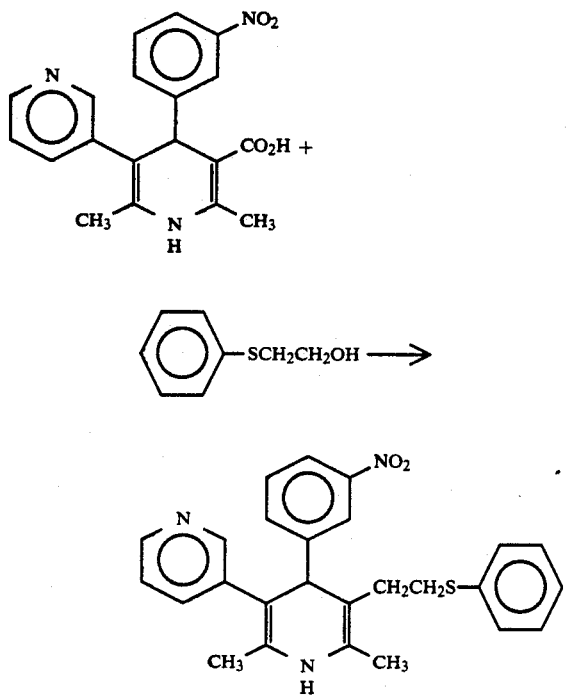

350 mg (1 mmol) of 1,4-dihydro-2,6-dimethyl-4-(3-nitrophenyl)-5-pyridylpyridine-3-carboxylic acid, 100 mg (1 mmol) of 2,2,2-trifluoroethanol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 470 mg (96%).

Melting point: 152.7° to 154.3° C.

IR (cm$^{-1}$, KBr); ν CO 1704, ν $NO_2$ 1528, 1348,

Mass Analysis for $C_{27}H_{24}N_3O_4S$; Calculated: 487.15653, Found: 487.15736, NMR (δ, $CDCl_3$); 1.89 (3H, s), 2.40 (3H, s), 3.70 (2H, t, J=7.2 Hz), 4.13~4.27 (2H, m), 4.78(1H, s), 5.69 (1, s), 7.14~7.39 (7H, m), 7.42 (1H, d, J=8.4 Hz), 7.49 (1H, d, J=7.2 Hz), 8.02 (1H, d, J=7.2 Hz), 8.06 (1H, s), 8.26 (1H, d, J=2.4 Hz), 8.46 (1H, dd, J=6Hz, 2.4 Hz).

Example 9

Synthesis of 2,2,2-trifluoroethyl 1,4-dihydro-2,6-dimethyl-4-(3-nitrophenyl)-5-pyridyl-pyridine-3-carboxylate

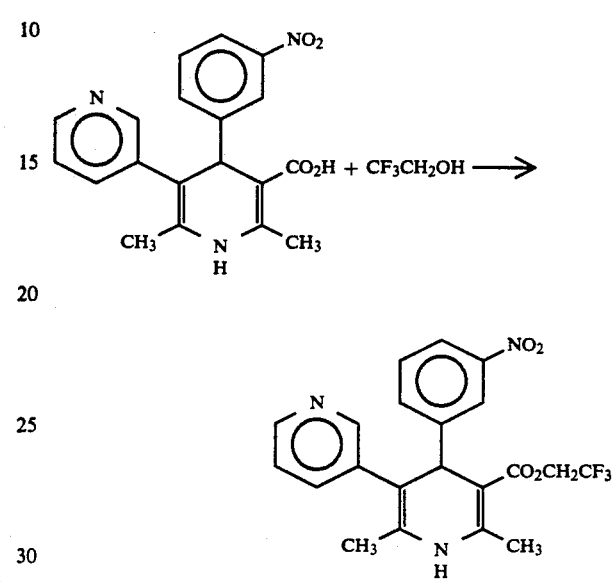

350 mg (1 mmol) of 1,4-dihydro-2,6-dimethyl-4-(3ni-trophenyl)-5-pyridylpyridine-3-carboxylic acid, 100 mg (1 mmol) of 2,2,2-trifluoroethanol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 450 mg (100%).

Melting point: 152.7° to 154.3° C.

IR (cm$^{-1}$, KBr); ν CO 1710, ν $NO_2$ 1528, 1352.

Mass Analysis for $C_{21}H_{18}F_3N_3O_4$: Calculated: 433.12489, Found: 433.12338.

NMR (δ, $CDCl_3$); 1.88 (3H, s), 2.42 (3H, s), 4.27~4.50 (2H, m), 4.76 (1H, s), 5.84 (1H, s), 7.26 (1H, dd, J=6.6 Hz, 4.2 Hz), 7.33 (1H, d, J=6.6 Hz), 7.35 (1H, dd, J=7.8 Hz, 7.8 Hz), 7.43 (1H, d, J=7.8 Hz), 8.03 (1H, d, J=7.8 Hz), 8.07 (1H, s), 8.23 (1H, s), 8.45 (1H, d, J=4.2 Hz).

Example 10

Synthesis of 2-propene-1-yl 1,4-dihydro-2,6-dimethyl-4-(3-nitrophenyl)-5-pyridyl-pyridine-3-carboxylate

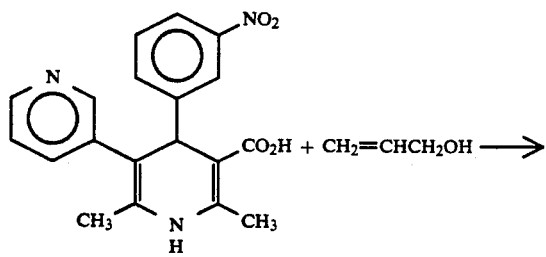

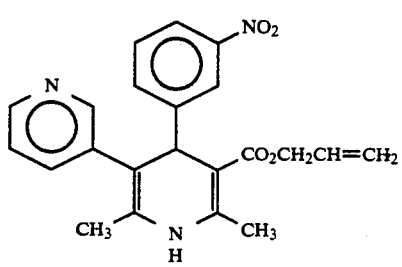

350 mg (1 mmol) of 1,4-dihydro-2,6-dimethyl-4-(3-nitrophenyl)-5-pyridylpyridine-3-carboxylic acid, 58 mg (1 mmol) of 2-propene-1-ol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 400 mg (100%).

Melting point: 141.8° to 143.6° C.,

IR (cm$^{-1}$, KBr); $\nu$ CO 1695, $\nu$ NO$_2$ 1535, 1350,

Mass Analysis for $C_{22}H_{21}N_3O_4$: Calculated: 391.15316, Found: 391.15218.

NMR ($\delta$, CDCl$_3$); 1.87 (3H, s), 2.41 (3H,s), 4.50 (1H, dd, J=12.6 Hz), 4.56 (1H, dd, J=12.6 Hz), 4.80 (1H, s), 5.14 (1H, d, J=11 Hz), 5.16 (1H, d, J=19 Hz), 5.63 (1H, s), 5.85 (1H, ddt, J=19, 11, 6 Hz), 7.16 (1H, dd, J=8,5 Hz), 7.25 (1H, d, J=8 Hz), 7.34 (1H, dd, J=8 Hz, 8 Hz), 7.48 (1H, d, J=8 Hz), 8.01 (1H, d, J=8 Hz), 8.07 (1H, s), 8.22 (1H, s), 8.42 (1H, d, J=5 Hz).

Example 11

Synthesis of 2-propyne-1-yl 1,4-dihydro-2,6-dimethyl-4-(3-nitrophenyl)-5-pyridyl-pyridine-3-carboxylate

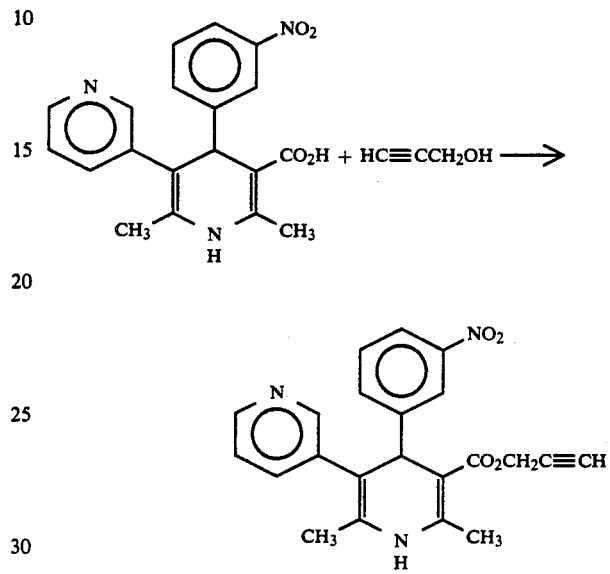

350 mg (1 mmol) of 1,4-dihydro-2,6-dimethyl-4-(3-nitrophenyl)-5-pyridylpyridine-3-carboxylic acid, 56 mg (1 mmol) of 2-propyne-1-ol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 420 mg (100%).

Melting point: 179.2° to 180.1° C.,

IR (cm$^{-1}$, KBr); $\nu$ CO 1695, $\nu$ NO$_2$ 1530, 1350.

Mass Analysis for $C_{22}H_{19}N_3O_4$; Calculated: 389.13751, Found: 389.13593.

NMR ($\delta$, CDCl$_3$); 1.87 (3H,s), 2.39 (1H, t, J=2Hz), 2.41 (3H, s), 4.58 (1H, dd, J=15, 2 Hz), 4.65 (1H, dd, J=15,2 Hz), 4.79 (1H, s), 5.68 (1H, s), 7.15 (1H, dd, J=8,5 Hz), 7.25 (1H, dt, J=8, 2 Hz), 7.35 (1H, dd, J=8 Hz, 8 Hz), 7.52 (1H, d, J=8 Hz), 8.01 (1H, d, J=8 Hz), 8.08 (1H, s), 8.22 (1H,s), 8.42 (1H, dd, J=5, 2 Hz).

Example 12

Synthesis of (2E, 4E)-2,4-hexadiene-1-yl 1,4-dihydro-2,6-dimethyl-4-(3-nitrophenyl)-5-pyridyl-pyridine-3-carboxylate

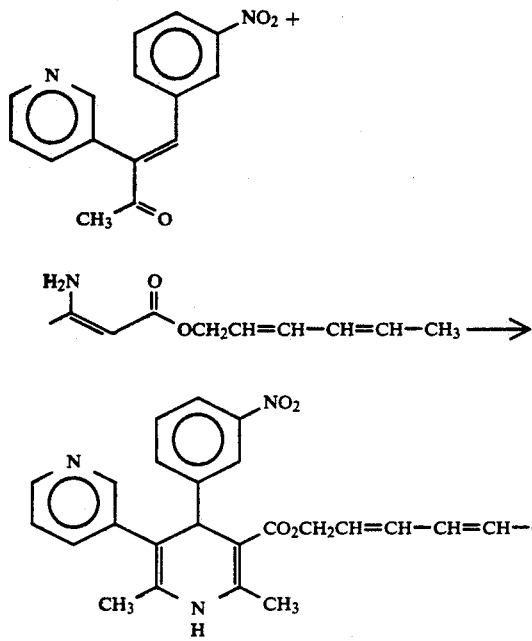

268 mg (1 mmol) of 4-(3-nitrophenyl)-3-pyridyl-3-butene-2-one, 905 mg (5 mmol) of (2E,4E)-2,4-hexadiene-1-yl 3-aminocrotonate, 273 mg (2 mmol) of zinc chloride, and 500 mg of Molecular Shieves 4A were added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed b extraction with chloroform. The solvents contained in the extract were distilled off and the residue was chromatographed on a silica gel column, whereby the captioned compound was obtained. The yield was 182 mg (42.3%).

Melting point: 162.3° to 164.2° C.

IR (cm$^{-1}$ KBr); $\nu$ CO 1695, $\nu$ NO$_2$ 1525, 1350.

Mass Analysis for C$_{25}$H$_{25}$N$_3$O$_4$: Calculated: 431.18446, Found: 341.18439.

NMR ($\delta$, CDCl$_3$); 1.74 (3H, d, J=7 Hz), 1.87 (3H, s), 2.39 (3H, s), 4.47 (1H, dd, J=12,7 Hz), 4.56 (1H, dd, J=12, 7 Hz), 4.79 (1H, s), 5.55 (1H, dt, J=13, 7 Hz), 5.56 (1H, s), 5.67 (1H, dq, J=14, 7 Hz), 6.00 (1H, dd, J=14, 10 Hz), 6.11 (1H, dd, J=13, 10 Hz), 7.20 (1H, dd, J=8, 5 Hz), 7.28 (1H, dt, J=5, 2 Hz), 7.34 (1H, t, J=8 Hz), 7.48 (1H, d, J=8 Hz), 8.00 (1H, d, J=8 Hz), 8.06 (1H, s), 8.23 (1H, d, J=2 Hz), 8.42 (1H, dd, J=5, 2 Hz).

Example 13

Synthesis of (E)-3-phenyl-2-propene-1-yl 1,4-dihydro-2,6-dimethyl-4-(3-nitrophenyl)-5-pyridyl-pyridine-3-carboxylate

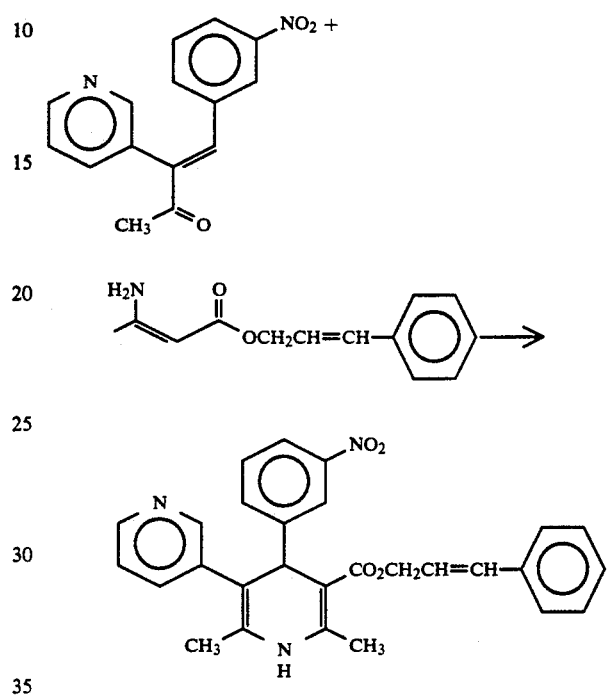

268 mg (1 mmol) of 4-(3-nitrophenyl)-3-pyridyl-1-3-butene-2-one, 1.08 g (5 mmol) of (E)-3-phenyl-2-propene-1-yl 3-aminocrotonate, 273 mg (2 mmol) of zinc chloride, and 500 mg of Molecular Shieves 4A were added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 315 mg (66.9%).

Melting point: 146.0° to 147.1° C.,

IR (cm$^{-1}$, KBr); $\nu$ CO 1700, $\nu$ NO$_2$ 1530, 1350.

Mass Analysis for C$_{28}$H$_{25}$N$_3$O$_4$: Calculated: 467.18446, Found: 467.18283.

NMR ($\delta$, CDCl$_3$); 1.88 (3H, s), 2.42 (3H, s), 4.64 (1H, dd, J=12, 7 Hz), 4.72 (1H, dd, J=12, 7 Hz), 4.82 (1H, s), 5.65 (1H, s), 6.20 (1H, dt, J=15, 6 Hz), 6.52 (1H, d, J=15 Hz), 7.24 (1H, dd, J=8, 5 Hz), 7.26 ~7.35 (7H, m), 7.48 (1H, d, J=8 Hz), 7.99 (1H, d, J=8 Hz), 8.08 (1H, s), 8.24 (1H, s), 8.42 (1H, d, J=5 Hz).

Example 14

Synthesis of (Z)-3-phenyl-2-propene-1-yl 1,4-dihydro-2,6-dimethyl-4-(3-nitrophenyl)-5-pyridyl-pyridine-3-carboxylate

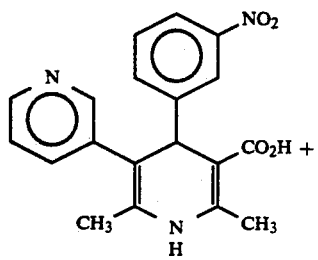

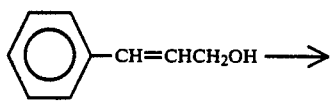

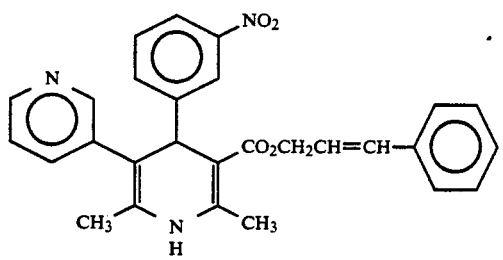

350 mg (1 mmol) of 1,4-dihydro-2,6-dimethyl-4-(3-nitrophenyl)-5-pyridylpyridine-3-carboxylic acid, 135 mg (1 mmol) of (Z)-3-phenyl-2-propene-1-ol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 467 mg (100%).

Melting point: 129.9° to 130.6° C.

IR (cm$^{-1}$, KBr); $\nu$ CO 1698, $\nu$ NO$_2$ 1530, 1348.

Mass Analysis for C$_{28}$H$_{25}$N$_3$O$_4$: Calculated: 467.18446, Found: 467.18401.

NMR ($\delta$, CDCl$_3$); 1.90 (3H, s), 2.42 (3H, s), 4.73~4.88 (2H, m), 4.79 (1H,s), 5.70 (1H, s), 5.73 (1H, dt, J=12 Hz, 6 Hz), 6.62 (1H, d, J=12 Hz), 7.15 (2H, d, J=4 Hz), 7.23~7.41 (5H, m), 7.46~7.54 (2H, m), 8.01 (1, d, J=8 Hz), 8.06 (1H, s), 8.28 (1H, s), 8.46 (1H, d, J=4.6 Hz).

Example 15

Synthesis of 3-phenyl-2-propyne-1-yl 1,4-dihydro-2,6-dimethyl-4-(3-nitrophenyl)-5-pyridyl-pyridine-3-carboxylate

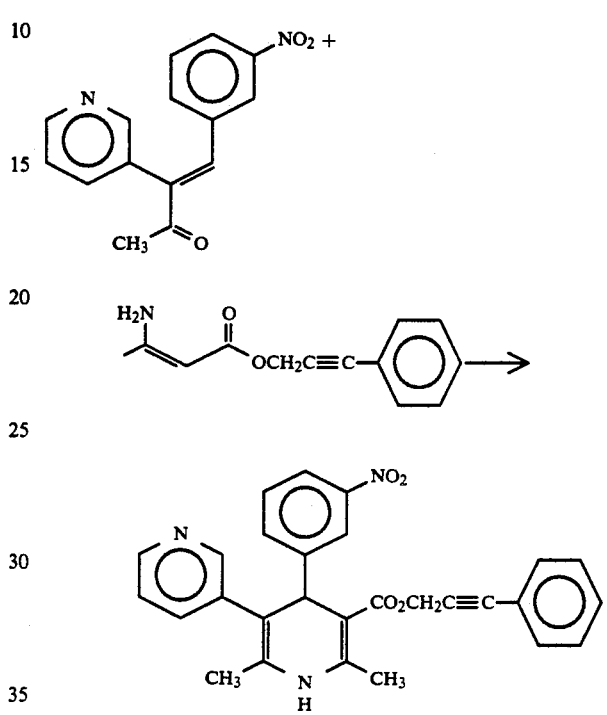

0.268 g [1 mmol] of 4-(3-nitrophenyl)-3-pyridyl-3-butene-2-one, 1.075 g (5 mmol) of 3-phenyl-2-propyne-1-yl 3-aminocrotonate, 0.273 g (2 mmol) of zinc chloride, 0.5 g of Molecular Shieves 4A were added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 0.33 g (70.9%).

Melting point: 156° C. (dec.).

IR (cm$^{-1}$, KBr); $\nu$ CO 1700, $\nu$ NO$_2$ 1530, 1350.

Mass Analysis for C$_{28}$H$_{23}$N$_3$O$_4$: Calculated: 465.16881, Found: 465.17159.

NMR ($\delta$, CDCl$_3$); 1.89 (3H, s), 2.43 (3H, s), 4.82 (1H, d, J=15 Hz), 4.84 (1H, s), 4.99 (1H, d, J=15 Hz), 5.68 (1H, s), 7.20~7.42 (9 H, m), 7.54 (1H, d, J=8 Hz), 8.00 (1 H, d, J=8 Hz), 8.11 (1H, s), 8.26 (1H, s), 8.43 (1H, d, J=5 Hz).

Example 16

Synthesis of (2E)-5phenyl-penta-2-ene-4-yne-1-yl 1,4-dihydro-2,6-dimethyl-4-(3-nitrophenyl)-5-pyridyl-pyridine-3-carboxylate

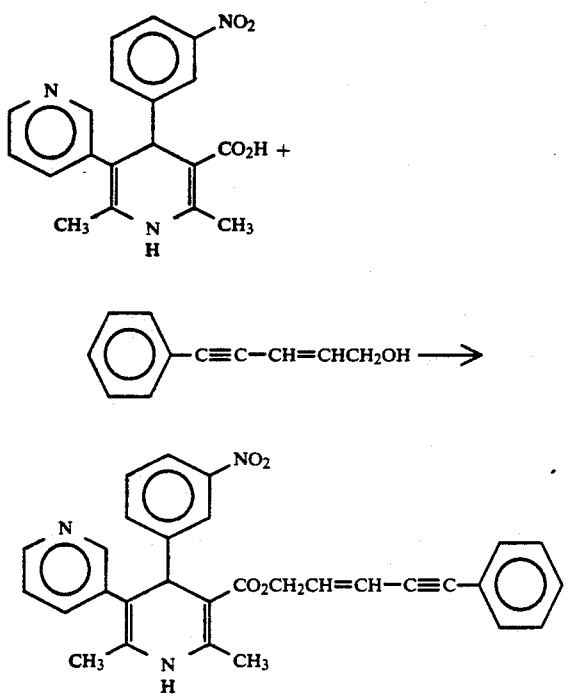

350 mg (1 mmol) of 1,4-dihydro-2,6-dimethyl-4-(3-nitrophenyl)-5-pyridylpyridine-3-carboxylic acid, 158 mg (1 mmol) of (2E)-5-phenyl-penta-2-ene-4-yne-1-ol, 309 mg (1 mmol) of N,N′-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 475 mg (97%).

Melting point: 189.9° to 191.1° C.

IR (cm$^{-1}$, KBr); $\nu$ CO 1678, $\nu$ NO$_2$ 1528, 1350.

Mass Analysis for $C_{30}H_{25}N_3N_4$: Calculated: 491.18446. Found: 491.18594.

NMR ($\delta$, CDCl$_3$): 1.91 (3H, s), 2.43 (3H, s), 4.58 (1H, dd, J=15 Hz 5.4 Hz), 4.65 (1H, dd, J=15 Hz, 5.4 Hz), 4.82 (1H, s), 5.72 (1H, s), 5.80 (1H, d, J=15 hz), 6.18 (1H, dt, J=15 hz, 5.4 Hz), 7.28~7.53 (9 H, m), 8.03 (1H, d, J=8 Hz), 8.08 (1H, s), 8.28 (1H, d, J=2.1 Hz), 8.46 (1H, dd, J=5.7 Hz, 2.1 Hz).

Example 17

Synthesis of (2E,4E)-5-phenyl-2,4-pentadiene-1-yl 1,4-dihydro-2,6-dimethyl-4-(3-nitrophenyl)-5-pyridyl-pyridine-3-carboxylate

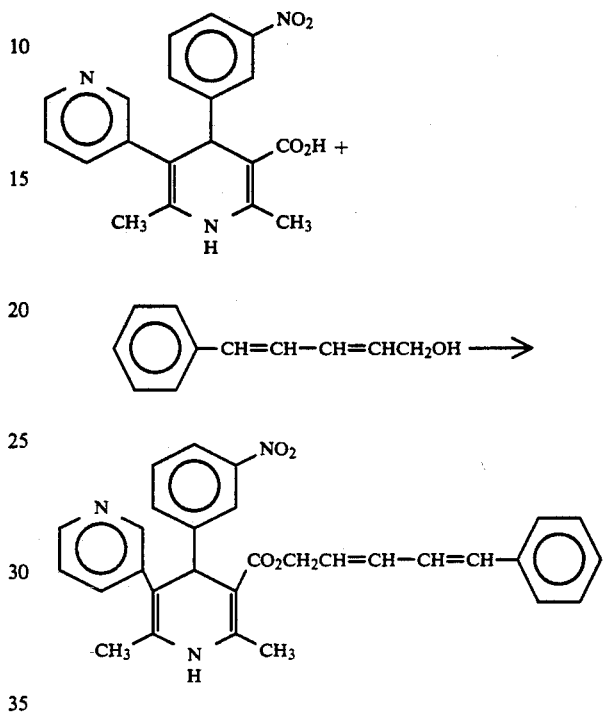

350 mg (1 mmol) of 1,4-dihydro-2,6-dimethyl-4-(3-nitrophenyl)-5-pyridylpyridine-3-carboxylic acid, 160 mg 1 mmol) of (2E,4E)-5-phenyl-2,4-pentadiene-1-ol, 309 mg (1 mmol) of N,N′-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 377 mg (76%).

Melting point: 182° C. (dec.).

IR (cm$^{-1}$, KBr); $\nu$ CO 1698, $\nu$ NO$_2$ 1528, 1346.

Mass Analysis for $C_{30}H_{27}N_3O_4$: Calculated: 493.20011, Found: 493.19698.

NMR ($\delta$, CDCl$_3$); 1.89 (3H, s), 2.42 (3H, s), 4.56 (1H, dd, J=14.3 Hz, 6.6 Hz), 4.66 (1H, dd, J=14.3 Hz, 6.6 Hz), 4.82 (1H, s), 5.65 (1H, s), 5.80 (1H, dt, J=15 Hz, 6 Hz), 6.29 (1H, dd, J=15 Hz, 10.2 Hz), 6.49 (1H, dd, J=15.5 Hz, 10.2 Hz), 6.72 (1H, d, J=15.5 Hz), 7.18~7.43 (8H, m), 7.50 (1H, d, J=8.3 Hz), 8.02 (1H, d, J=8.3 Hz), 8.09 (1H, s), 8.26 (1H, d, J=2.4 Hz), 8.44 (1H, dd, J=4.8 Hz, 2.4 Hz).

Example 18

Synthesis of
(E)-3-[4-(1-imidazolylmethyl)phenyl]-2-propene-1-yl 1,4-dihydro-2,6-dimethyl-4-(3-nitrophenyl)-5-pyridylpyridine-3-carboxylate

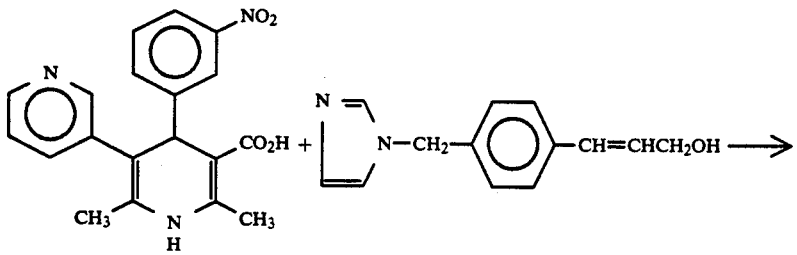

350 mg (1 mmol) of 1,4-dihydro-2,6-dimethyl-4-(3-nitrophenyl)-5-pyridylpyridine-3-carboxylic acid, 214 mg (1 mmol) of [E]-3-[4-(1-imidazolylmethyl)phenyl]-2-propene-1-ol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 530 mg (97%).

Melting point: oil.
IR (cm$^{-1}$, KBr); $\nu$ CO 1692, $\nu$ NO$_2$ 1528, 1350.
Mass Analysis for C$_{32}$H$_{29}$N$_5$O$_4$: Calculated; 547.22190, Found: 547.2213.
NMR ($\delta$, CDCl$_3$); 1.86 (3H, s), 2.43 (3H, s), 4.61 (1H, dd, J=12.6 Hz, 6 Hz), 4.74 (1H, dd, J=12.6 Hz, 6 Hz), 4.81 (1H, s), 5.19 (2H, s), 5.63 (1H, s), 6.20 (1H, dt, J=16.2 Hz, 6.3 Hz), 6.47 (1H, d, J=16.2 Hz), 6.98 (1H, s), 7.32~7.36 (8H, m), 7.50 (1H, d, J=7.8 Hz), 7.97 (1H, d, J=7.8 Hz), 8.05 (2H, s), 8.22 (1H, d, J=2.1 Hz), 8.41 (1H, dd, J=5.1 Hz, 2.1 Hz).

Example 19

Synthesis of
(Z)-3-[4-(1-imidazolylmethyl)phenyl]-2-propene-1-yl 1,4-dihydro-2,6-dimethyl-4-(3-nitrophenyl)-5-pyridylpyridine-3-carboxylate

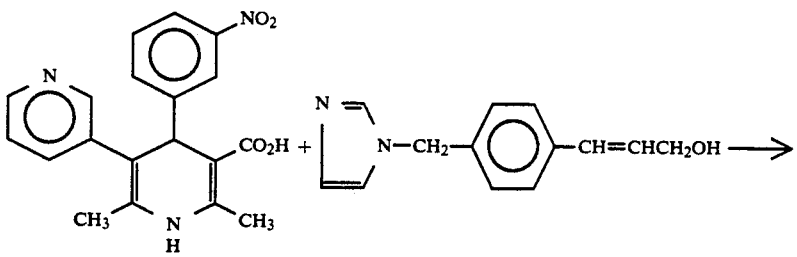

210 mg (0.6 mmol) of 1,4-dihydro-2,6-dimethyl-4-(3-nitrophenyl)-5-pyridylpyridine-3-carboxylic acid, 107 mg (0.5 mmol) of (Z)-3-[4-(1-imidazolylmethyl)phenyl]-2-propene-1-ol, 155 mg (0.75 mmol) of N,N'-dicyclohexylcarbodiimide, 67 mg (0.55 mmol) of 4-N,N- dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 273 mg (100%).

Melting point: oil,
IR (cm$^{-1}$, KBr); $\nu$ CO 1692, $\nu$ NO$_2$ 1532, 1350.
Mass Analysis for C$_{32}$H$_{29}$N$_4$O$_4$: Calculated: 547.22190, Found: 547.2246.
NMR ($\delta$, CDCl$_3$); 1.86 (3H, s), 2.38 (3H, s), 4.74 (1H, d, J=6 Hz), 4.75 (1H, d, J=6 Hz), 4.77 (1H, s), 5.20 (2H, s), 5.80 (1H, dt, J=11.7 Hz, 6 Hz), 6.57 (1H, d, J=11.74 Hz), 7.00 (1H, s), 7.07~7.40 (7H, m), 7.33 (1H, t, J=7.8 Hz), 7.48 (1H, d, J=7.8 Hz), 7.97 (1H, d, J=7.8 Hz), 8.02 (1H, s), 8.06 (1H, s), 8.21 (1H, s), 8.42 (1H, d, J=2.7 Hz).

Example 20

Synthesis of (E)-3-[(5-imidazolylmethyl)thiophene-2-yl]-2-propenyl 1,4-dihydro-2,6-dimethyl-4-(3-nitrophenyl)-5-pyridyl-pyridine-3-carboxylate mg (1 mmol) of (E)-3-[(5-imidazolylmethyl)thiophene-2-yl]-2-propene-1-ol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 400 mg (72.4%).

Melting point: 200.4° to 201.7° C.
IR (cm$^{-1}$, KBr); $\nu$ CO 1698, $\nu$ NO$_2$ 1530, 1350.
Mass Analysis for C$_{30}$H$_{27}$N$_5$O$_4$S: Calculated: 553.17832, Found: 53.17860.
NMR ($\delta$, CDCl$_3$); 184 (3H, s), 2.41 (3H, s), 4.54 (1H, dd, J=12, 3 Hz), 4.67 (1H, dd, J=12, 3 Hz), 5.20 (2H, s), 5.74 (1H, s), 5.91 (1H, dt, J=15, 6 Hz), 6.49 (1H, d, J=15 Hz), 6.74 (1H, d, J=4 Hz), 6.81 (1H, d, J=4 Hz), 6.96 (1H, s), 7.08 (1H, s), 7.15 (1H, dd, J=7.5 Hz), 7.24 (1H, dt, J=7.2 Hz), 7.31 (1H, t, J=8 Hz), 7.46 (1H, d, J=8 Hz), 7.56 (1H, s), 7.97 (1H, d, J=8 Hz), 8.05 (1H, s), 8.20 (1H, s), 8.41 (1H, dd, J=5.2 Hz).

Example 21

Synthesis of 2-[4-(diphenylmethyl)piperazinyl]ethyl 1,4-dihydro-2,6-dimethyl-4-(3-nitrophenyl)-5-pyridyl-pyridine-3-carboxylate

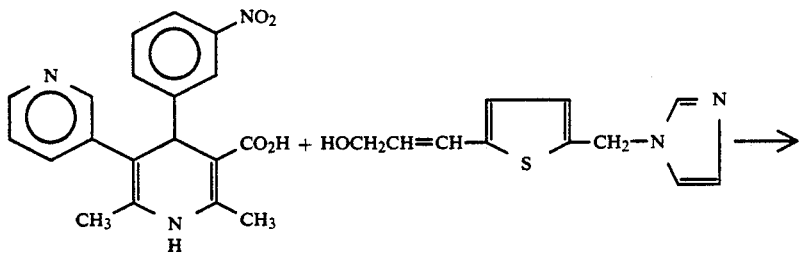

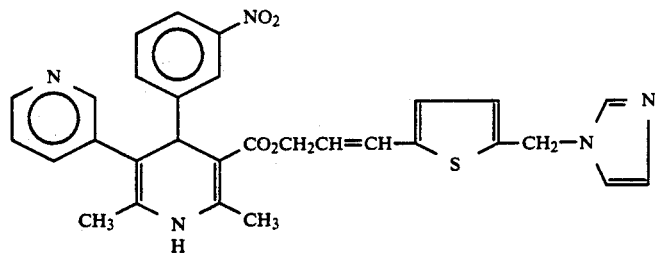

350 mg (1 mmol) of 1,4-dihydro-2,6-dimethyl-4-(3-nitrophenyl)-5-pyridylpyridine-3-carboxylic acid, 220

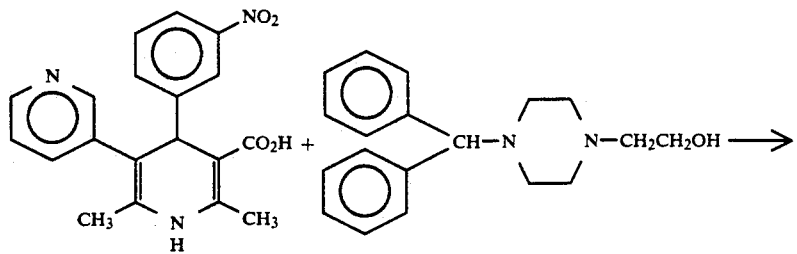

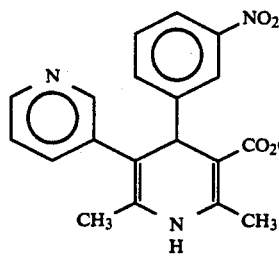
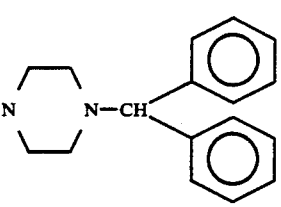

350 mg (1 mmol) of 1,4-dihydro-2,6-dimethyl-4-(3-nitrophenyl)-5-pyridylpyridine-3-carboxylic acid, 327 mg (1.1 mmol) of (2-[4-(diphenylmethyl)piperazinyl]ethanol, 309 mg (1 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 5.63 mg (89.4%).

Melting point: 171.8° to 173.3° C.

IR (cm$^{-1}$, KBr); $\nu$ CO 1695, $\nu$ NO$_2$ 1530, 1350.

Mass Analysis for C$_{38}$H$_{39}$N$_5$O$_4$; Calculated: 629.30015, Found: 629,29894.

NMR ($\delta$, CDCl$_3$); 1.85 (3H, s), 2.30~2.48 (6H, m), 2.39 (3H, s), 2.53~2.60 (4H, m), 4.05~4.21 (2H, m), 4.17 (1H, s), 4.75 (1H, s), 5.55 (1H, s), 7.13 (1H, dd, J=8, 5 Hz), 7.17~7.29 (11H, m), 7.39 (1H, d, J=8 Hz), 7.45 (1H, d, J=8 Hz), 7.96 (1H, d, J=8 Hz), 8.03 (1 H, s), 8.20 (1H, s), 8.42 (1H, d, J=5 Hz), Example 22

Synthesis of 2-(4-phenylpiperazinyl)ethyl 1,4-dihydro-2,6-dimethyl-4-(3-nitrophenyl)-5-pyridyl-pyridine-3-carboxylate

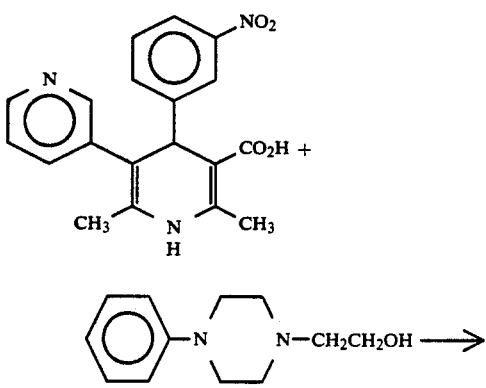

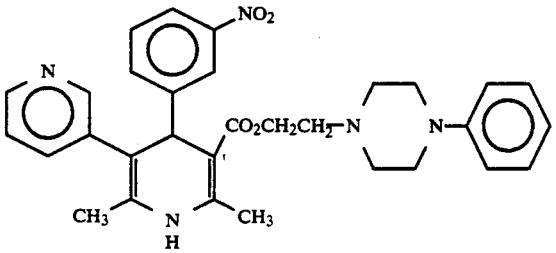

350 mg (1 mmol) of 1,4-dihydro-2,6-dimethyl-4-(3-nitrophenyl-3-carboxylic acid, 206 mg (1 mmol) of 2-(4-phenylpiperazinyl)ethanol, 309 mg (1 mmol) of N,N'-dicyclohexylcarbodiimide, 134 mg (1.1 mmol) of 4-N,N-dimethylaminopyridine were dissolved in 10 ml of toluene, wit application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 369 mg (68.5%).

Melting point: oil,

IR (cm$^{-1}$, KBr); $\nu$ CO 1695, $\nu$ NO$_2$ 1530, 1350,

Mass Analysis for C$_{31}$H$_{33}$N$_5$O$_4$; Calculated; 539.25320, Found: 539.25105.

NMR ($\delta$, CDCl$_3$); 1.86 (3H, s), 2.41 (3H, s), 2.56~2.63 (6H, m), 3.12 (4H, t, J=5 Hz), 4.15 (1H, dt, J=11, 6 Hz), (4.22 (1H, dt, J=11, 6 Hz), 4.79 (1H, s), 5.53(1H,s), 6.85 (1H, t, J=8 Hz), 6.90 (2H, d, J=8 Hz), 7.14 (1H, dd, J=8, 5 Hz), 7.22 ~7.29 (3H, m), 7.34 (1H, t, J=8 Hz), 7.50 (1H, d, J=8 Hz), 8.00 (1H, d, J=8 Hz), 8.06 (1H, s), 8.22 (1H, d, J=2 Hz), 8.42 (1H, dd, J=5, 2 Hz).

Example 23

Synthesis of 2-(4-phenylpiperidino)ethyl 1,4-dihydro-2,6-dimethyl-4-(3-nitrophenyl)-5-pyridyl-pyridine-3-carboxylate

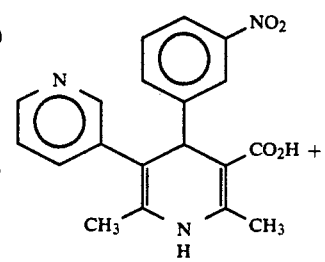

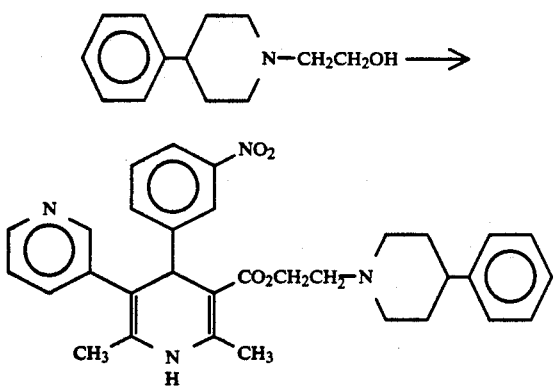

350 mg (1 mmol) of 1,4-dihydro-2,6-dimethyl-4-(3-nitrophenyl)-5-pyridylpyridine-3-carboxylic acid, 205 mg (1 mmol) of 2-(4-phenylpiperidino)ethanol, 309 mg (1 mmol) of N,N-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 220 mg (41%).
Melting point: oil.
IR (cm$^{-1}$, KBr); $\nu$ CO 1696, $\nu$ NO$_2$ 1530, 1350.
Mass Analysis for C$_{32}$H$_{34}$N$_4$O$_4$: Calculated: 538.25795, Found: 538.25683.
NMR ($\delta$, CDCl$_3$); 1.60~1.82 (4H, m), 1.86 (3H, s), 2.06~2.16 (2H, m) 2.42 (3H, s), 2.45~2.50 (1H, m), 2.55~2.64 (2H, m), 2.92~3.02 (2H, m), 4.09~4.26 (2H, m), 4.80 (1H, s), 5.58 (1H, s), 7.06 (1H, dd, J=8, 5 Hz), 7.18~7.29 (6H, m), 7.35 (1H, t, J=9 Hz), 7.39 (1H, d, J=9 Hz), 8.01 (1H, d, J=9 Hz), 8.06 (1H, s), 8.22 (1H, d, J=2Hz), 8.42 (1H, dd, J=5, 2 Hz).

Example 24

Synthesis of 2-(N-benzyl-N-methylamino)ethyl 1,4-dihydro-2,6-dimethyl-4(3-nitrophenyl)-5-pyridyl-pyridine-3-carboxylate

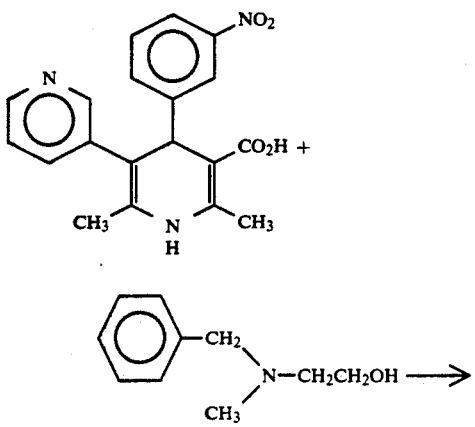

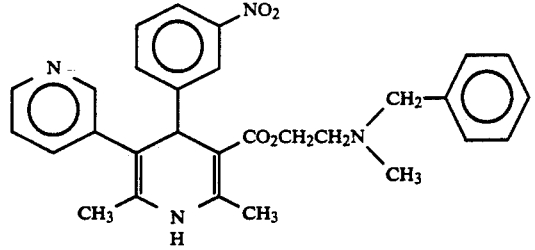

350 mg (1 mmol) of 1,4-dihydro-2,6-dimethyl-4-(3-nitrophenyl)-5-pyridylpyridine-3-carboxylic acid, 182 mg (1.1 mmol) of 2-(N-benzyl-N-methylamino)ethanol, 309 mg (1 mmol) of N,N-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 403 mg (80.9%).
Melting point: oil.
IR (cm$^{-1}$, KBr); $\nu$ CO 1695, $\nu$ NO$_2$ 1530, 1350.
Mass Analysis for C$_{29}$H$_{30}$N$_4$O$_4$: Calculated: 498.22666, Found: 487.22511.
NMR ($\delta$, CDCl$_3$); 1.86 (3H, s), 2.19 (3H, s), 2.38 (3H, s), 2.55 (1H, dd, J=15, 6 Hz), 3.47 (2H, s), 4.13 (2H, t, J=6 Hz), 4.78 (1H, s), 5.55 (1H, s), 7.16 (1H, dd, J=7, 5 Hz), 7.22~7.30 (7H, m), 7.44 (1H, d, J=7 Hz), 7.98 (1H, d, J=8 Hz), 8.05 (1H, s), 8.22 (1H, s), 8.43 (1H, d, J=5 Hz).

Example 25

Synthesis of 2-(1,2,3,4-tetrahydroisoquinoline-2-yl)-ethyl 1,4-dihydro-2,6-dimethyl-4-(3-nitrophenyl)-5-pyridyl-pyridine-3-carboxylate

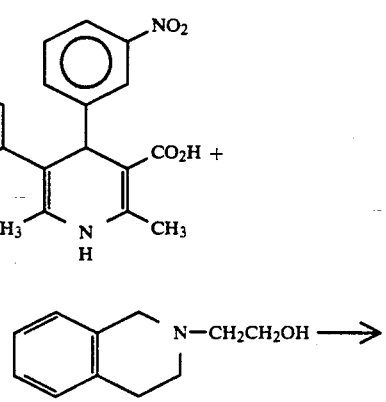

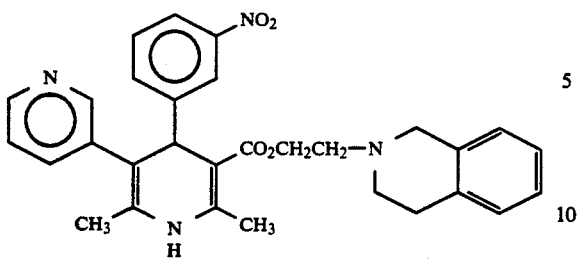

350 mg (1 mmol) of 1,4-dihydro-2,6-dimethyl-4-(3-nitrophenyl)-5-pyridylpyridine-3-carboxylic acid, 177 mg (1 mmol) of 2-(1,2,3,4-tetrahydroisoquinoline-2-yl)ethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 378 mg (74%).

Melting point: 166° C. (decomposed).

IR (cm$^{-1}$, KBr); $\nu$ CO 1692, $\nu$ NO$_2$ 1532, 1348.

Mass Analysis for C$_{30}$H$_{30}$N$_4$O$_4$: Calculated: 510.2666, Found: 510.22467.

NMR ($\delta$, CDCl$_3$); 1.86 (3H, s), 2.41 (3H, s), 2.74~2.92 (6H, m), 3.64~3.74 (2H, m), 4.24 (1H, dt, J=12 Hz, 6 Hz), 4.29 (1H, dt, J=12 Hz, 6 Hz), 4.81 (1H, s), 5.63 (1H, s), 6.95 (1H, d, J=7.5 Hz), 7.06~7.30 (5H, m), 7.19 (1H, t, J=7 Hz), 7.50 (1H, d, J=7 Hz), 7.94 (1H, d, J=7 Hz), 8.04(1H, s), 8.21 (1H, d, J=2.4 Hz), 8.42 (1H, dd, J=5 Hz, 2.4 Hz).

Example 26

Synthesis of 2-(3,7-dihydro-3,7-dimethyl-2,6-dione-1-yl)ethyl 1,4-dihydro-2,6-dimethyl-4-(3-nitrophenyl)-5-pyridylpyridine-3-carboxylate

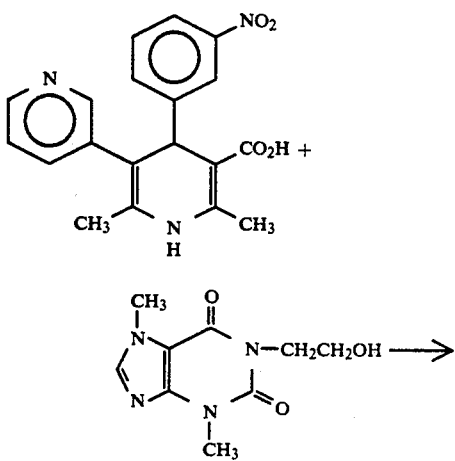

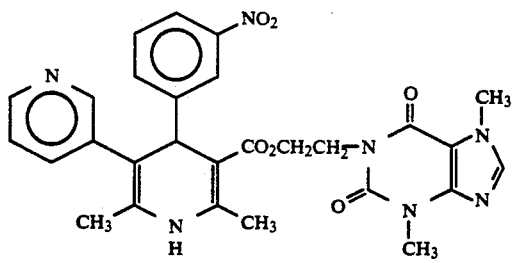

350 mg (1 mmol) of 1,4-dihydro-2,6-dimethyl-4-(3-nitrophenyl)-5-pyridylpyridine-3-carboxylic acid, 224 mg (1 mmol) of 2-(3,7-dihydro-3,7-dimethyl-1H-purine-2,6-dione-1-yl)-ethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 529 mg (95%).

Melting point: 198.1° to 199.9° C.,

IR (cm$^{-1}$, KBr); $\nu$ CO 1708, 1704, 1668, $\nu$ NO$_2$ 1530, 1352.

Mass Analysis for C$_{28}$H$_{27}$N$_7$O$_6$: Calculated: 557.20223, Found: 557.20372.

NMR ($\delta$, CDCl$_3$); 1.89 (3H, s), 2.37 (3H, s), 3.48 (3H, s), 3.87 (3H,s), 4.12~4.27 (2H, m), 4.33~4.49 (2H, m), 4.80 (1H,s), 5 66 (1H, s), 7.22 (1H, dd, J=7 Hz, 2 Hz), 7.28 (1 H, t, J=7.5 Hz), 7.37 (1H, d, J=7.5 Hz), 7.48 (1H, s), 7.52 (1H, d, J=7 Hz), 7.95 (1H, d, J=7.5 Hz), 8.07 (1H, s), 8.27 (1H, s), 8.43 (1H, d, J=2 Hz).

Example 27

Synthesis of 2-(1,2,3,6-tetrahydro-1,3-dimethyl-2,6-dioxo-7H-purine-7-yl)ethyl 1,4-dihydro-2,6-dimethyl-4-(3-nitrophenyl)-5-pyridylpyridine-3-carboxylate

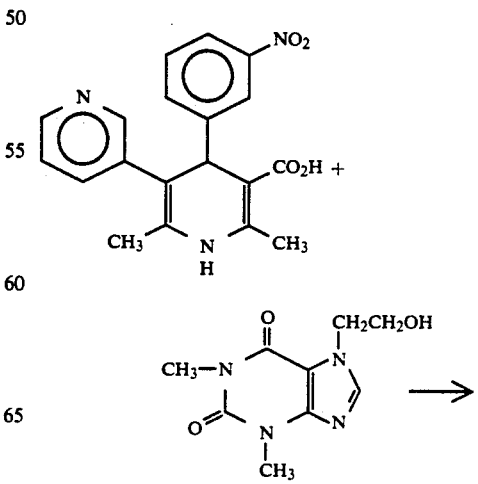

-continued

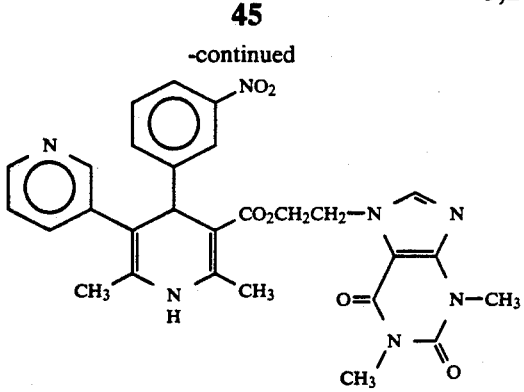

350 mg (1 mmol) of 1,4-dihydro-2,6-dimethyl-4-(3-nitrophenyl)-5-pyridylpyridine-3-carboxylic acid, 224 mg (1 mmol) 1,2,3,6-tetrahydro-1,3-dimethyl-2,6-dioxo-7H-purine-7-yl)ethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 514 mg (92%).

Melting point: 198.6° to 200.4° C.,

IR (cm$^{-1}$, KBr); $\nu$ CO 1700, 1652, $\nu$ NO$_2$ 1528, 1350.

Mass Analysis for $C_{28}H_{27}N_7O_6$: Calculated: 557.20223, Found: 557.20254.

NMR ($\delta$, CDCl$_3$); 1.87 (3H, s), 2.34 (3H, s), 3.38 (3H,s), 3.56 (3H, s), 4.35~4.58 (4H, m), 4.69 (1H, s), 5.74 (1H, s), 7.11 (1H, s), 7.35~7.51 (4H, m), 7.89 (1H, s), 8.04 (1H, d, J=6 Hz), 8.25 (1H, s), 8.47 (1H, d, J=5 Hz).

Example 28

Synthesis of methyl 4-(2,3-dichlorophenyl)-1,4-dihydro-2,6-dimethyl-5-pyridylpyridine-3-carboxylate

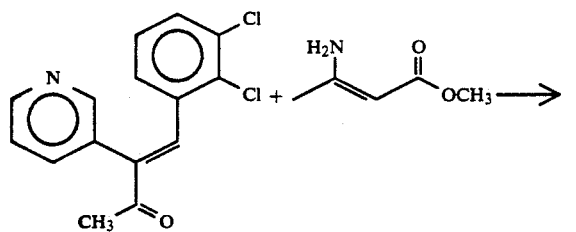

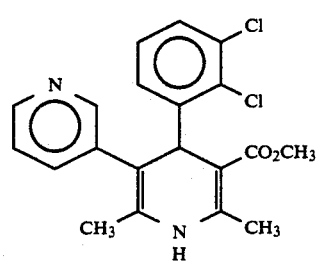

A mixuture of 292 mg (1 mmol) of 4-(2,3-dichlorophenyl)-3-pyridyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 668 mg (85.9%).

Melting point: 158.0° to 159.3° C.

IR (cm$^{-1}$), KBr); $\nu$ CO 1700.

Mass Analysis for $C_{20}H_{18}N_2O_2Cl_2$: Calculated: 388.07450, Found: 388.0756.

NMR ($\delta$, CDCl$_3$); 1.69 (3H, s), 2.41 (3H, s), 3.53 (3H, s), 5.30 (1H, s), 5.41 (1H, s), 7.10~7.26 (4H, m), 7.39 (1H, dd, J=8, 2 Hz), 8.12 (1H, s), 8.41 (1H, d, J=4 Hz).

Example 29

Synthesis of methyl 1,4-dihydro-2,6-dimethyl-5-pyridyl-4-(3-trifluoromethylphenyl)pyridine-3-carboxylate

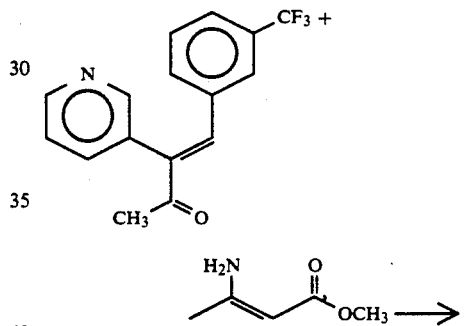

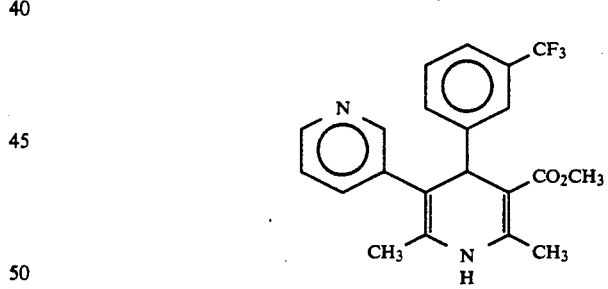

A mixuture of 291 mg [1 mmol] of 3-pyridyl-4-(3-trifluoromethylphenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 361 mg (93.2%).

Melting point: 139° to 140.5° C.,

IR (cm$^{-1}$, KBr); $\nu$ CO 1700.

Mass Analysis for $C_{21}H_{19}F_3N_2O_2$; Calculated: 388.13981, Found: 388.14156.

NMR (δ, CDCl$_3$); 1.85 (3H, s), 2.38 (3H, s), 3.61 (3H, s), 4.70 (1H, s), 5.53 (1H, s), 7.15 (1H, dd, J=8, 5 Hz), 7.24 (1H, dt, J=8, 2 Hz), 7.32~7.41 (4H, m), 8.23 (1H, d, J=2 Hz), 8.41 (1H, dd, J=5, 2 Hz).

Example 30

Synthesis of methyl 4-(2-cyanophenyl)-1,4-dihydro-2,6-dimethyl-5-pyridyl-pyridine-3-carboxylate

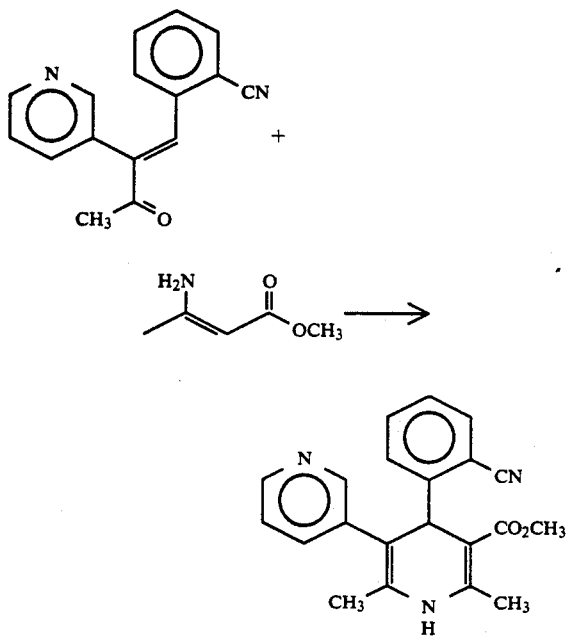

A mixuture of 248 mg (1 mmol) of 4-(2-cyanophenyl)-3-pyridyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 245 mg (71.2%).

Melting point: 142.8° to 143.9° C.

IR (cm$^{-1}$, KBr); ν CN 2225, ν CO 1700.

Mass Analysis for $C_{20}H_{19}N_3O_2$: Calculated: 345.14768, Found: 345.14727.

NMR (δ, CDCl$_3$); 1.74 (3H, s), 2.41 (3H, s), 3.55 (3H, s), 5.12 (1H, s), 5.52 (1H, s), 7.16~7.21 (2H, m), 7.38 (1H, dt, J=8 Hz, 2Hz), 7.41~7.50 (3H, m), 8.01 (1H, d, J=2 Hz), 8.40 (1H, dd, J=5, 2 Hz).

Example 31

Synthesis of methyl 1,4-dihydro-2,6-dimethyl-4-(2-furyl)-5-pyridylpyridine-3-carboxylate

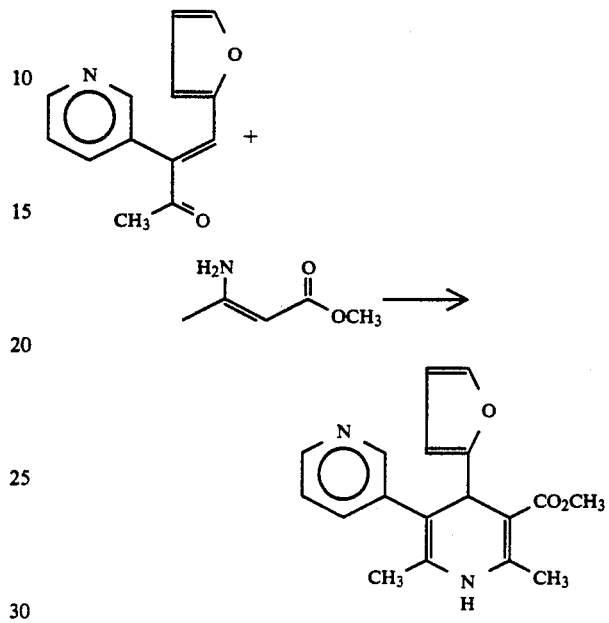

A mixuture of 213 mg (1 mmol) of 4-(2-furyl)-3-pyridyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 230 mg (74.6%).

Melting point: 161.5° to 162.8° C.

IR (cm$^{-1}$, KBr); ν CO 1700.

Mass Analysis for $C_{18}H_{18}N_2O_3$: Calculated: 310.13171, Found: 310.13160.

NMR (δ, CDCl$_3$); 1.87 (3H,s), 2.38 (3H,s), 3.66 (3H, s), 4.78 (1H,s), 5.69 (1H, s), 5.93 (1H, d, J=3 Hz), 6.22 (1H, dd, J=2, 3 Hz), 7.20 (1H, dd, J=8, 4 Hz), 7.26 (1H, d, J=2 Hz), 7.42 (1H, d, J=8 Hz), 8.37 (1H, s), 8.43 (1H, d, J=4 Hz).

Example 32

Synthesis of methyl 1,4-dihydro-2,6-dimethyl-5-pyridyl-4-thienylpyridine-3-carboxylate

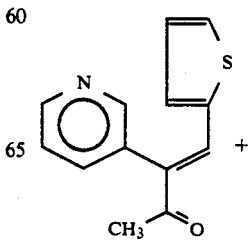

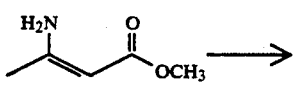

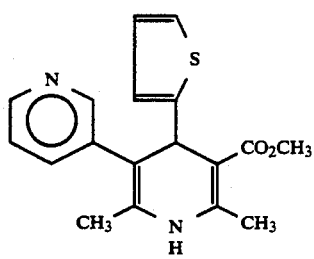

A mixuture of 229 mg (1 mmol) of 3-pyridyl-4-thienyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 173 mg (53%).

Melting point: 198.0° to 199.0° C.

IR (cm$^{-1}$, KBr); $\nu$ CO 1670.

Mass Analysis for $C_{18}H_{18}N_2O_2S$: Calculated: 326.10886, Found: 326.10847.

NMR ($\delta$, CDCl$_3$); 1.93 (3H,s), 2.35 (3H, s), 3.69 (3H, s), 4.69 (1H, s), 5.66 (1H, s), 6.75 (1H, d, J=4 Hz), 6.85 (1H, dd, J=5, 4 Hz), 7.08 (1H, dd, J=6 Hz), 7.18 (1H, dd, J=7, 5 Hz), 7.43 (1H, d, J=7 Hz), 8.41 (1H, s), 8.43 (1H, d, J=5 Hz).

Example 33

Synthesis of methyl 1,4-dihydro-2,6-dimethyl-4,5-dipyridylpyridine-3-carboxylate

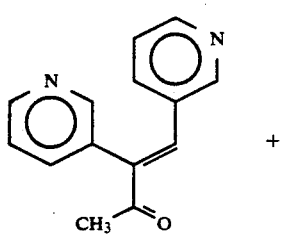

+

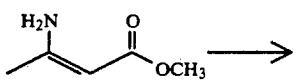

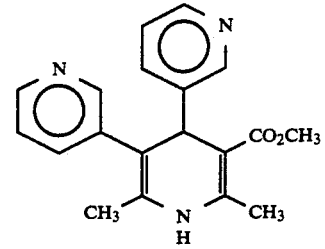

A mixuture of 224 mg (1 mmol) of 3,4-dipyridyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 269 mg (83.8%).

Melting point: 189.7° to 190.8° C.

IR (cm$^{-1}$, KBr); $\nu$ CO 1700.

Mass Analysis for $C_{19}H_{19}N_3O_2$: Calculated: 321.14768, Found: 321.14711.

NMR ($\delta$, CDCl$_3$); 1.84 (3H, s), 2.37 (3H, s), 3.61 (3H, s), 4.65 (1H, s), 5.94 (1H, s), 7.14 (1H, t, J=7 Hz), 7.15 (1H, dd, J=8, 6 Hz), 7.26 (1H, d, J=7 Hz), 7.49 (1H, d, J=8 Hz), 8.26 (1H, s), 8.39 (1H, d, J=6 Hz), 8.41 (1H, d, J=7 Hz), 8.44 (1H, s).

Example 34

Synthesis of methyl 1,4-dihydro-2,6-dimethyl-5-pyridyl-4-(4-quinolyl)pyridine-3-carboxylate

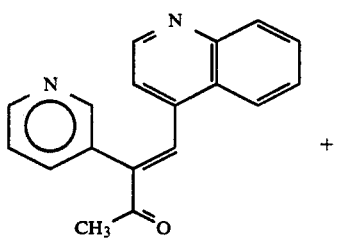

+

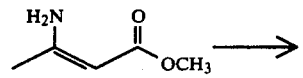

A mixuture of 274 mg (1 mmol) of 3-pyridyl-4-quinolyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 324 mg (87.5%).

Melting point: 189° C. (decomposed).

Mass Analysis for $C_{23}H_{21}N_3O_2$: Calculated: 371.16333, Found: 371.16350.

NMR (δ, CDCl$_3$; 1.76 (3H, s), 2.46 (3H, s), 3.39 (3H, s), 5.51 (1H, s), 5.63 (1H, s), 6.94 (1H, dd, J=7, 5 Hz), 6.99 (1H, dt, J=7, 2 Hz), 7.31 (1H, t, J=8 Hz), 7.49 (1H, d, J=5 Hz), 7.56 (1H, t, J=8 Hz), 7.89 (1H, d, J=8 Hz), 8.00 (1H, d, J=8 Hz), 8.17 (1H, s), 8.30 (1H, dd, J=5,2 Hz), 8.84 (1H, d, J=5 Hz).

Example 35

Synthesis of 3-cyano-1,4-dihydro-2,6-dimethyl-4-(3-nitrophenyl)-5-pyridylpyridine

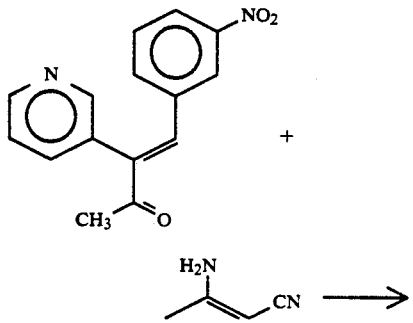

A mixuture of 0.536 g (2 mmol) of 4-(3-nitrophenyl)-3-pyridyl-3-butene-2-one, 0.821 g (10 mmol) of 3-aminocrotonitrile, 0.546 g (4 mmol) of zinc chloride, and 1.0 g of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 0.59 g (84.6%).

Melting point: 202.8° to 204.3° C.

IR (cm$^{-1}$, KBr); ν CN 2192, ν NO$_2$ 1530, 1350.

Mass Analysis for $C_{19}H_{16}N_4O_2$: Calculated: 332.12729, Found: 332.12685.

NMR (δ, CDCl$_3$); 1.84 (1.84 (3H,s), 2.17 (3H,s), 4.53 (1H,s), 5.81 (1H,s), 7.19(1H, dd, J=8, 5 Hz), 7.28 (1H, dt, J=8, 2 Hz), 7.42 (1H, d, J=2 Hz), 7.44 (1H,s), 8.07 (1H, t, J=2 Hz), 8.09 (1H, d, J=2 Hz), 8.22 (1H, d, J=2 Hz), 8.42 (1H, dd, J=5, 2 Hz).

Example 36

Synthesis of 3-acetyl-1,4-dihydro-2,6-dimethyl-4-(3-nitrophenyl)-5-pyridylpyridine

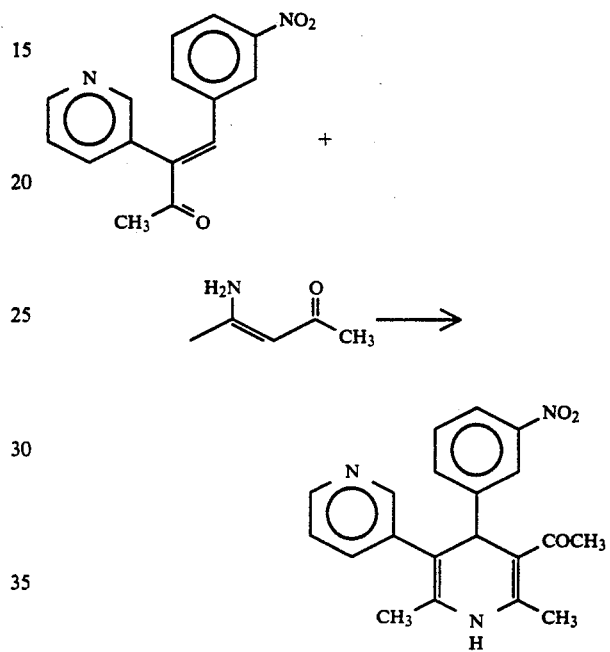

A mixuture of 268 mg (1 mmol) of 4-(3-nitrophenyl)-3-pyridyl-3-butene-2-one, 495 mg (5 mmol) of 4-amino-3-pentene-2-one, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture wa then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 121 mg (34.7%).

Melting point: 160.7° to 161.9° C.

IR (cm$^{-1}$, KBr); ν NO$_2$ 1530, 1350.

Mass Analysis for $C_{20}H_{19}N_3O_3$: Calculated: 349.14260, Found: 359.14312.

NMR (δ, CDCl$_3$); 1.86 (3H, s), 1.98 (3H, s), 2.42 (3H, s), 4.86 (1H, s), 5.96 (1H, s), 7.22 (1H, dd, J=8, 5 Hz), 7.31 (1H, d, J=8 Hz), 7.35 (1H, t, J=8 Hz), 7.43 (1H, d, J=8 Hz), 8.00 (1H, s), 8.01 (1H, d, J=8 Hz), 8.23 (1H, s), 8.45 (1H, d, J=5 Hz).

Example 37

Synthesis of 3-benzoyl-1,4-dihydro-2,6-dimethyl-4-(3-nitrophenyl)-5-pyridylpyridine

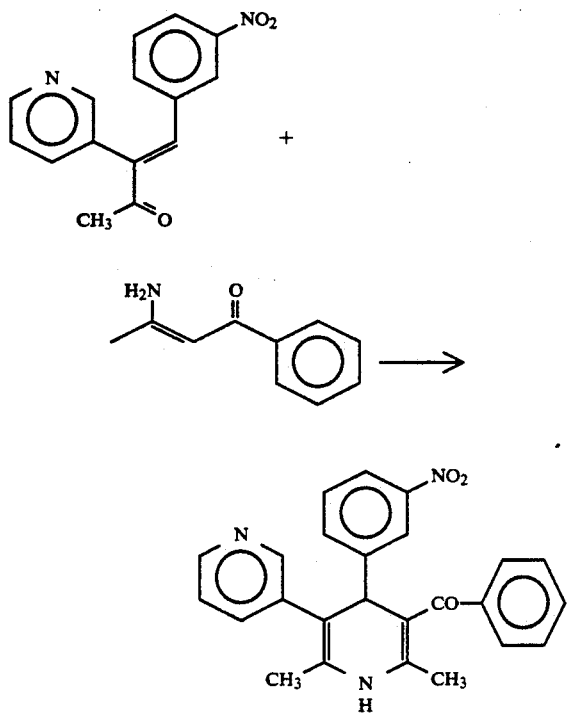

A mixuture of 0.536 g (2 mmol) of 4-(3-nitrophenyl)-3-pyridyl-3-butene-2-one, 0.161 g (10 mmol) of 3-amino-1-phenyl-2-butene-1-one, 0.546 g (4 mmol) of zinc chloride, and 1 g of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 0.424 g 51.7%).

Melting point: 172.9° to 173.8° C.

IR (cm$^{-1}$, KBr); $\nu$ NO$_2$ 1530, 1350.

Mass Analysis for C$_{25}$H$_{21}$N$_3$O$_3$: Calculated: 411.15825, Found: 411.15588.

NMR ($\delta$, CDCl$_3$); 1.85 (3H, s), 1.98 (3H, s), 4.99 (1H, s), 5.71 (1H, s), 7.25~7.47 (8H, m), 7.48 (1H, d, J=8 Hz), 8.00 (1H, d, J=8 Hz), 8.06 (1H, s), 8.32 (1H, s), 8.43 (1H, d, J=5 Hz).

Example 38

Synthesis of methyl 5-(6-chloropyridyl)-1,4-dihydro-2,6-dimethyl-4-(3-nitrophenyl)pyridine-3-carboxylate

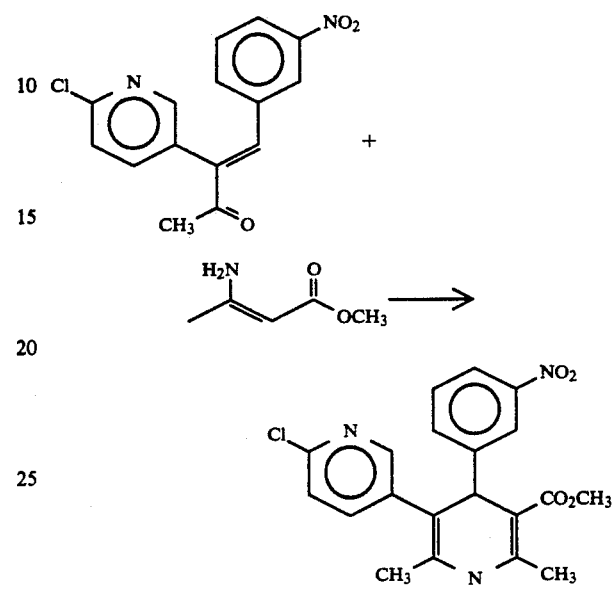

A mixuture of 303 mg (1 mmol) of 3-(6-chloropyridyl)-4-(3-nitrophenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 229 mg (57.5%).

Melting point: 122.5° to 124.0° C.

IR (cm$^{-1}$, KBr); $\nu$ CO 1680, $\nu$ NO$_2$ 1530, 1350.

Mass Analysis for C$_{20}$H$_{18}$ClN$_3$O$_4$: Calculated: 399.09854, Found: 399.09642.

NMR ($\delta$, CDCl$_3$); 1.86 (3H, s), 2.39 (3H, s), 3.62 (3H, s), 4.74 (1H, s), 5.58 (1H, s), 7.19 (1H, d, J=7 Hz), 7.22 (1H, d, J=7 Hz), 7.36 (1H, t, J=8 Hz), 7.45 (1H, d, J=8 Hz), 7.99 (1H, s), 8.02 (1H, d, J=8 Hz) 8.06 (1H, s).

Example 39

Synthesis of methyl 5-(2-chloropyridyl)-1,4-dihydro-2,6-dimethyl-4-(3-nitrophenyl)pyridine-3-carboxylate

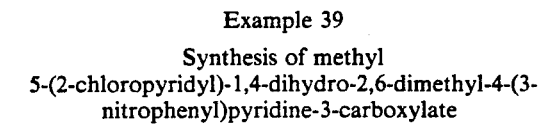

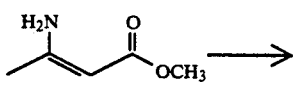

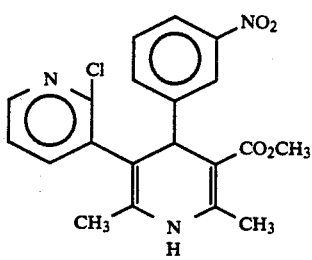

A mixuture of 303 mg (1 mmol) of 3-(2-chloropyridyl)-4-(3-nitrophenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 204 mg (51%).

Melting point: oil,

IR (cm$^{-1}$, KBr); $\nu$ CO 1698, $\nu$ NO$_2$ 1532, 1350.

Mass Analysis for C$_{20}$H$_{18}$ClN$_3$O$_4$: Calculated: 399.09547, Found: 399.10099.

NMR ($\delta$, CDCl$_3$): measured at a temperature of 100° C., using cyclosilan-d$_{18}$ ($\delta$=−0.327) as an internal standard. 1.58 (3H,s), 2.31 (3H, s), 3.43 (3H, s), 4.73 (1H, s), 6.90~7.33 (2H, m), 7.33~7.48 (2H, m), 7.75 (1H, s), 7.91 (1H, d, J=8 Hz), 8.19 (2H, m).

Example 40

Synthesis of methyl 1,4-dihydro-2,6-dimethyl-5-(6-methoxypyridyl)-4-(3-nitrophenyl)pyridine-3-carboxylate:

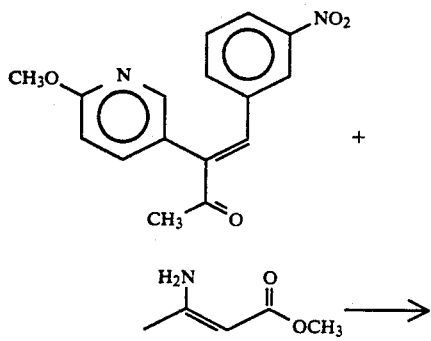

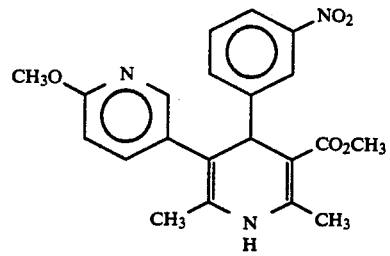

A mixuture of 298 mg (1 mmol) of 3-(6-methoxypyridyl)-4-(3-nitrophenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained The yield was 290 mg (74.5%).

Melting point: oil.

IR (cm$^{-1}$, KBr); $\nu$ CO 1695, $\nu$ NO$_2$ 1530, 1350.

Mass Analysis for C$_{21}$H$_{21}$N$_3$O$_5$; Calculated: 395.14808, Found: 395.14987.

NMR ($\delta$, CDCl$_3$); 1.85 (3H, s), 2.38 (3H, s), 3.60 (3H, s), 3.88 (3H, s), 4.72 (1H, s), 5.51 (1H, s), 6.62 (1H, d, J=8 Hz), 7.16 (1H, dd, J=8, 2 Hz), 7.34 (1H, t, J=8 Hz), 7.48 (1H, d, J=8 Hz), 7.71(1H, d, J=2 Hz), 8.090 (1H, d, J=8 Hz), 8.06 (1H, s).

Example 41

Synthesis of methyl 1,4-dihydro-2,6-dimethyl-5-(2-methoxyphenyl)-4-(3-nitrophenyl)pyridine-3-carboxylate

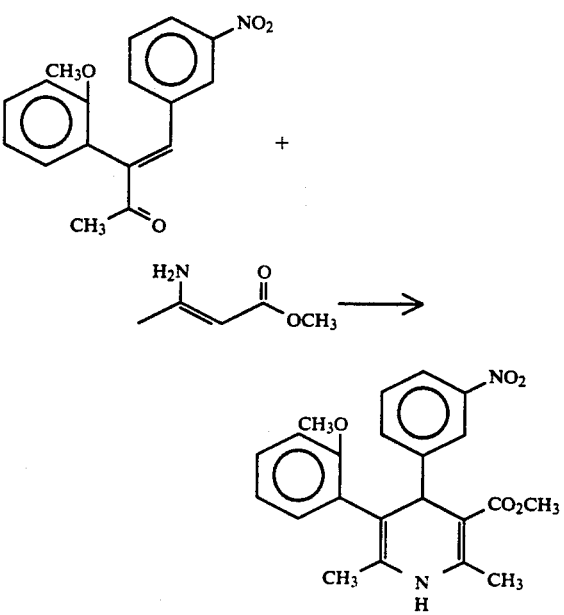

A mixuture of 297 mg (1 mmol) of 3-(2-methoxyphenyl)-4-(3-nitrophenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 216 mg (55%).

Melting point: 176.4° to 177.7° C.

(cm$^{-1}$KBr); $\nu$ NB 3370, CO 1705, $\nu$ NO$_2$ 1535, 1345.

Mass Analysis for C$_{22}$; H$_{22}$N$_2$O$_5$: Calculated: 394.15283, Found: 394.15187.

NMR ($\delta$, CDCl$_3$); 1.70 (3H, bs), 2.40 (3H, s), 3.57 (3H, s), 3.74~3.97 (3H, b), 4.82 (1H, bs), 5.42 (1H, bs), 6.60~6.92 (4H, b), 7.16 (1H, td, J=8 Hz, 2Hz), 7.25 (1H, t, J=8 Hz), 7.36 (1H, d, J=8 Hz), 7.57 (1H, d, J=8 Hz), 8.01 (1H, s).

Example 42

Synthesis of methyl 1,4-dihydro-2,6-dimethyl-5-(2-fluorophenyl)-4-(3-nitrophenyl)pyridine-3-carboxylate

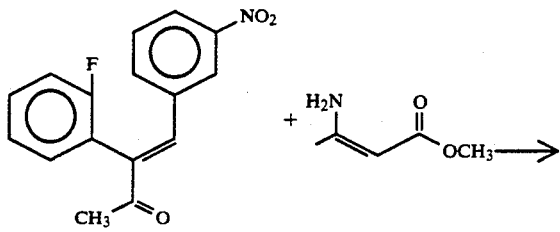

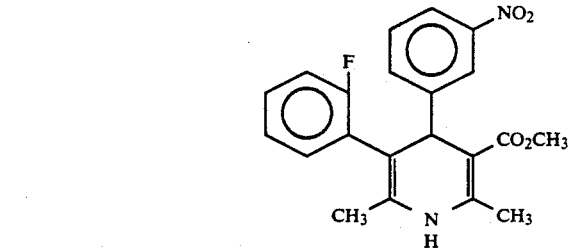

A mixuture of 285 mg (1 mmol) of 3-(2-fluorophenyl)-4-(3-nitrophenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 242 mg (63%).

Melting point: 153.0° to 153.1° C.

IR (cm$^{-1}$, KBr); $\nu$ NH 3360, CO 1690, $\nu$ NO$_2$ 1535, 1345,

Mass Analysis for C$_{21}$H$_{19}$FN$_2$O$_4$: Calculated: 382.13284, Found: 382.13492.

NMR ($\delta$, CDCl$_3$); 1.73 (3H, s), 2.39 (3H, s), 3.58 (3H, s), 4.79 (1H, s), 5.40 (1H, bs), 6.81~6.90 (1H, b), 6.92~7.02 (2H, m), 7.13~7.22 (1H, m), 7.27 (1H, t, J=8 Hz), 7.41 (1H, d, J=8 Hz), 7.94 (1H, ddd, J=8 Hz), 2 Hz, 1 Hz), 8.00 (1H, t, J=2 Hz).

Example 43

Synthesis of methyl 1,4-dihydro-2,6-dimethyl-4(3-nitrophenyl)-5-thienylpyridine-3-carboxylate

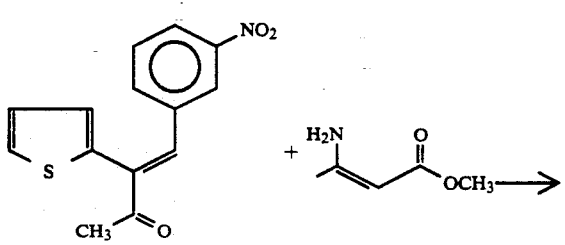

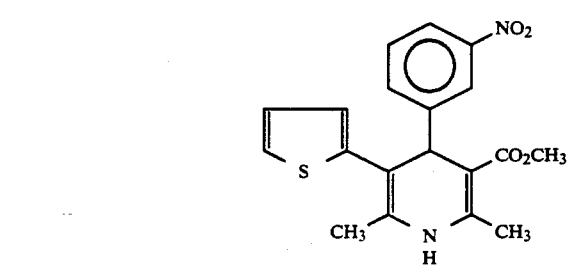

A mixuture of 273 mg (1 mmol) of 4-(3-nitrophenyl)-3-thienyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 206 mg (61%).

Melting point: 144.2° to 144.4° C.

IR (cm$^{-1}$, KBr); $\nu$ NB 3370, CO 1650, $\nu$ NO$_2$ 1550, 1355.

Mass Analysis for C$_{19}$H$_{18}$N$_2$O$_2$S: Calculated: 338.10886, Found: 338.10655.

NMR ($\delta$, CDCl$_3$); 2.11 (3H, s), 2.37 (3H, s), 3.65 (3H, s), 4.88 (1H, s), 5.57 (1H, bs), 6.66 (1H, dd, J=4 Hz, 1 Hz), 6.88 (1H, dd, J=5 Hz, 4 Hz), 7.12 (1H, dd, J=5 Hz, 1 Hz), 7.38 (1H, t, J=8 Hz), 7.62 (1H, dt, J=8 Hz, 1 Hz), 8.02 (1H, ddd, J=8 Hz, 2 Hz, 1 Hz), 8.14 (1H, t, J=2 Hz).

Example 4

Synthesis of methyl 1,4-dihydro-2,6-dimethyl-5-(2-furyl)-4-(3-nitrophenyl)-pyridine-3-carboxylate

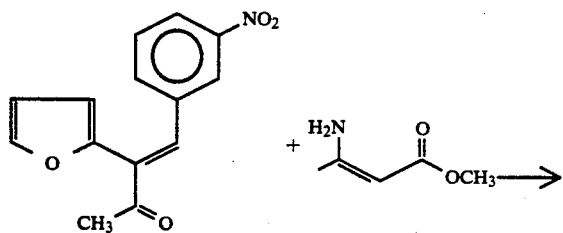

A mixuture of 257 mg (1 mmol) of 3-(2-furyl)-4-(3-nitrophenyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture wa refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 289 mg (82%).

Melting point: 173.2° to 173.9° C.

IR (cm$^{-1}$, KBr); $\nu$ NB 3370, CO 1650, $\nu$ NO$_2$ 1530, 1350.

Mass Analysis for C$_{19}$H$_{18}$N$_2$O$_5$: Calculated: 354.12154, Found: 354.12038.

NMR ($\delta$, CDCl$_3$); 2.27 (3H, s), 2.36 (3H,s), 3.68 (3H, s), 5.02 (1H, s), 5.59 (1H, bs), 6.07 (1H, d, J=3 Hz), 6.31 (1H, dd, J=3 Hz, 2 Hz), 7.31 (1H, d, J=2 Hz), 7.37 (1H, t, J=8 Hz), 7.99 (1H, ddd, J=8 Hz, 2 Hz, 1 Hz), 8.15 (1H, t, J=2 Hz).

Example 45

Synthesis of methyl 1,4-dihydro-2,6-dimethyl-4-(3-nitrophenyl-5-pyridazinylpyridine-3-carboxylate

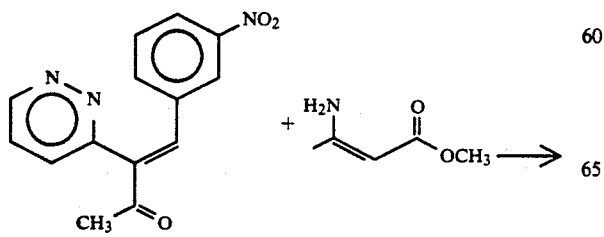

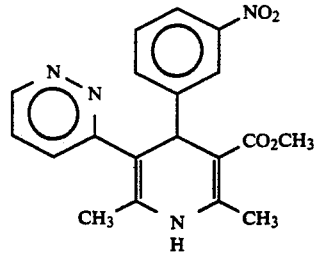

A mixuture of 213 mg (0.84 mmol) of 4-(3-nitrophenyl)-3-pyridazinyl-3-butene-2-one, 484 mg (4.2 mmol) of methyl 3-aminocrotonate, 343 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 280 mg (91%).

Melting point: 94.8° C.

IR (cm$^{-1}$, KBr); $\nu$ CO 1680, $\nu$ NO$_2$, 1528, 1348.

Mass Analysis for C$_{19}$H$_{18}$N$_4$O$_4$: Calculated: 366.13277, Found: 366.13126.

NMR ($\delta$, CDCl$_3$); 2.18 (3H, s), 2.40 (3H, s), 3.66 (3H, s), 5.25 (1H, s), 6.04 (1H, s), 7.23 (1H, dd, J=8.6 Hz, 2.4 Hz), 7.34 (1H, dd, J=8.6 Hz, 5.1 Hz), 7.35 (1H. t, J=7.8 Hz), 7.61 (1H, d, J=7.8 Hz), 7.98 (1H, d, J=7.8 Hz), 8.12 (1H, s), 8.98 (1H, dd, J=5, 1 Hz, 1.5 Hz).

Example 46

Synthesis of methyl 1,4-dihydro-2,6-dimethyl-4-(3-nitrophenyl)-5-(3-quinolyl)pyridine-3-carboxylate

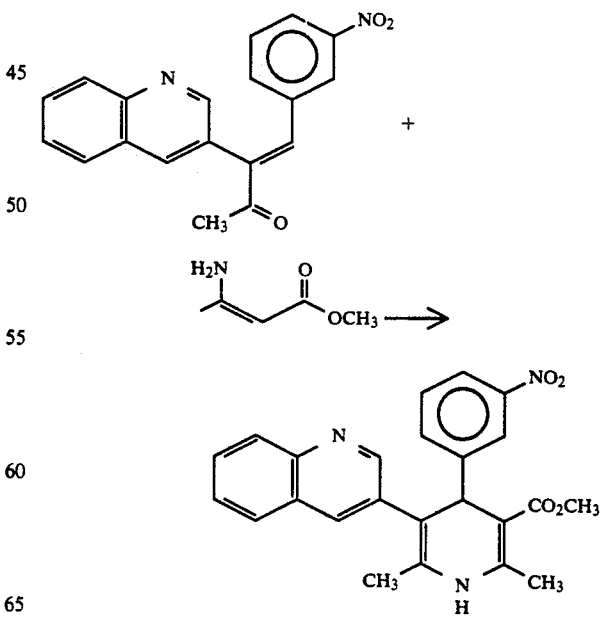

A mixuture of 302 mg (1 mmol) of 4-(3-nitrophenyl)-3-(3-quinolyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 300 mg (80.8%).

Melting point: 115° C.

IR (cm$^{-1}$, KBr); $\nu$ CO, 1695, $\nu$ NO$_2$ 1530, 1350.

Mass Analysis for $C_{24}H_{21}N_3O_4$: Calculated: 415.15316, Found: 415.15316, NMR ($\delta$, CDCl$_3$); 1.93 (3H, s), 2.43 (3H, s), 3.63 (3H, s), 4.92 (1H, s), 5.64 (1H, s), 7.33 (1H, t, J=8 Hz), 7.47 (1H, d, J=8 Hz), 7.52 (1H, t, J=8 Hz), 7.67~7.74 (3H, m), 8.01 (1H, d, J=8 Hz), 8.09 (1H, d, J=8 Hz), 8.12 (1H,s), 8.57 (1H, d, J=2 Hz).

Example 47

Synthesis of methyl 1,4-dihydro-2,6-dimethyl-4(3-nitrophenyl)-5-pyrazinyl-pyridine-3-carboxylate

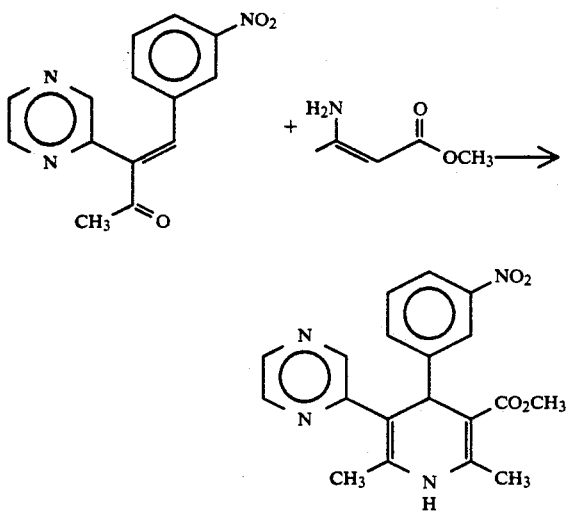

A mixuture of 253 mg (1 mmol) of 4-(3-nitrophenyl)-3-pyrazinyl-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 271 mg (77.3%).

Melting point: 134.9° to 136.1° C.

IR (cm$^{-1}$, KBr); $\nu$ CO, 1670, $\nu$ NO$_2$ 1530, 1350.

Mass Analysis for $C_{19}H_{18}N_4O_4$: Calculated: 366.13277, Found: 366.13473.

NMR ($\delta$, CDCl$_3$); 2.18 (3H,s), 2.40 (3H, s), 3.66 (3H, s), 5.25 (1H, s), 5.68 (1H, s), 7.35 (1H, t, J=8 Hz), 7.59 (1H, d, J=8 Hz), 7.97 (1H, d, J=8 Hz), 8.10 (1H, s), 8.30 (1H, d, J=8 Hz), 8.34 (1H, d, J=2 Hz), 8.51 (1H, dd, J=3, 2 Hz).

Example 48

Synthesis of methyl 1,4-dihydro-2,6-dimethyl-4-(3-nitrophenyl)-5-(2-pyridyl)pyridine-3-carboxylate

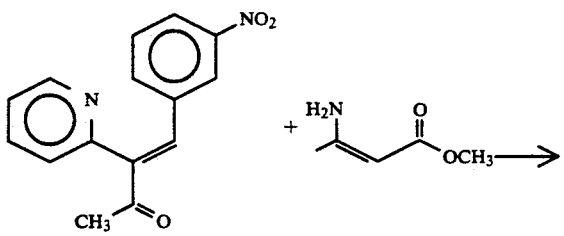

A mixuture of 268 mg (1 mmol) of 4-(3-nitrophenyl)-3-(2-pyridyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 292 mg (80%).

Melting point: 156.6° to 158.1° C.

IR (cm$^{-1}$, KBr): $\nu$ NH 3340, CO 1665, $\nu$ NO$_2$ 1535, 1345.

Mass Analysis for $C_{20}H_{19}H_3O_4$: Calculated: 365.13751, Found: 365.13973.

NMR ($\delta$, CDCl$_3$); 2.07 (3H, s), 2.39 (3H, s), 3.63 (3H, s), 5.23 (1H, s), 5.54 (1H, s), 6.97 (1H, d, J=8 Hz), 7.05 (1H, dd, J=8 Hz, 5 Hz), 7.31 (1H, t, J=8 Hz), 7.50 (1H, td, J=8 Hz, 2 Hz), 7.53 (1H, d, J=8 Hz), 7.95 (1H, dt, J=8 Hz, 2 Hz), 8.07 (1H, t, J=2 Hz), 8.55 (1H, d, J=5 Hz).

Example 49

Synthesis of methyl 1,4-dihydro-2,6-dimethyl-4-(3-nitrophenyl)-5-(4-pyridyl)pyridine-3-carboxylate

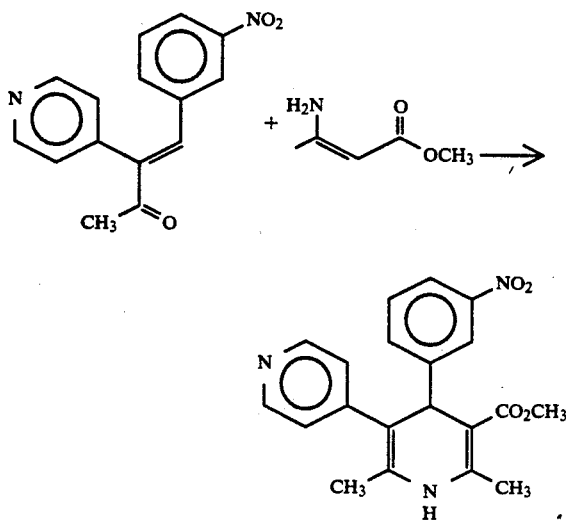

A mixuture of 268 mg (1 mmol) of 4-3-nitrophenyl)-3-(4-pyridyl)-3-butene-2-one, 575 mg (5 mmol) of methyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 300 mg (82%).

Melting point: 165° C. (decomposed),

IR (cm$^{-1}$, KBr); $\nu$ CO 1680, $\nu$ NO$_2$ 1530, 1350,

Mass Analysis for C$_{20}$H$_{19}$N$_3$O$_4$: Calculated: 365.13751, Found: 365.13897.

NMR ($\delta$, CDCl$_3$); 1.95 (3H, s), 2.39 (3H, s), 3.64 (3H, s), 4.86 (1H, s), 5.61 (1H, s), 6.93 (2H, dd, J=5 Hz, 2 Hz), 7.34 (1H, t, J=8 Hz), 7.47 (1H, d, J=8 Hz), 8.00 (1 H, ddd, J=8 Hz, 2 Hz, 1 Hz), 8.07 (1H, t, J=2 Hz), 8.45 (2H, dd, J=5 Hz, 2 Hz).

Example 50

Synthesis of 2-(N-benzyl-N-methylamino)ethyl 1,4-dihydro-2,6-dimethyl-4-(3-nitrophenyl)-5-(4-pyridyl)pyridine-3-carboxylate

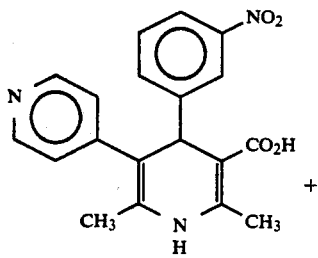

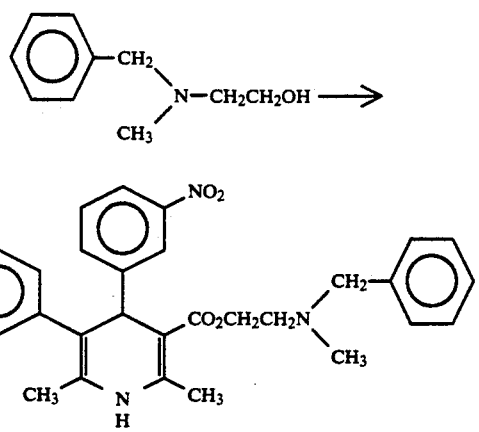

350 mg (1 mmol) of 1,4-dihydro-2,6-dimethyl-4-(3-nitrophenyl)-5-(4-pyridyl)pyridine-3-carboxylic acid, 165 mg (1 mmol) of 2-(N-benzyl-N-methylamino)ethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 502 mg (100%).

Melting point: oil.

IR (cm$^1$, KBr): $\nu$ CO 1695, $\nu$ NO$_2$ 1530, 1350.

Mass Analysis for C$_{29}$H$_{30}$N$_4$O$_4$: Calculated: 498.22666, Found: 488.22850.

NMR ($\delta$, CDCl$_3$); 1.94 (3H, s), 2.20 (3H, s), 2.38 (3H, s), 2.58 (1H, dd, J=9, 6 Hz), 2.65 (1H, dd, J=9, 5 Hz), 3.49 (2H, s), 4.16 (2 H, t, J=6 Hz), 4.85 (3H, s), 5.65 (1H, s), 6.91 (2H, d, J=7 Hz), 7.15~7.30 (6H, m), 7.46 (1H, d, J=8 Hz), 7.97 (1H, d, J=8 Hz), 8.07 (1H, s), 8.45 (2H, d, J=7 Hz).

Example 51

Synthesis of (E)-3-phenyl-2-propene-1-yl 1,3-dihydro-2,6-dimethyl-4-(3-nitrophenyl)-5-(4-pyridyl)pyridine-3-carboxylate

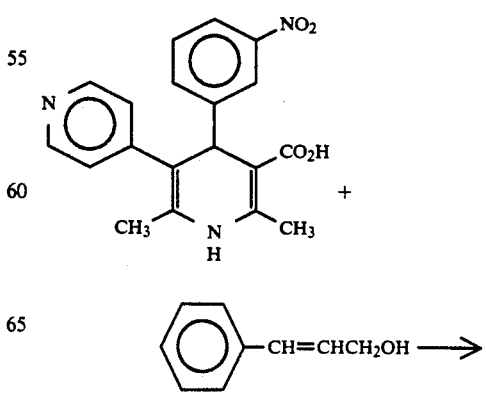

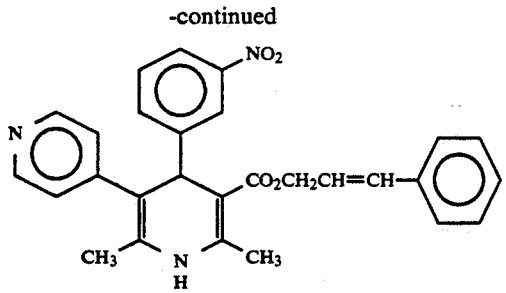

700 mg (2 mmol) of 1,4-dihydro-2,6-dimethyl-4-(3-nitrophenyl)-5-(4-pyridyl)pyridine-3-carboxylic acid was suspended in 10 ml of anhydrous tetrahydrofuran in an atmosphere of an inert gas (Ar), to which was added 220 mg (2.2 mmol) of triethylamine. To the resulting mixture, 228 mg (2.1 mmol) of ethylchloroformate was added dropwise while cooling with ice. After stirring the mixture for 30 minutes, 268 mg (2 mmol) of (E)-3-phenyl-2-propene-1-ol was added to the mixture while cooling with ice, followed by agitation for 2.5 hours. The reaction mixture was then washed with a saturated saline solution and dried over anhydrous sodium sulfate. Tetrahydrofluran contained in the reaction mixture was then distilled off and the residue was chromatographed on a silica gel column, whereby the captioned compound was obtained. The yield was 280 mg (30%).

Melting point: 158.0° to 159.5° C.

IR (cm$^{-1}$, KBr); $\nu$ CO 1698, $\nu$ NO$_2$ 1530, 1350.

Mass Analysis for C$_{28}$H$_{25}$N$_3$O$_4$: Calculated: 467.18446, Found: 467,18453.

NMR ($\delta$, CDCl$_3$); 1.94 (3H, s), 2.41 (3H,s), 4.67 (1H, dd, J=12, 7 Hz), 4.75 (1H, dd, J=12, 7 Hz), 4.89 (1H, s), 5.69 (1H, s), 6.23 (1H, dt, J=15, 5 Hz), 6.54 (1H, d, J=1 Hz), 6.91 (2H, d, J=7 Hz), 7.25~7.36 (6H, m), 7.49 (1H, d, J=8 Hz), 8.00 (1H, d, J=8 Hz), 8.10 (1H, s), 8.44 (2H, d, J=7 Hz).

Example 52

Synthesis of 2-(4-phenylpiperazinyl)ethyl 1,4-dihydro-2,6-dimethyl-4-(3-nitrophenyl)-5-(4-pyridyl)pyridine-3-carboxylate:

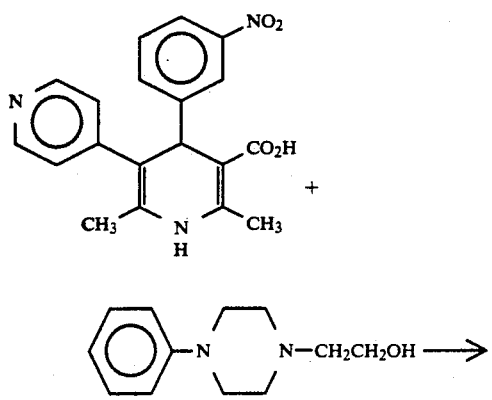

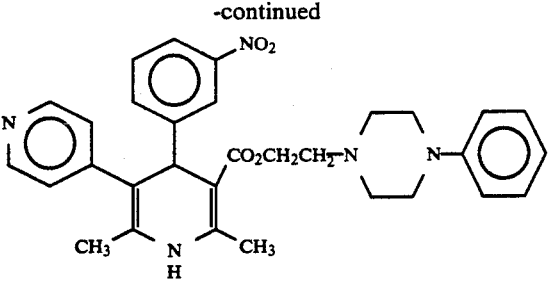

350 mg (1 mmol) of 1,4-dihydro-2,6-dimethyl-4-(3-nitrophenyl)-5-(4-pyridyl)pyridine-3-carboxylic acid, 206 mg (1 mmol) of 2-(4-phenylpiperazinyl)ethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 471 mg (100%).

Melting point: oil.

IR (cm$^{-1}$, KBr); $\nu$ CO 1694, $\nu$ NO$_2$ 1532, 1350.

Mass Analysis for C$_{31}$H$_{33}$N$_5$O$_4$: Calculated: 539.25321, Found: 539.25378, NMR ($\delta$, CDCl$_3$); 1.94 (3H, s), 2.41 (3H, s), 2.50~2.82 (6 H, m), 310–3.27 (4H, m), 4.20~4.40 (2H, m), 4.88 (1H,s), 5.66 (1H, s), 6.85~6.98 (4H, m), 7.23~7.32 (5H,m), 7.34 (1H, t, J=7 Hz), 7.49 (1H, d, J=7 Hz), 8.00 (1H, d, J=7 Hz), 8.06 (1H, s), 8.46 (1H, d, J=6.3 Hz).

Example 53

Synthesis of 2-propene-1-y 1,4-dihydro-2,6-dimethyl-4-(3-nitrophenyl)-5-(4-pyridyl)pyridine-3-carboxylate

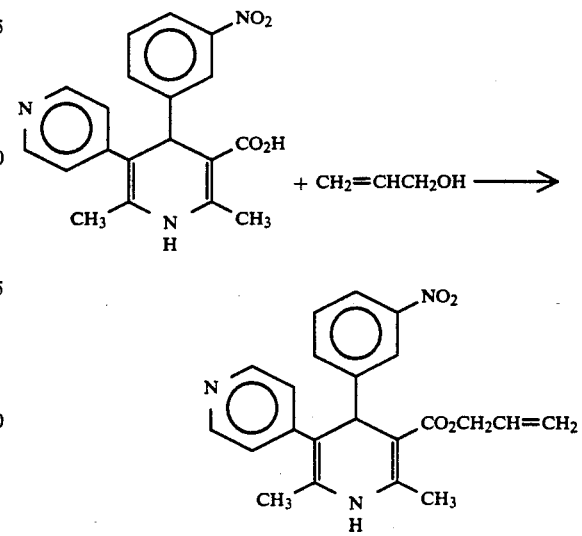

350 mg (1 mmol) of 1,4-dihydro-2,6-dimethyl-4-(3-nitrophenyl)-5-(4-pyridyl)pyridine-3-carboxylic acid, 58 mg (1 mmol) of 2-propene-1-ol, 309 mg [1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 390 mg (100%)

Melting point: 185.3° to 186.7° C.

IR (cm$^{-1}$, KBr); $v$ CO 1696, $v$ NO$_2$ 1526, 1348.

Mass Analysis for C$_{22}$H$_{21}$N$_3$O$_4$: Calculated: 391.15317, Found: 391.15342.

NMR ($\delta$, CDCl$_3$); 2.08 (3H, s), 2.41 (3H, s), 4.54 (1H, dd, J=13 Hz, 6 Hz), 4.62 (1H, dd, J=13 Hz, 6 Hz), 4.94 (1H, s), 5.20 (1H, dd, J=10 Hz, 2 Hz), 5.22 (1H, dd, J=19 Hz, 2 Hz), 5.82~5.97 (1H, m), 5.90 (1H, s), 7.17 (2H, d, J=6 Hz), 7.38 (1H, t, J=7.8 Hz), 7.51 (1H, d, J=7.8 Hz), 8.04 (1H, d, J=7.8 Hz), 8.09 (1H, s), 8.46 (1H, d, J=6 Hz).

Example 54

Synthesis of 2-(phenoxy)ethyl 1,4-dihydro-2,6-dimethyl-4-(3-nitrophenyl)-5-(4-pyridyl)pyridine-3-carboxylate

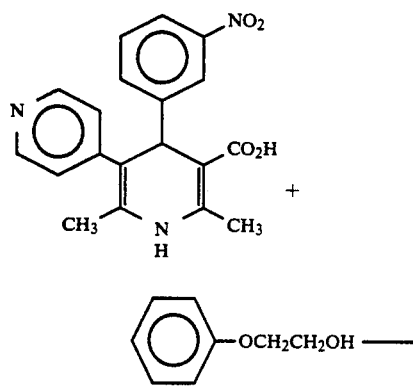

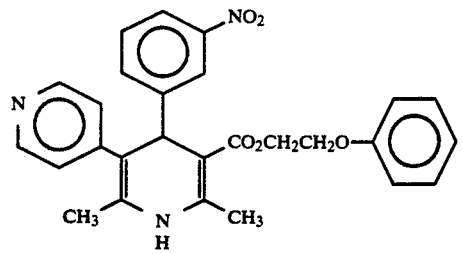

350 mg (1 mmol) of 1,4-dihydro-2,6-dimethyl-4-(3-nitrophenyl)-5-(4-pyridyl)pyridine-3-carboxylic acid, 138 mg (1 mmol) of 2-(phenoxy)ethanol, 309 mg (1.5 mmol) of N,N'-dicyclohexylcarbodiimide, 134 mg (1.1 mmol) of 4-N,N-dimethylaminopyridine were dissolved in 10 ml of toluene, with application of heat thereto. This reaction mixture was refluxed with application of heat for 1 hour, and then cooled to room temperature. To this reaction mixture, 20 ml of chloroform was added. The reaction mixture was then washed with water and dried over anhydrous sodium sulfate. The solvents contained in the reaction mixture were then distilled off and the residue was chromatographed on a silica gel column, whereby the captioned compound was obtained. The yield was 540 mg (100%).

Melting point: 80° C.,

IR (cm$^{-1}$, KBr); $v$ CO 1698, $v$ NO$_2$ 1528, 1350.

Mass Analysis for C$_{27}$H$_{25}$N$_3$O$_5$: Calculated: 471.17938, Found: 471.18037.

NMR ($\delta$, CDCl$_3$); 1.97 (3H, s), 2.40 (3H, s), 4.03~4.18 (2H, m), 4.30~4.39 (1H,m), 4.42~4.52 (1H, m), 4.87 (1H, s), 5.78 (1H, s), 6.85 (2H, d, J=7 Hz), 6.93~7.00 (1H, m), 6.95 (2H, d, J=6.5 Hz), 7.19 (1H, t, J=8.2 Hz), 7.28 (2H, t, J=7 Hz), 7.46 (1H, d, J=8.2 Hz), 7.94 (1H, s), 8.44 (2H, d, J=6.5 Hz).

Example 55

Synthesis of (E)-3-[4-(1-imidazolylmethyl)phenyl]-2-propene-1-yl 1,4-dihydro-2,6-dimethyl-5-(2-furyl)-4-(3-nitrophenyl)-pyridine-3-carboxylate

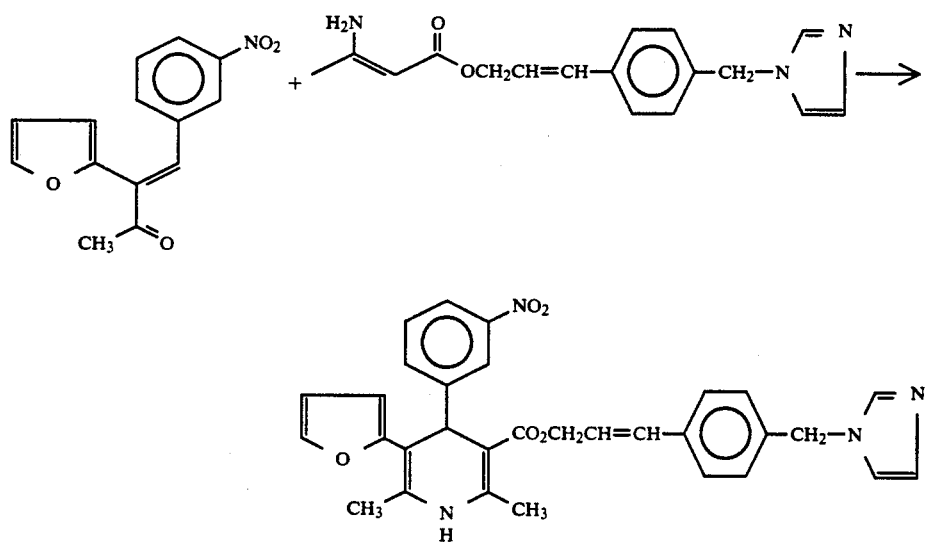

A mixuture of 257 mg (1 mmol) of 3-(2-furyl}-4-(3-nitrophenyl)-3-butene-2-one, 885 mg (3 mmol) of (E)-3-

(4-(1-imidazolylmethyl)phenyl]-2-propene-1-yl 3-aminocrotonate, 409 mg [2 mmol] of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 210 mg (39%).

Melting point: 81° C. (decomposed).

IR (cm$^{-1}$, KBr); $\nu$ CO 1690, $\nu$ NO$_2$ 1528, 1350.

Mass Analysis for C$_{31}$H$_{28}$N$_4$O$_5$: Calculated: 536,20593, Found: 536.20635.

NMR ($\delta$, CDCl$_3$); 2.27 (3H, s), 2.39 (3H, s), 4.68 (1H, dd, J=12.5 Hz, 6 Hz), 4.80 (1H, dd, J=12.5 Hz, 6 Hz), 5.05 (1H, s), 5.22 (1H, s), 5.66 (1H, s), 6.05 (1H, d, J=3.2 Hz), 6.25~6.35 (2H, m), 6.54 (1H, d, J=16 Hz), 7.00 (1H, s), 7.19 (2H, d, J=9 Hz), 7.24 (1H, s), 7.30 (1H, d, J=2 Hz), 7.35 (1H, t, J=6.4 Hz), 7.38 (2H, d, J=9 Hz), 7.68 (1H, d, J=6.4 Hz), 7.97 (1H, d, J=6.4 Hz), 8.16 (1H, s), 8.18 (1H, s).

Example 56

Synthesis of 3-cyano-1,4-dihydro-2,6-dimethyl-4-(3-nitrophenyl-5-(2-pyridyl)pyridine

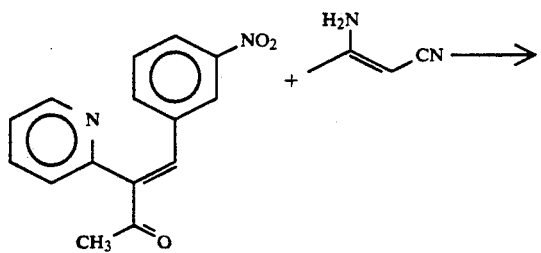

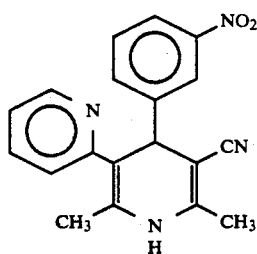

A mixuture of 268 mg [1 mmol) of 4-(3-nitrophenyl)-3-(2-pyridyl)-3-butene-2-one, 410 mg (5 mmol) of 3-aminocrotonitrile, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 160 mg (48%).

Melting point: 137.3° to 138.5° C.

IR (cm$^{-1}$, KBr); $\nu$ NH 3390, CN 2190, $\nu$ NO$_2$ 1530, 1355.

Mass Analysis for C$_{19}$H$_{16}$N$_4$O$_2$: Calculated: 332.12730, Found: 332.12778.

NMR ($\delta$, CDCl$_3$); 2.03 (3H, s), 2.17 (3H, s), 5.03(1H, s), 5.56 (1H, s), 6.94 (1H, d, J=8Hz), 7.05 (1H, dd, J=8 Hz, 5 Hz), 7.39 (1H, t, J=8 Hz), 7.50 (1H, td, J=8 Hz, 2 Hz), 7.52 (1H, d, J=8 Hz), 8.02 (1H, dt, J=8 Hz, 2 Hz), 8.09 (1H, t, J=2 Hz), 8.52 (1H, d, J=5 Hz),

Example 57

Synthesis of N,N-diethyl-1,4-dihydro-2,6-dimethyl-4-(3-nitrophenyl)-5-(2-pyridyl)pyridine-3-carboxamide

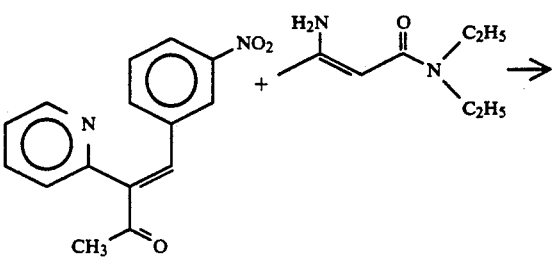

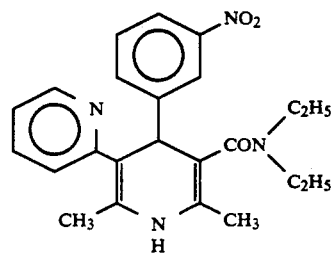

A mixuture of 268 mg (1 mmol) of 4-(3-nitrophenyl)-3-(2-pyridyl)-3-butene-2-one, 180 mg (5 mmol) of N,N-diethyl 3-amino-2-buteneamide, 273 mg [2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 259 mg (64%).

Melting point: oil,

IR (cm$^{-1}$, KBr); $\nu$ CO 1685, $\nu$ NO$_2$ 1530, 1350.

Mass Analysis for C$_{31}$H$_{33}$N$_5$O$_4$: Calculated: 539.25321, Found: 539.25378.

NMR ($\delta$, CDCl$_3$); 0.68~1.13 (6H, m), 1.85 (3H, s), 2.09 (3H, s), 3.14~3.49 (4H, m), 4.97 (1H, s), 5.10 (1H, bs), 6.96 (1H, dd, J=8 Hz, 5 Hz), 7.02 (1H, d, J=8 Hz), 7.33 (1H, t, J=8 Hz), 7.45 (1H, td, J=8 Hz, 2 Hz), 7.57 (1H, d, J=8 Hz), 7.94 (1H, ddd, J=8 Hz, 2Hz, 1 Hz), 8.07 (1H, t, J=2 Hz), 8.46 (1H, d, J=5 Hz).

Example 58

Synthesis of 3-benzoyl-1,4-dihydro-2,6-dimethyl-4(3-nitrophenyl)-5-(2-pyridyl)pyridine

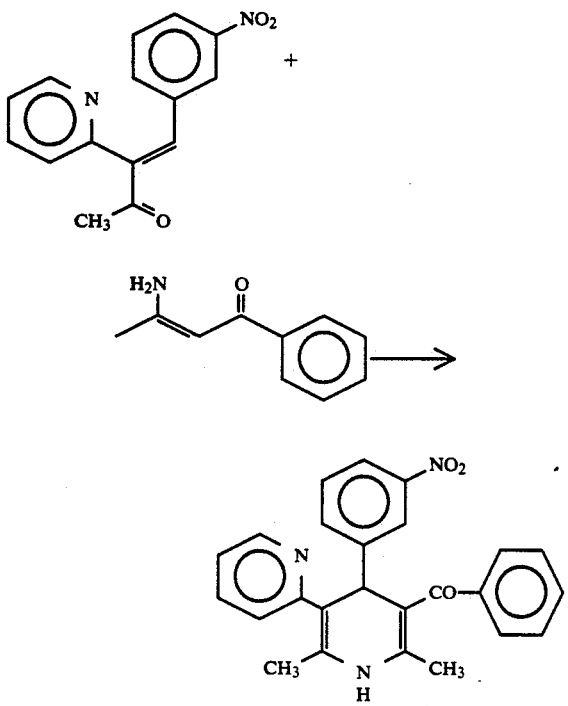

A mixuture of 268 mg (1 mmol) of 4-(3-nitrophenyl)-3-(2-pyridyl)-3-butene-2-one, 805 mg [5 mmol] of 3-amino-1-phenyl-2-butene-1-one, 273 mg (2 mmol) of zinc chloride, and 500 mg of Molecular Shieves 4A was added to 1,4-dioxane. This reaction mixture was refluxed with application of heat in an inert atmoshpere for 5 hours The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 288 mg (70%).

Melting point: 202.3° to 206.8° C.

IR (cm$^{-1}$, KBr); $\nu$ NH$_{3310}$, CO 1680, $\nu$ NO$_2$ 1525, 1345.

Mass Analysis for $C_{25}H_{21}N_3O_3$: Calculated:411.15827, Found: 411.15832.

NMR ($\delta$, CDCl$_3$); 1.86 (3H, s), 2.21 (3H, s), 5.32 (1H,s), 5.64 (1H, bs), 7.02 (1H, d, J=8 Hz), 7.05 (1H, ddd, J=8 Hz, 5 Hz, 1 Hz), 7.27~7.58 (8H, m), 7.96 (1H, ddd, J=8 Hz, 2 Hz, 1 Hz), 8.05 (1H, t, J=2 Hz), 8.54 (1H, d, J=5 Hz).

Example 59

Synthesis of 3-acetyl-1,4-dihydro-2,6-dimethyl-4(3-nitrophenyl)-5-(2-pyridyl)pyridine

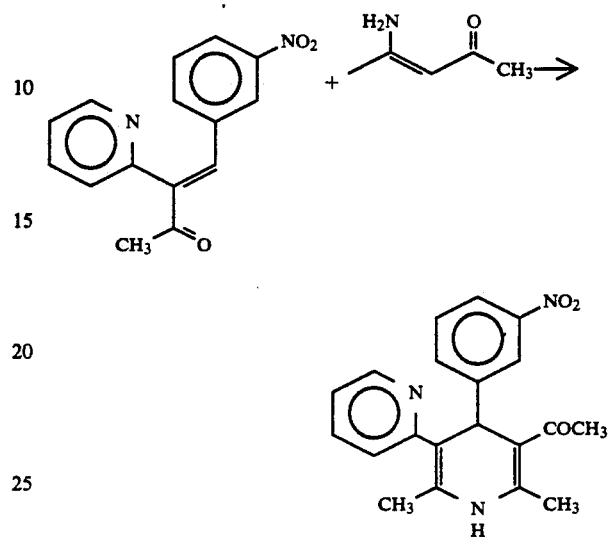

A mixuture of 268 mg (1 mmol) of 4-(3-nitrophenyl)-3-(2-pyridyl)-3-butene-2-one, 495 mg (5 mmol) of 4-amino-3-pentene-2-one, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 49 mg (14%).

Melting point: 192.5° to 193.1° C.

IR (cm$^{-1}$, KBr), : $\nu$ NH 3320, $\nu$ NO$_2$ 1530, 1340.

Mass Analysis for $C_{20}H_{19}H_3O_3$: Calculated: 349.14260, Found: 349.14319.

NMR ($\delta$, CDCl$_3$); 2.04 (3H, s), 2.18 (3H, s), 2.42 (3H, s), 5.34 (1H, s), 5.60 (1H, bs), 6.96 (1H, dd, J=8 Hz, 1 Hz), 7.09 (1H, dd, J=8 Hz, 5 Hz), 7.31 (1H, t, J=8 Hz), 7.48 (1H, d, J=8 Hz), 7.53 (1H, td, J=8 Hz, 2 Hz), 7.96 (1H, d, J=8 Hz), 7.99 (1H, t, J=2 Hz), 8.59 (1H, d, J=5 Hz).

Example 60

Synthesis of 2,2,2-trifluoroethyl 1,4-dihydro-2,6-dimethyl-4-(3-nitrophenyl)-5-(2-pyridyl)pyridine-3-carboxylate

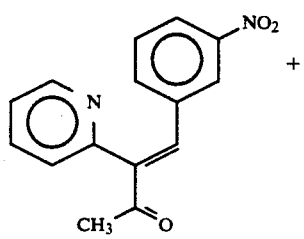

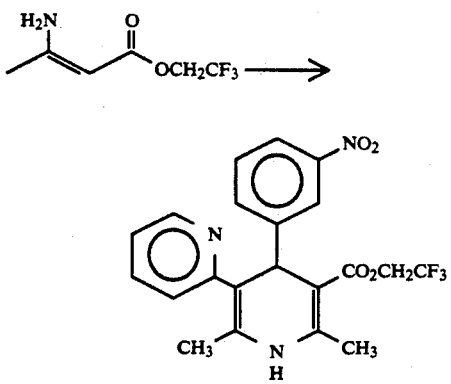

A mixuture of 268 mg [1 mmol] of 4-(3-nitrophenyl)-3-(2-pyridyl)-3-butene-2-one, 915 mg (5 mmol) of 2,2,2-trifluoroethyl 3-aminocrotonate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 101 mg (23%).

Melting point: 132.1° to 134.4° C.

IR (cm$^{-1}$, KBr); $\nu$ NH3390, $\nu$ CO 1960, NO$_2$ 1525, 1350.

Mass Analysis for C$_{21}$H$_{18}$N$_3$O$_4$: Calculated: 433.12491, Found: 433.12453.

NMR ($\delta$, CDCl$_3$); 2.05 (3H, s), 2.41 (3H, s), 4.24~4.53(2H, m), 5.21 (1H, s), 5.67 (1H, bs), 6.93 (1H, d, J=8 Hz), 7.07 (1H, ddd, J=8 Hz, 5 Hz, 1 Hz), 7.31 (1H, t, J=8 Hz), 7.49 (1H, d, J=8 Hz), 7.51 (1H, td, J=8 Hz, 2 Hz), 7.97 (1H, dt, J=8 Hz, 2 Hz), 8.07 (1H, t, J=2 Hz), 8.56 (1H, d, J=5 Hz).

Example 61

Synthesis of 1,4-dihydro-2,6-dimethyl-3-nitro-4-(3-nitrophenyl)-5-(2-pyridyl)pyridine

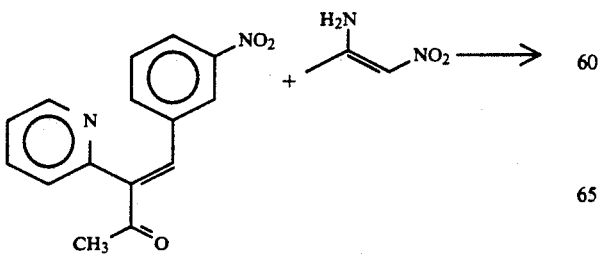

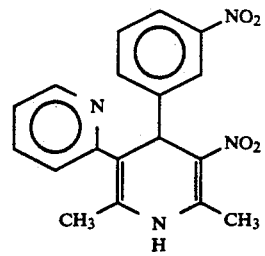

A mixuture of 268 mg (1 mmol) of 4-(3-nitrophenyl)-3-(2-pyridyl)-3-butene-2-one, 510 mg (5 mmol) of 2-amino-1-nitro-1-propene, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 98 mg (28%).

Melting Point: 195.6° to 199.2° C.

IR (cm$^{-1}$, KBr); $\nu$ NO$_2$ 1530, 1350.

Mass Analysis for C$_{18}$H$_{16}$N$_4$O$_4$: Calculated: 352.11712, Found: 352.11891.

NMR ($\delta$, CDCl$_3$); 2.06 (3H, s), 2.64 (3H, s), 5.70 (1H, s), 5.98 (1H, bs), 6.95 (1H, d, J=8 Hz), 7.11 (1H, ddd, J=8 Hz, 5 Hz, 1 Hz), 7.33 (1H, t, J=8 Hz), 7.54 (1H, td, J=8 Hz, 2 Hz), 7.55 (1H, d, H=8 Hz), 7.98 (1H, ddd, J=8 Hz, 2 Hz, 1 Hz), 8.08 (1H, t, J=2 Hz), 8.58 (1H, d, J=8 Hz).

Example 62

Synthesis of methyl 1,4-dihydro-2,6-dimethyl-4-(3-nitrophenyl)-5-pyridyl-pyridine-3-sulfinate

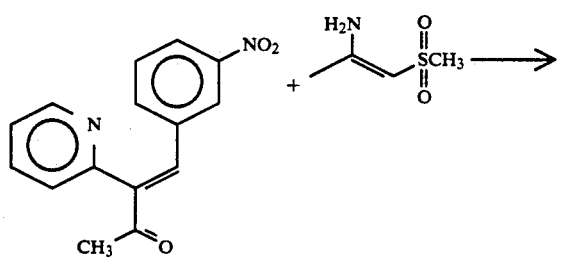

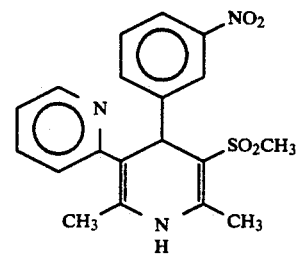

A mixuture of 268 mg (1 mmol) of 4-(3-nitrophenyl)-3-(2-pyridyl)-3-butene-2-one, 675 mg (5 mmol) of methyl 3-amino-2-propenesulfinate, 273 mg (2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 150 mg (39%).

Melting point: 210.8° to 211.5° C.

IR (cm$^{-1}$, KBr); $\nu$ NH 3350, $\nu$ NO$_2$ 1530, 1350.

Mass Analysis for C$_{19}$H$_{19}$N$_3$O$_4$S: Calculated: 395.10960, Found: 385.10962.

NMR ($\delta$, CDCl$_3$); 2.07 (3H, s), 2.39 (3H, s), 2.68 (3H, s), 5.30 (1H, s), 6.05 (1H, bs), 7.00 (1H, d, J=8 Hz), 7.07 (1H, dd, J=8 Hz, 5 Hz), 7.35 (1H, t, J=8 Hz), 7.53 (1H, td, J=8 Hz, 2 Hz), 7.62 (1H, d, J=8 Hz), 8.01 (1H, d, J=8 Hz), 8.15 (1H, t, J=2 Hz), 8.53 (1H, d, J=5 Hz).

Example 63

Synthesis of methyl 1,4-dihydro-2,6-dimethyl-4-(3-methoxyphenyl)-5-(2-pyridyl)pyridine-3-carboxylate

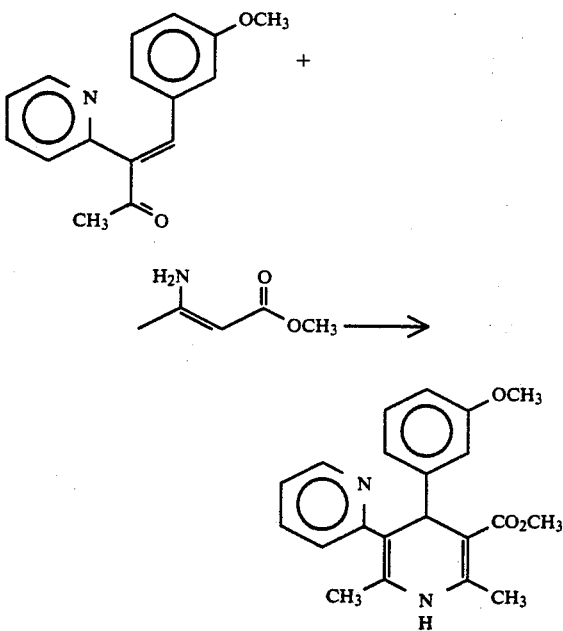

A mixuture of 268 mg (1 mmol) of 4-(3-methoxyphenyl)-3-(2-pyridyl)-3-butene-2-one, 575 mg (5 mmol) of methyl 3-aminocrotonate, 273 mg [2 mmol) of zinc chloride, and 500 mg of Molecular Shieves 4A was added to 1,4-dioxane. This reaction mixture was refluxed with application of heat in an inert atmoshpere for 5 hours. The reaction mixture was then cooled to room temperature and neutralized with a saturated aqueous solution of sodium hydrogencarbonate, followed by extraction with chloroform. The solvents contained in the extract were distilled off and the residue was chromatographed on a silica gel column, whereby the captioned compound was obtained. The yield was 210 mg (60%).

Melting point: 164.2° to 164.6° C.

IR (cm$^{-1}$, KBr); $\nu$ CO 1690.

Mass Analysis for C$_{21}$H$_{22}$N$_2$O$_3$: Calculated: 350.16302, Found: 350.16082.

NMR($\delta$, CDCl$_3$); 2.07 (3H, s), 2.35 (3H, s), 3.63 (3H, s), 3.71 (3H, s), 5.02 (1H, s), 5.45 (1H, bs), 6.66 (1H, dd, J=8 Hz, 2 Hz), 6.79 (1H, t, J=2 Hz), 6.83 (1H, d, J=8 Hz), 6.97 (1H, d, J=8 Hz), 7.03 (1H, ddd, J=8 Hz 5 Hz, 1 Hz), 7.11 (1H, t, J=8 Hz), 7.48 (1H, td, J=8 Hz), 8.54 (1H, d, J=5 Hz).

1. Test for blood platelet aggregation inhibitory activity of rabbit

The compound to be tested was dissolved in a 50%HCO-60/ethanol solvent and the solution was diluted with physiological sodium chloride solution in such a fashion that the maximum concentration of the solvents contained therein did not exceed 5%, whereby a test solution for the compound was prepared.

A blood of a rabbit (Japanese white; male; 2.3-3.6 kg) was exsanguinated from a carotid of the rabbit, and nine parts of the blood were mixed with one part of a 3.8% aqueous solution of sodium citrate. The mixture was centrifuged under 200 $\times$g at 20° C. for 15 minutes. The upper layer is a platelet rich plasma PRP), and the lower layer was further centrifuged under 1500 $\times$g at 20° C. for 10 minutes, so that a platelet poor plasma (PPP) was obtained.

10 $\mu$l of the test solution was added to the 200 $\mu$l of PRP, and the mixture was subjected to incubation at 37° C. for 10 minutes. To this mixture was added 10 $\mu$l of a sodium arachidonate solution,(22 mM) for causing the aggregation. The extent of the aggregation was investigated by measuring the transparency of the test sample by Agricometer (NKK, PAT-4A). The blood platelet aggregation inhibitory activity of the test sample was obtained as a relative value with the transparency of PPP being 100%.

The results are shown in table below.

2. Test for hypotensive activity

Male spontaneously hypertensive rats (SHR) with arterial blood pressures higher than 140 mmHg were used for the experiments. Arterial blood pressure was measured through the catheterized artery with a pressure transducer (MPU-05 manufactured by Nihon Kohden Kabushiki Kaisha). The catheter was inserted into the abdominal aorta via the median coccygeal artery of SHR under light ether anesthesia. Heart rate (HR) was simultaneously recorded by a heart rate counter (AT-601G manufactured by Nihon Kohden) triggered by the blood pressure pulse. The recordings were made on a rectigraph (manufactured by Sanei Sokki Kabushik Kaisha). The compounds to be tested were administered at least two hours after the operation with the catheter, which had been previously inserted into the coccygeal vein. SHR were restrained with a wire mesh cage immediately after the operation.

The results are shown in table below.

TABLE
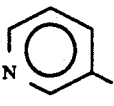
| Examples | Ar¹ | Ar² | R¹ | AA Control $10^{-4}$ M (%) | SHR - ΔMAX 300 μg/kg |
|---|---|---|---|---|---|
| 1 | 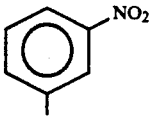 | 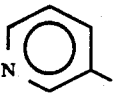 | CO₂Me | 46.2 | 40 |
| 2 | 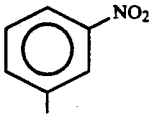 | 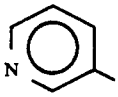 | CO₂Et | 42.1 | 45 |
| 3 | 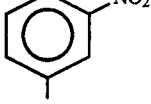 | 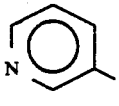 | CO₂i-Pr | 34.2 | 60 |
| 4 | 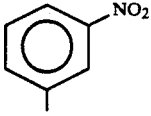 | 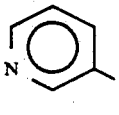 | CO₂n-Hex | 30.9 | 35 |
| 5 | 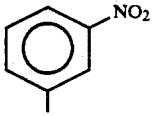 | 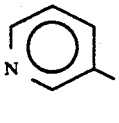 | CO₂c-Hex | 20.0 | 40 |
| 6 | 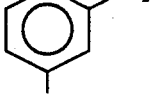 | 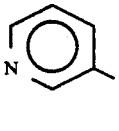 |  | 29.5 | 35 |
| 7 | 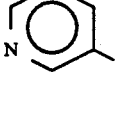 |  | 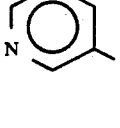 | 28.4 | 50 |
| 8 |  | 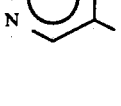 |  | 40.7 | 40 |
| 9 |  |  | CO₂CH₂CF₃ | 51.3 | 50 |
| 10 |  |  |  | 42.3 | 45 |

TABLE-continued

[Structure: 1,4-dihydropyridine with Ar¹ at 5-position, Ar² at 4-position, R¹ at 3-position, CH₃ at 2- and 6-positions, NH at 1-position]

| Examples | Ar¹ | Ar² | R¹ | AA Control $10^{-4}$ M (%) | SHR - ΔMAX 300 μg/kg |
|---|---|---|---|---|---|
| 11 | 3-pyridyl | 3-nitrophenyl | $CO_2CH_2C{\equiv}CH$ | 43.0 | 30 |
| 12 | 3-pyridyl | 3-nitrophenyl | $CO_2CH_2CH{=}CHCH{=}CHCH_3$ | 36.0 | 25 |
| 13 | 3-pyridyl | 3-nitrophenyl | $CO_2CH_2CH{=}CHC_6H_5$ (trans) | 30.1 | 35 |
| 14 | 3-pyridyl | 3-nitrophenyl | $CO_2CH_2CH{=}CHC_6H_5$ (cis) | 24.2 | 25 |
| 15 | 3-pyridyl | 3-nitrophenyl | $CO_2CH_2C{\equiv}CC_6H_5$ | 32.2 | 15 |
| 16 | 3-pyridyl | 3-nitrophenyl | $CO_2CH_2CH{=}CHC{\equiv}CC_6H_5$ | 42.1 | 25 |
| 17 | 3-pyridyl | 3-nitrophenyl | $CO_2CH_2CH{=}CHCH{=}CHC_6H_5$ | 33.8 | 55 |
| 18 | 3-pyridyl | 3-nitrophenyl | $CO_2CH_2CH{=}CH$-(4-imidazolylmethyl-phenyl) (trans) | 30.3 | 10 |
| 19 | 3-pyridyl | 3-nitrophenyl | $CO_2CH_2CH{=}CH$-(4-imidazolylmethyl-phenyl) (cis) | 49.5 | 25 |

TABLE-continued

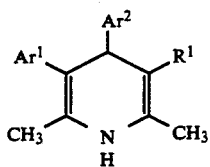

| Examples | Ar¹ | Ar² | R¹ | AA Control $10^{-4}$ M (%) | SHR - ΔMAX 300 μg/kg |
|---|---|---|---|---|---|
| 21 | 3-pyridyl | 3-NO₂-phenyl | -CO₂-CH₂CH₂-N(piperazinyl)-N-CH(phenyl)₂ | 39.0 | 40 |
| 22 | 3-pyridyl | 3-NO₂-phenyl | -CO₂-CH₂CH₂-N(piperazinyl)-N-phenyl | 42.5 | 80 |
| 23 | 3-pyridyl | 3-NO₂-phenyl | -CO₂-CH₂CH₂-N(4-phenylpiperidinyl) | 28.5 | 83 |
| 24 | 3-pyridyl | 3-NO₂-phenyl | -CO₂-CH₂CH₂-N(Me)(CH₂-phenyl) | 27.0 | 35 |
| 25 | 3-pyridyl | 3-NO₂-phenyl | -CO₂-CH₂CH₂-N(1,2,3,4-tetrahydroisoquinolin-2-yl) | 29.4 | 65 |
| 30 | 3-pyridyl | 2-CN-6-Me-phenyl | CO₂Me | 21.5 | 35 |
| 47 | pyrazin-2-yl | 3-NO₂-phenyl | CO₂Me | 37.3 | 55 |
| 50 | 4-pyridyl | 3-NO₂-phenyl | -CO₂-CH₂CH₂-N(Me)(CH₂-phenyl) | 12.5 | 40 |
| 51 | 4-pyridyl | 3-NO₂-phenyl | -CO₂-CH₂-CH=CH-phenyl | 12.6 | 40 |

TABLE-continued

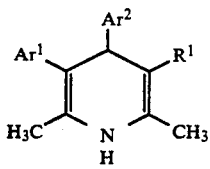

| Examples | Ar¹ | Ar² | R¹ | AA Control $10^{-4}$ M (%) | SHR - ΔMAX 300 μg/kg |
|---|---|---|---|---|---|
| 52 | pyridyl | 3-NO₂-phenyl | -CO₂-CH₂CH₂-N(piperazine)N-phenyl | 15.0 | 70 |
| 53 | pyridyl | 3-NO₂-phenyl | -CO₂-CH₂-CH=CH₂ | 17.0 | 35 |
| 54 | pyridyl | 3-NO₂-phenyl | -CO₂-CH₂CH₂-O-phenyl | 16.8 | 35 |
| 55 | furyl | 3-NO₂-phenyl | -CO₂-CH₂CH₂-CH=CH-phenyl-CH₂-N(imidazolyl) | 38.3 | 20 |

What is claimed is:

1. 1,4-Dihydropyridine derivatives of formula (I):

$$\text{(I)}$$

wherein Ar¹ represents a naphthyl group which may have a substituent, or an aromatic heterocyclic group selected from the group consisting of pyridyl group, quinolyl group, isoquinolyl group, furyl group, thienyl group, benzoxazolyl group, benzothiazolyl group, pyridazinyl group, pyrazinyl group, pyrimidinyl group, indolyl group, benzoxadiazolyl group and benzothiadiazolyl group, which aromatic heterocyclic group may have a substituent, and Ar² represents an aromatic hydrocarbon group which may have a substituent, or an aromatic heterocyclic group which may have a substituent; R¹ represents a group selected from the group consisting of —CO₂R², —SO₂R³, —COR⁴, —CON(R⁵)₂, —CN or —NO₂; R² represents (i) hydrogen, (ii) a straight chain, branched chain or cyclic saturated hydrocarbon group having 1 to 10 carbon atoms, which may have a substituent selected from the group consisting of an alkyl group having 1 to 4 carbon atoms, an alkoxy group having 1 to 4 carbon atoms, a phenoxy group which may have a substituent, a phenylthio group which may have a substituent, a substituted amino group, a cyclic amino group which may have a substituent, a phenyl group which may have a substituent, an aromatic heterocyclic group which may have a substituent, and a trihalomethyl group, or (iii) a straight chain, branched chain or cyclic unsaturated hydrocarbon group having 2 to 10 carbon atoms, which may have a substituent selected from the group consisting of an alkyl group having 1 to 4 carbon atoms, an alkoxyl group having 1 to 4 carbon atoms, a phenoxy group which may have a substituent, a phenylthio group which may have a substituent, a substituted amino group, a cyclic amino group which may have a substituent, a phenyl group which may have a substituent, an aromatic heterocyclic group which may have a substituent, and a trihalomethyl group; R³ represents an alkyl group having 1 to 4 carbon atoms; R⁴ represents an alkyl group having 1 to 4 carbon atoms, or a phenyl group; and R⁵ represents an alkyl group having 1 to 4 carbon atoms.

2. The 1,4-dihydropyridine derivatives as claimed in claim 1, wherein the substituent of the aromatic heterocyclic group represented by Ar¹ is selected from the group consisting of a halogen, cyano group, nitro group, trifluoromethyl group, trichloromethyl group, azide group, amide group, an alkyl group having 1 to 4 carbon atoms, an alkoxyl group having 1 to 4 carbon atoms, benzoyl group, an alkylthio group having 1 to 4 carbon atoms, phenylthio group, phenoxy group, a lower alkoxycarbonyl group, a lower acyl group, benzyloxy group, hydroxy group, and cinnamyloxy group.

3. The 1,4-dihydropyridine derivatives as claimed in claim 1, wherein Ar² represents an aromatic hydrocarbon group selected from the group consisting of phenyl group and naphthyl group, each of which may have a substituent.

4. The 1,4-dihydropyridine derivatives as claimed in claim 1, wherein $Ar^2$ represents an aromatic heterocyclic group selected from the group consisting of pyridyl group, quinolyl group, isoquinolyl group, furyl group, thienyl group, benzoxazolyl group, benzothiazolyl group, pyridazinyl group, pyrazinyl group, pyrimidinyl group, indolyl group, benzoxadiazolyl group, and benzothiadiazolyl group, each of which may have a substituent.

5. The 1,4-dihydropyridine derivatives as claimed in claim 3, wherein the substituent of the aromatic hydrocarbon group represented by either $Ar^2$ is selected from the group consisting of a halogen, cyano group, nitro group, trifluoromethyl group, trichloromethyl group, azide group, amide group, an alkyl group having 1 to 4 carbon atoms, an alkoxyl group having 1 to 4 carbon atoms, a benzoyl group, an alkylthio group having 1 to 4 carbon atoms, phenylthio group, phenoxy group, a lower alkoxycarbonyl group, a lower acyl group, benzyloxy group, hydroxy group, and cinnamyloxy group.

6. The 1,4-dihydropyridine derivatives as claimed in claim 4, wherein the substituent of the aromatic heterocyclic group represented by $Ar^2$ is selected from the group consisting of a halogen, cyano group, nitro group, trifluoromethyl group, trichloromethyl group, azide group, amide group, an alkyl group having 1 to 4 carbon atoms, an alkoxyl group having 1 to 4 carbon atoms, benzoyl group, an alkylthio group having 1 to 4 carbon atoms, phenylthio group, phenoxy group, a lower alkoxycarbonyl group, a lower acyl group, benzyloxy group, hydroxy group, and cinnamyloxy group.

7. The 1,4-dihydropyridine derivatives as claimed in claim 1, wherein $Ar^2$ is selected from the group consisting of phenyl group, 2-nitrophenyl group, 3-nitrophenyl group, 4-nitrophenyl group, 2-cyanophenyl group, 2-bromophenyl group, 3-bromophenyl group, 4-bromophenyl group, 2-chlorophenyl group, 3-chlorophenyl group, 4-chlorophenyl group, 2-iodophenyl group, 3-iodophenyl group, 4-iodophenyl group, 3-cyanophenyl group, 4-cyanophenyl group, 2,3-dichlorophenyl group, 2,6-dichlorophenyl group, 3,5-dichlorophenyl group, 2-furyl group, furyl group, thienyl group, 3-thienyl group, 1-naphthyl group, naphthyl group, 3-azidophenyl group, 2-trifluoromethylphenyl group, 4-trifluoromethylphenyl group, 3-trifluoromethylphenyl group, 2-methylphenyl group, 3-methylphenyl group, 4-methylphenyl group, 2-hydroxyphenyl group, 3-hydroxyphenyl group, 4-hydroxyphenyl group, 2-benzyloxyphenyl group, 3-benzyloxyphenyl group, 2-cinnamyloxyphenyl group, 3-cinnamyloxyphenyl group, 3-benzoylphenyl group, 2-methoxyphenyl group, 3-methoxyphenyl group, 4-methoxyphenyl group, 4-methylthiophenyl group, 3-trichloromethylphenyl group, 2-pyridyl group, pyridyl group, 4-pyridyl group, quinolyl group, 3-quinolyl group, 4-quinolyl group, 1-isoquinolyl group, quinoxalyl group, 2-chloropyridyl group, 6-chloropyridyl group, 2-methylpyridyl group, 6-methylpyridyl group, 2-methoxypyridyl group, 6-methoxypyridyl group, 5-bromopyridyl group, 2-amionpyridyl group, 2-mercaptopyridyl group, pyridazinyl group, 4-pyridazinyl group, pyrazinyl group, pyrimidinyl group, 5-pyrimidinyl group, 7-benzoxazolyl group, 7-benzothiazolyl group, 3-benzoxadiazolyl group, 3-benzothiazolyl group, 2-indolyl group, 3-indolyl group, and 5-indolyl group.

8. The 1,4-dihydropyridine derivatives as claimed in claim 1, wherein $R^1$ is $—CO_2R^2$, in which $R^2$ is hydrogen.

9. The 1,4-dihydropyridine derivatives as claimed in claim 1, wherein $R^1$ is $—CO\ R^2$, in which $R^2$ is a straight chain or branched saturated hydrocarbon group selected from the group consisting of methyl group, ethyl group, n-propyl group, n-butyl group, n-pentyl group, n-hexyl group, n-heptyl group, n-octyl group, n-nonyl group, n-decyl group, isoproyl group, and isobutyl group, each of which may have a substituent.

10. The 1,4-dihydropyridine derivatives as claimed in claim 1, wherein $R^1$ is $—CO_2R^2$, in which $R^2$ is a cyclic hydrocarbon group selected from the group consisting of cyclopentyl group and cyclohexyl group, each of which may have a substituent.

11. The 1,4-dihydropyridine derivatives as claimed in claim 1, wherein $R^1$ is $—CO_2R^2$, in which $R^2$ is an unsaturated hydrocarbon group selected from the group consisting of propenyl group, 2-butenyl group, 3-butenyl group, 2-pentenyl group, 2,4-hexadienyl group, 2,4-hexadiynyl group, hexa-4-en-2-yne, each of which may have a substituent.

12. The 1,4-dihydropyridine derivatives as claimed in claim 9, wherein the substituent of $R^2$ is selected from the group consisting of an alkoxyl group having 1 to 6 carbon atoms, an unsubstituted or substituted phenoxy group, an unsubstituted or substituted phenylthio group, a substituted amino group, cyclic amino group, an unsubstituted or substituted phenyl group, an unsubstituted or substituted pyridyl group, an aromatic heterocyclic group, and a trihalomethyl group.

13. The 1,4-dihydropyridine derivatives as claimed in claim 10, wherein the substituent of $R^2$ is selected from the group consisting of an alkyl group having 1 to 6 carbon atoms, an alkoxy group having 1 to 6 carbon atoms, an unsubstituted or substituted phenoxy group, an unsubstituted or substituted phenylthio group, a substituted amino group, a cyclic amino group, an unsubstituted or substituted phenyl group, an unsubstituted or substituted pyridyl group, an aromatic heterocyclic group, and a trihalomethyl group.

14. The 1,4-dihydropyridine derivatives as claimed in claim 11, wherein the substituent of $R^2$ is selected from the group consisting of an alkyl group having 1 to 6 carbon atoms, an alkyl group having 1 to 6 carbon atoms, an unsubstituted or substituted phenoxy group, an unsubstituted or substituted phenylthio group, a substituted amino group, cyclic amino group, an unsubstituted or substituted phenyl group, an unsubstituted or substituted pyridyl group, an aromatic heterocyclic group, and a trihalomethyl group.

15. The 1,4-dihydropyridine derivatives as claimed in claim 12, wherein said alkoxyl group is selected from the group consisting of methoxy group, ethoxy group and propoxy group.

16. The 1,4-dihydropyridine derivatives as claimed in claim 12, wherein said substituted amino group is selected from the group consisting of dimethyl amino group, diethyl amino group, and N-benzyl-N-methylamino group.

17. The 1,4-dihydropyridine derivatives as claimed in claim 12, wherein said cyclic amino group is selected from the group consisting of an unsubstituted or substituted piperazinyl group and piperidinyl group.

18. The 1,4-dihydropyridine derivatives as claimed in claim 12, wherein said aromatic heterocyclic group is selected from the group consisting of pyridyl group, quinolyl group, isoquinolyl group, furyl group, thienyl group, benzoxazolyl group, benzothiazolyl group, pyridazinyl group, pyrazinyl group, pyrimidinyl group, 19. The 1,4-dihydropyridine derivatives as claimed in claim 13, wherein said alkyl group is selected from the group consisting of methyl group, ethyl group, propyl group, and isopropyl group.

20. The 1,4-dihydropyridine derivatives as claimed in claim 13, wherein said alkoxyl group is selected from the group consisting of methoxy group, ethoxy group and propoxy group.

21. The 1,4-dihydropyridine derivatives as claimed in claim 13, wherein said substituted amino group is selected from the group consisting of dimethyl amino group, diethyl amino group, and N-benzyl-N-methylamino group.

22. The 1,4-dihydropyridine derivatives as claimed in claim 13, wherein said cyclic amino group is selected from the group consisting of an unsubstituted or substituted piperazinyl group and piperidinyl group.

23. The 1,4-dihydropyridine derivatives as claimed in claim 13, wherein said aromatic heterocyclic group is selected from the group consisting of pyridyl group, quinolyl group, isoquinolyl group, furyl group, thienyl group, benzoxazolyl group, benzothiazolyl group, pyridazinyl group, pyrazinyl group, pyrimidinyl group, indolyl group, benzoxadiazolyl group, and benzothiadiazolyl group.

24. The 1,4-dihydropyridine derivatives as claimed in claim 14, wherein said alkyl group is selected from the group consisting of methyl group, ethyl group, propyl group, and isopropyl group.

25. The 1,4-dihydropyridine derivatives as claimed in claim 14, wherein said alkoxyl group is selected from the group consisting of methoxy group, ethoxy group and propoxy group.

26. The 1,4-dihydropyridine derivatives as claimed in claim 14, wherein said substituted amino group is selected from the group consisting of dimethyl amino group, diethyl amino group, and N-benzyl-N-methylamino group.

27. The 1,4-dihydropyridine derivatives as claimed in claim 14, wherein said cyclic amino group is selected from the group consisting of an unsubstituted or substituted piperazinyl group and piperidinyl group.

28. The 1,4-dihydropyridine derivatives as claimed in claim 14, wherein said aromatic heterocyclic group is selected from the group consisting of pyridyl group, quinolyl group, isoquinolyl group, furyl group, thienyl group, benzoxazolyl group, benzothiazolyl group, pyridazinyl group, pyrazinyl group, pyrimidinyl group, indolyl group, benzoxadiazolyl group, and benzothiadiazolyl group.

29. The 1,4-dihydropyridine derivatives as claimed in claim 1, wherein $R^1$ is $-CO_2R^2$, in which $R^2$ is selected from the group consisting of hydrogen, methyl group, ethyl group, n-propyl group, n-butyl group, n-pentyl group, n-hexyl group, n-heptyl group, n-octyl group, n-nonyl group, n-decyl group, isopropyl group, isobutyl group, cyclopentyl group, cyclohexyl group, 2-propene-1-yl group, 2-propyne-1-yl group, [E]-2-butene-1-yl group, (E)-3-butene-1-yl group, (E)-2-pentene-1-yl group, (2E,4E)-2,4-hexadienyl group, 2,4-hexadiynyl group, (E)-hexa-4-en-2-yne group, (E)-3-phenyl-2-propene-1-yl group, (Z)-3-phenyl-2-propyne-1-yl group, 3-phenyl-2-propyne-1-yl group, [2E,4E)-5-phenyl-2,4-pentadiene-1-yl group, 5-phenyl-penta-2,4-diyne-1-yl group, (E)-5-phenyl-penta-2-en-4-yne-1-yl group, (E)-3-[4-(1-imidazolylmethyl)phenyl]-2-propene-1-yl group, (E)-3-[3-(1-imidazolylmethyl)phenyl]-2-propene-1-yl group, (E)-3-[2-[1-imidazolylmethyl)phenyl]-2-propene-1-yl group, (Z)-3-[4-(1-imidazolylmethyl)phenyl]-2-propene-1-yl group, (E)-3-[6-(1-imidazolylmethyl)pyridine-2-yl]-2-propene-1-yl group, (E)-3-[5-(1-imidazolylmethyl)furan-2-yl]-2-propene-1-yl group, (E)-3-[5-(1-imidazolylmethyl)thiophene-2-yl]-2-propene-1-yl group, (E)-3-phenyl-1-methyl-2-propene-1-yl group, (E)-2-fluoro-3-phenyl-2-propene-1-yl group, 2-methoxyethyl group, 3-methoxypropyl group, 3-ethoxypropyl group, 2-phenoxyethyl group, 2-phenylthioethyl group, 2-(N-methylamino)ethyl group, 2-(N,N-dimethylamino)-ethyl group, 2-(N-methyl-N-phenylamino)ethyl group, 2-N,N-diethylamino)ethyl group, 2-(N-benzyl-N-methylamino)-ethyl group, 2-(1-piperazinyl)ethyl group, 4-(1-piperazinyl)butyl group, 6-(1-piperazinyl)hexyl group, 2-(1-piperidinyl)ethyl group, 2-(4-phenylpiperazine-1-yl)-ethyl group, 3-(4-phenylpiperazine-1-yl)propyl group, 4-4-phenylpiperazine-1-yl)butyl group, 6-(4-phenylpiperadine-1-yl)hexyl group, 2-(4-phenylpiperidine-1-yl)-ethyl group, 3-(4-phenylpiperidine-1-yl)propyl group, 4-(4-phenylpiperidine-1-yl)butyl group, 4-(4-phenylpiperidine-1-yl)butyl group, 6-(4-phenylpiperidine-1-yl)hexyl group, 2-[4-(diphenylmethyl)piperazine-1-yl]ethyl group, 3-[4-(diphenylmethyl)piperazine-1-yl)propyl group, 4-[4-(diphenylmethyl)piperazine-1-yl)]butyl group, 6-[4-(diphenylmethyl)piperazine-1-yl)]hexyl group, 2-morpholinoethyl group, N-benzylpyrrolidine-3-yl group, N-benzylpiperidine-3-yl group, 2-[1,2,3,4-tetrahydroisoquinoline-2-yl)ethyl group, 2,2,2-trifluoroethyl group, 2-(3,7-dihydro-3,7-dimethyl-1H-purine-2,6-dione-1-yl)ethyl group, and 2-(1,2,3,6-tetrahydro-1,3-dimethyl-2,6-dioxo-7H-purine-7-yl)ethyl group.

30. The 1,4-dihydropyridine derivatives as claimed in claim 1, wherein $R^1$ is $-SO_2R^3$, in which $R^3$ is an alkyl group having 1 to 4 carbon atoms.

31. The 1,4-dihydropyridine derivatives as claimed in claim 30, wherein the alkyl group represented by $R^3$ is selected from the group consisting of methyl group, ethyl group, n-propyl group, and isopropyl group.

32. The 1,4-dihydropyridine derivatives as claimed in claim 1, wherein $R^1$ is $-COR^4$, in which $R^4$ is an alkyl group having 1 to 4 carbon atoms.

33. The 1,4-dihydropyridine derivatives as claimed in claim 32, wherein the alkyl group represented by $R^4$ is selected from the group consisting of methyl group, ethyl group, n-propyl group, and isopropyl group.

34. The 1,4-dihydropyridine derivatives as claimed in claim 1, wherein $R^1$ is $-COR^4$, in which $R^4$ is a phenyl group.

35. The 1,4-dihydropyridine derivatives as claimed in claim 1, wherein $R^1$ is $-CON(R^5)_2$, in which $R^5$ is an alkyl group having 1 to 4 carbon atoms.

36. The 1,4-dihydropyridine derivatives as claimed in claim 35, wherein the alkyl group represented by $R^5$ is selected from the group consisting of methyl group, ethyl group, n-propyl group, and isopropyl group.

* * * * *

UNITED STATES PATENT AND TRADEMARK OFFICE
CERTIFICATE OF CORRECTION

PATENT NO. : 5,276,150

DATED : January 4, 1994

INVENTOR(S) : Hiroshi IKAWA, et al.

It is certified that error appears in the above-identified patent and that said Letters Patent is hereby corrected as shown below:

Column 4, line 25, "(3-(1-imidazolylmethyl)" should read --[3-(1-imidazolylmethyl)--;

line 26, "(E)-3-(2-(1-imidazolylmethyl)" should read --(E)-3-[2-(1-imidazolylmethyl)--;

line 27, "(E)-3-(4-(1-imidazolylmethyl)" should read --(E)-3-[4-(1-imidazolylmethyl)--;

line 28, "(Z)-3-(4-(1-imidazolylmethyl)" should read --(Z)-3-[4-(1-imidazolylmethyl)--;

line 29, "(E)-3-(6-(1-imidazolylmethyl)" should read --(E)-3-[6-(1-imidazolylmethyl)--;

line 30, "(E)-3-(5-(1-imidazolylmethyl)" should read --(E)-3-[5-(1-imidazolylmethyl)--;

line 32, "(E)-3-(5-(1-imidazolylmethyl)" should read --(E)-3-[5-(1-imidazolylmethyl)--;

line 51, "2-(4-(diphenylmethyl)" should read --2-[4-(diphenylmethyl)--;

line 52, "(4-(diphenylmethyl)" should read --[4-(diphenylmethyl)--;

lines 52-53, "4-(4-(diphenylmethyl)" should read --4-[4-(diphenylmethyl)--;

lines 53-54, "6-(4-(diphenylmethyl)" should read --6-[4-(diphenylmethyl)--.

UNITED STATES PATENT AND TRADEMARK OFFICE
CERTIFICATE OF CORRECTION

PATENT NO. : 5,276,150

DATED : January 4, 1994

INVENTOR(S) : Hiroshi IKAWA, et al.

It is certified that error appears in the above-identified patent and that said Letters Patent is hereby corrected as shown below:

Column 6, line 6, "pyridylpridine" should read --pyridylpyridine--;

line 17, "methyl 4-4-bromophenyl)" should read --methyl 4-(4-bromophenyl)--;

line 60, "3-carboxylate, 1,4-dihydro-2" should read --3-carboxylate, methyl 1,4-dihydro-2,6-dimethyl-4-(2-methylphenyl)-5-pyridylpyridine-3-carboxylate,--;

line 61, "1,4-dihydro-2" should read --methyl 1,4-dihydro-2--;

line 67, "dimethyl-4-3-methoxylphenyl)" should read --dimethyl-4-(3-methylphenyl)--.

Column 7, line 45, "(E)-3-(4-(1-imidazolylmethyl)phenyl should read --(E)-3-[4-(1-imidazolylmethyl)phenyl]--;

line 48, "(E)-3-(4-(1-imidazolylmethyl)phenyl" should read --(E)-3-[4-(1-imidazolylmethyl)phenyl]--;

line 51, "(Z)-3-(4-(1-imidazolylmethyl)" should read --(Z)-3-[4-(1-imidazolylmethyl)--;

line 54, "(E)-3-(6-(1-imidazolylmethyl)" should read --(E)-3-[6-(1-imidazolylmethyl)--.

UNITED STATES PATENT AND TRADEMARK OFFICE
CERTIFICATE OF CORRECTION

PATENT NO. : 5,276,150

DATED : January 4, 1994

INVENTOR(S) : Hiroshi IKAWA, et al.

It is certified that error appears in the above-identified patent and that said Letters Patent is hereby corrected as shown below:

Column 7, line 57, "(E)-3-(5-(1-imidazolylmethyl)" should read --(E)-3-[5-(1-imidazolylmethyl)--;

line 60, "(E)-3-(5-(1-imidazolylmethyl)" should read --(E)-3-[5-(1-imidazolylmethyl)--.

Column 8, line 43, "formula I-1):" should read --formula (I-1):--.

Column 10, line 39, "(E)-3-(4-(1-imidazolylmethyl)" should read --(E)-3-[4-(1-imidazolylmethyl)--;

line 41, "(E)-3-(3-(1-lmidazolylmethyl)" should read --(E)-3-[3-(1-imidazolylmethyl)--;

line 43, "(E)-3-(2-(1-imidazolylmethyl)" should read --(E)-3-[2-(1-imidazolylmethyl)--;

line 45, "(Z)-3-(4-(1-imidazolylmethyl)" should read --(Z)-3-[4-(1-imidazolylmethyl)--;

line 47, "(E)-3-(6-(1-imidazolylmethyl)" should read --(E)-3-[6-(1-imidazolylmethyl)--;

line 49, "(E)-3-(5-(1-imidazolylmethyl)" should read --(E)-3-[5-(1-imidazolylmethyl)--;

line 51, "(E)-3-(5-(1-imidazolylmethyl)" should read --(E)-3-[5-(1-imidazolylmethyl)--.

UNITED STATES PATENT AND TRADEMARK OFFICE
CERTIFICATE OF CORRECTION

PATENT NO. : 5,276,150
DATED : January 4, 1994
INVENTOR(S) : Hiroshi IKAWA, et al.

It is certified that error appears in the above-identified patent and that said Letters Patent is hereby corrected as shown below:

Column 11, line 6, "ethy" should read --ethyl--;
    line 14, "4-(4-(diphenylmethyl)" should read --4-[4-(diphenylmethyl)--.

Column 13, line 16, "4-2-furyl)" should read --4-(2-furyl)--;
    line 54, "4-4-hydroxyphenyl)" should read --4-(4-hydroxyphenyl)--.

Column 14, line 3, "industriously," should read --industriously.--;
    line 16, "(E)-3-(4" should read --(E)-3-[4--;
    line 17, "E)-3-(3" should read --(E)-3-[3--;
    line 18, "(E)-3-(2" should read --(E)-3-[2--;
    line 19, "(Z)-3-(4" should read --(Z)-3-[4--;
    line 20, "(E)-3-(6" should read --(E)-3-[6--;
    line 22, "3-(5-(1-imidazolylmethyl)" should read --3-[5-(1-imidazolylmethyl)--;
    line 23, "(E)-3-(5-(1-imidazolylmethyl)" should read --(E)-3-[5-(1-imidazolylmethyl)--.

UNITED STATES PATENT AND TRADEMARK OFFICE
CERTIFICATE OF CORRECTION

PATENT NO. : 5,276,150
DATED : January 4, 1994
INVENTOR(S) : Hiroshi IKAWA, et al.

It is certified that error appears in the above-identified patent and that said Letters Patent is hereby corrected as shown below:

Column 14, line 55, "Starding" should read --Starting--.

Column 15, line 65, "N M R (67, $CDCl_3$)" should read --N M R ($\delta$, $CDCl_3$)--.

Column 16, line 30, "(3-nltrophenyl)" should read --(3-nitrophenyl)--.

Column 17, line 27, "KRr)" should read --KBr)--.

Column 19, line 44, "$C_{20}H_{19}H_3O_4$" should read --$C_{20}H_{19}N_3O_4$--.

Column 20, line 39, "($\delta$, $CDCl_3l_3$); 1.19 (3, t, J=6 Hz)" should read --($\delta$, $CDCl_3$); 1.19 (3H, t, J=6 Hz)--;
line 41, "(1H, dd, J=7,5 Hz)" should read --(1H, dd, J=7, 5Hz)--.

Column 22, line 11, "KRr)" should read --KBr)--;
line 50, "76 mg" should read --100 mg--.
line 51, "2-methoxyethanol " should read --cyclohexanol--.

UNITED STATES PATENT AND TRADEMARK OFFICE
CERTIFICATE OF CORRECTION

PATENT NO. : 5,276,150
DATED : January 4, 1994
INVENTOR(S) : Hiroshi IKAWA, et al.

It is certified that error appears in the above-identified patent and that said Letters Patent is hereby corrected as shown below:

Column 29, line 46, "b extraction" should read --by extraction--;

Column 29, line 64, "Found: 341.18439" should read --Found: 431.18439--.

Column 32, line 38, "[1 mmol)" should read --(1 mmol)--.

Column 33, line 62, "J=15 Hz 5.4 Hz)" should read --J=15 Hz, 5.4 Hz)--;

line 65, "(1H, dt, J=15 hz, 5.4 Hz)" should read --(1H, dt, J=15 Hz, 5.4 Hz)--.

Column 35, line 32, "of [E)" should read --of (E)--.

Column 39, line 40, "Found: 629,29894" should read --Found: 629.29894--.

Column 44, line 39, "5 66 (1H, s)" should read --5.66 (1H, s)--.

UNITED STATES PATENT AND TRADEMARK OFFICE
CERTIFICATE OF CORRECTION

PATENT NO. : 5,276,150

DATED : January 4, 1994

INVENTOR(S) : Hiroshi IKAWA, et al.

It is certified that error appears in the above-identified patent and that said Letters Patent is hereby corrected as shown below:

Column 46, line 52, "[1 mmol)" should read --(1 mmol)--.

Column 49, line 44, "(1H, dd, J=5, 4 Hz)" should read --(1H, dd, J=6, 4 Hz)--.

Column 51, lines 11-12, "(decomposed).
Mass Analysis for $C_{23}H_{21}N_3O_2$: Calculated:" should read
--(decomposed).
I R ($cm^{-1}$, KBr); υ CO 1695
Mass Analysis for $C_{23}H_{21}N_3O_2$: Calculated:--.

Column 52, line 47, "wa then" should read --was then--;
line 61, "Found: 359.14312" should read
--Found: 349.14312--.

Column 56, line 25, "was obtained The" should read --was obtained. The--.

Column 57, line 14, "($cm^{-1}$KBr); ν NB" should read --IR($cm^{-1}$KBr); ν NH--.

Column 58, line 55, "ν NB" should read --ν NH--.

Column 59, line 1, "Example 4" should read --Example 44--;
line 43, "ν NB" should read --ν NH--.

UNITED STATES PATENT AND TRADEMARK OFFICE
CERTIFICATE OF CORRECTION

PATENT NO. : 5,276,150

DATED : January 4, 1994

INVENTOR(S) : Hiroshi IKAWA, et al.

It is certified that error appears in the above-identified patent and that said Letters Patent is hereby corrected as shown below:

Column 60, line 35, "J=5, 1 Hz, 1.5 Hz" should read --J=5.1 Hz, 1.5 Hz--.

Column 62, line 1, "1H, d, J=8 Hz" should read --1H, d, J=3 Hz--;

line 59, "$C_{20}H_{19}H_3O_4$" should read --$C_{20}H_{19}N_3O_4$--.

Column 63, line 29, "4-3-nitrophenyl" should read --4-(3-nitrophenyl--.

Column 65, line 37, "Found: 467,18453" should read --Found: 467.18453--.

Column 66, line 33-34, "250~2.82 (6 H, m), 310-3.27" should read --2.50~2.82 (6 H, m), 3.10-3.27--;

line 40, "2-propene-1-y" should read --2-propene-1-yl--;

line 68, "[1.5 mmol)" should read --(1.5 mmol)--.

Column 67, line 12, "(100%)" should read --(100%).--.

UNITED STATES PATENT AND TRADEMARK OFFICE
CERTIFICATE OF CORRECTION

PATENT NO.  : 5,276,150
DATED       : January 4, 1994
INVENTOR(S) : Hiroshi IKAWA, et al.

It is certified that error appears in the above-identified patent and that said Letters Patent is hereby corrected as shown below:

Column 68, line 67, "3-(2-furyl}" should read --3-(2-furyl)--.

Column 69, line 2, "[2 mmol)" should read --(2 mmol)--;
         line 53, "[1 mmol)" should read --(1 mmol)--.

Column 70, line 39, "4-(3-nitrophenyl}" should read --4-(3-nitrophenyl)--;
         line 41, "[2 mmol) should read --(2 mmol)--.

Column 71, line 39, "[5 mmol)" should read --(5 mmol)--.

Column 73, line 19, "[1 mmol)" should read --(1 mmol)--.

Column 75, line 57, "[2 mmol)" should read --(2 mmol)--.

Column 87, line 60, "[E)-2-butene" should read --(E)-2-butene--.

Column 88, line 1, "[2E,4E)" should read --(2E,4E)--.

UNITED STATES PATENT AND TRADEMARK OFFICE
CERTIFICATE OF CORRECTION

PATENT NO. : 5,276,150

DATED : January 4, 1994

INVENTOR(S) : Hiroshi IKAWA, et al.

It is certified that error appears in the above-identified patent and that said Letters Patent is hereby corrected as shown below:

Column 88, line 5, "(1-imidazolylmethyl}" should read --(1-imidazolylmethyl)--.

Signed and Sealed this

Fourteenth Day of November, 1995

*Attest:*

BRUCE LEHMAN

*Attesting Officer*    *Commissioner of Patents and Trademarks*